United States Patent [19]
Fukuda et al.

[11] Patent Number: 6,162,828
[45] Date of Patent: Dec. 19, 2000

[54] CYSTEINE PROTEASE INHIBITOR

[75] Inventors: Tsunehiko Fukuda, Kyoto; Yukio Fujisawa; Hiroyuki Watanabe, both of Kobe, all of Japan

[73] Assignee: Takeda Chemical Industries, Ltd., Osaka, Japan

[21] Appl. No.: 08/648,145

[22] PCT Filed: Mar. 29, 1996

[86] PCT No.: PCT/JP96/00840

§ 371 Date: May 20, 1996

§ 102(e) Date: May 20, 1996

[87] PCT Pub. No.: WO96/30395

PCT Pub. Date: Oct. 3, 1996

[30] Foreign Application Priority Data

Mar. 31, 1995 [JP] Japan ........................... 7/75593
Mar. 31, 1995 [JP] Japan ........................... 7/75594
Oct. 13, 1995 [JP] Japan ........................... 7/265723

[51] Int. Cl.[7] .................................................. A61K 31/195
[52] U.S. Cl. .................... 514/564; 514/510; 514/114; 514/311; 514/533; 514/562; 560/41; 560/24; 546/169
[58] Field of Search .............................. 562/450, 14, 430; 514/564, 510, 114, 562, 311, 533; 560/41, 24; 546/169

[56] References Cited

U.S. PATENT DOCUMENTS 4,178,371  12/1979  Morgan .................................. 424/177

FOREIGN PATENT DOCUMENTS

| | | |
|---|---|---|
| 0 221 019 | 5/1987 | European Pat. Off. . |
| 0 519 748 | 12/1992 | European Pat. Off. . |
| 0 529 713 | 3/1993 | European Pat. Off. . |
| 0 533 226 | 3/1993 | European Pat. Off. . |
| 0 533 350 | 3/1993 | European Pat. Off. . |
| 0 547 699 | 6/1993 | European Pat. Off. . |
| 0 603 769 | 6/1994 | European Pat. Off. . |
| 0 618 223 | 10/1994 | European Pat. Off. . |
| 0 623 592 | 11/1994 | European Pat. Off. . |
| 0 623 606 | 11/1994 | European Pat. Off. . |
| 0 628 550 | 12/1994 | European Pat. Off. . |
| 0 632 051 | 1/1995 | European Pat. Off. . |
| 0 644 197 | 3/1995 | European Pat. Off. . |
| 0 644 198 | 3/1995 | European Pat. Off. . |
| 7-242599 | 9/1995 | Japan . |
| 92/22570 | 12/1992 | WIPO . |
| 93/05011 | 3/1993 | WIPO . |
| 93/05071 | 3/1993 | WIPO . |
| 93/09135 | 5/1993 | WIPO . |
| 93/16710 | 9/1993 | WIPO . |
| 94/03480 | 2/1994 | WIPO . |
| 94/04172 | 3/1994 | WIPO . |
| 95/05192 | 2/1995 | WIPO . |
| 95/23222 | 8/1995 | WIPO . |
| 95/26958 | 10/1995 | WIPO . |
| 95/29672 | 11/1995 | WIPO . |
| 95/33751 | 12/1995 | WIPO . |
| 95/35308 | 12/1995 | WIPO . |
| 96/03982 | 2/1996 | WIPO . |

OTHER PUBLICATIONS

Graybill et al., "Preparation and evaluation of peptide aspartyl hemiacetals as reversible inhibitors of interleukin–1β converting enzyme (ICE)", International Journal of Peptide & Protein Research, vol. 44, pp. 173–182, 1994.

(List continued on next page.)

Primary Examiner—Samuel Barts
Attorney, Agent, or Firm—Wenderoth, Lind & Ponack, LLP

[57] ABSTRACT

A pharmaceutical composition for inhibiting cysteine protease which comprises a compound of the formula:

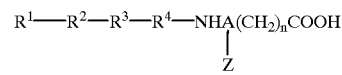

wherein $R^1$ is a hydrogen atom or an acyl group;

$R^2$, $R^3$ and $R^4$, same or different, are a bond, an amino acid residue or a group of the formula:

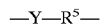

in which $R^5$ is a group resulting from imino group removal from an amino acid residue;

Y is —O—, —S— or —$NR^6$— in which $R^6$ is a hydrogen atom or a lower alkyl group;

A is

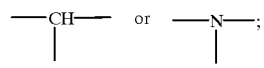

Z is a hydrogen atom, an acyl group or an optionally substituted hydrocarbon group; n is 1 or 2;

provided that when n is 1, then A is

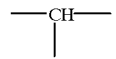

and Y is —S— or —$NR^6$—, and, at least one of $R^2$, $R^3$ and $R^4$ is the formula —Y—$R^5$—, provided that when further all Y are —$NR^6$—, at least one of the amino acid residues is not bound to amhydrogen atom at the α-carbon thereof but substituted via carbon;

provided that when n is 2 and Z is an aldehyde group, then $R^1$ is an acyl group having 6 or more carbon atoms;

provided that when n is 2 and A is,

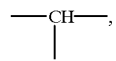

then at least one of $R^2$, $R^3$ and $R^4$ is the formula —Y—$R^5$—; or an ester or a salt thereof, and a pharmaceutically acceptable carrier.

51 Claims, No Drawings

OTHER PUBLICATIONS

Mullican et al., "The synthesis and evaluation of peptidyl aspartyl aldehydes as inhibitors of ice", Bioorganic & Medicinal Chemistry Letters, vol. 4, No. 19, pp. 2359–2364, 1994.

Thornberry et al., "A novel heterodimeric cysteine protease is required for interleukin–1β processing in monocytes", Nature, vol. 356, pp. 768–774, 1992.

Robinson et al., "Synthesis of a peptidyl difluoro ketone bearing the aspartic acid side chain: an inhibitor of interleukin–1β converting enzyme", The Journal of Organic Chemistry, vol. 57, pp. 7309–7314, 1992.

Reiter et al., "Interleukin–1β converting enzyme", International Journal of Peptide & Protein Research, vol. 41, pp. 476–483, 1993.

Mjalli et al., "Phenylalkyl ketones as potent reversible inhibitors of interleukin–1β converting enzyme", Bioorganic & Medicinal Chemistry Letters, vol. 3, No. 12, pp. 2689–2692, 1993.

Mjalli et al., "Synthesis of a peptidyl 2,2–difluoro–4–phenylbutyl ketone and its evaluation as an inhibitor of interleukin–1β converting enzyme", Bioorganic & Medicinal Chemistry Letters, vol. 3, No. 12, pp. 2693–2698, 1993.

Mjalli et al., "Activated ketones as potent reversible inhibitors of interleukin–1β converting enzyme", Bioorganic & Medicinal Chemistry Letters, vol. 4, No. 16, pp. 1965–1968, 1994.

Revesz et al., "Synthesis of P1 aspartate–based peptide acyloxymethyl and fluoromethyl ketones as inhibitors of interleukin–1β–converting enzyme", Tetrahedron Letters, vol. 35, No. 52, pp. 9693–9696, 1994.

Dolle et al., "Aspartyl α–((1–phenyl–3–(trifluoromethyl)–pyrazol–5–yl)oxy)methyl ketones as interleukin–1β converting enzyme inhibitors. Significance of the $P_1$ and $P_3$ amido nitrogens for enzyme–peptide inhibitor binding", Journal of Medicinal Chemistry, vol. 37, No. 23, pp. 3963–3966, 1994.

Dolle et al., "$P_1$ aspartate–based peptide α–((2,6–dichlorobenzoyl)oxy)methyl ketones as potent time–dependent inhibitors of interleukin–1β–converting enzyme", vol. 37, pp. 563–564, 1994.

Dolle et al., "Aspartyl α–((diphenylphosphinyl)oxy)methyl ketones as novel inhibitors of interleukin–1β converting enzyme. Utility of the diphenylphosphinic acid leaving group for the inhibition of cysteine proteases", J. Med. Chem., vol. 38, pp. 220–222, 1995.

Mjalli et al., "Inhibition of interleukin–1β converting enzyme by n–acyl–aspartic acid ketones", Bioorganic & Medicinal Chemistry Letters, vol. 5, No. 13, pp. 1405–1408, 1995.

Mjalli et al., "Inhibition of interleukin–1β converting enzyme by n–acyl–aspartyl aryloxymethyl ketones", Bioorganic & Medicinal Chemistry Letters, vol. 5, No. 13, pp. 1409–1414, 1995.

Fletcher et al., "A synthetic inhibitor of interleukin–1β converting enzyme prevents endotoxin–induced interleukin–1β production in vitro and in Vivo", Journal of Interferon and Cytokine Research, vol. 15, No. 1, pp. 243–248, 1995.

Prasad et al., "Structural and stereochemical requirements of time–dependent inactivators of the interleukin–1β converting enzyme", Bioorganic & Medicinal Chemistry Letters, vol. 5, No. 4, pp. 315–318, 1995.

Elford et al., "Reduction of inflammation and pyrexia in the rat by oral administration of SDZ 224–015, an inhibitor of the interleukin–1β converting enzyme", British Journal of Pharmacology, No. 115, No. 4, pp. 601–606, 1995.

Miller et al., "Inhibition of mature IL–1β production in murine macrophages and a murine model of inflammation by WIN 67694, an inhibitor of IL–1β converting enzyme", The Journal of Immunology, vol. 154, Nos. 1–12, pp. 1331–1338, 1995.

Chapman et al., "Synthesis of a potent, reversible inhibitor of interleukin–1β converting enzyme", Bioorganic & Medicinal Chemistry Letters, vol. 2, No. 6, pp. 613–618, 1992.

B. Weinstein, "Chemistry and Biochemistry of Amino Acids, Peptides, and Proteins", vol. 7, Chapter 5, Spatola, Peptide Backbone Modifications, pp. 267–295.

P. Savory et al., "Reaction of Proteasomes with Peptidylchloromethanes and peptidyldiazomethanes", Chemical Abstracts, Abstract No. 48746w, vol. 120, No. 5, p. 414, Jan. 31, 1994.

Dolle et al., "$P_1$ Aspartate–based peptide α–((2,6–dichlorobenzoyl)oxy)methyl Ketones as potent time–dependent inhibitors of interleukin–1β–converting enzyme", Journal of Medicinal Chemistry, vol. 37, pp. 563–564, 1994.

CYSTEINE PROTEASE INHIBITOR

TECHNICAL FIELD

The present invention relates to a compound that inhibits cysteine proteases such as interleukin-1β converting enzyme (ICE), cathepsin B and cathepsin L, and more specifically to a therapeutic drug for various infectious diseases, immune diseases, bone diseases, neurologic diseases, tumors, inflammatory diseases etc.

BACKGROUND ART

In mammals, interleukin-1β (IL-1β) is produced and released mainly by peripheral monocytes, such as macrophages; interleukin-1β converting enzyme (ICE), an enzyme that converts IL-1β precursor protein (33 KD) to mature IL-1β (17 KD), cleaves the $Asp^{116}$-$Ala^{117}$ site in the precursor protein [N. A. Thornberry et al., Nature, Vol. 356, p. 768 (1992)]. IL-1β is a cytokine having various functions, especially in the cells involved in inflammation or bone diseases. For example, it stimulates polynuclear leukocyte infiltration into inflammatory sites, increases the chemotaxis of macrophages etc., attracts them to the inflammatory sites, and induces their production of various prostaglandins etc., thereby changing the pathologic state. IL-1β also exhibits potent action on bone-associated cells. In particular, it stimulates osteoclasts to considerably accentuate bone resorption. This cytokine is also profoundly involved in rheumatoid arthritis.

Recent evidence suggests the involvement of ICE in nerve cell apoptosis [V. Gazliadni et al., Science, Vol. 264, pp. 820–828 (1994)].

On the other hand, cathepsin B is assumed to play a role in antigen processing in antigen-presenting cells [Y. Matsunaga, FEBS Letters, Vol. 324, pp. 325–330 (1994)]. In addition, cathepsin L is reportedly an important enzyme that decomposes bone substrate during bone resorption by osteoclasts [E. Kakegawa et al., FEBS Letters, Vol. 321, pp. 247–250 (1994)].

These enzymes are cysteine proteases especially associated with infectious diseases, immune diseases, bone diseases etc.; research has been undertaken on inhibitors for respective enzymes. With regard to ICE inhibitors, for example, since publication of the first report of Ac-Tyr-Val-Ala-Asp-H [N. A. Thornberry et al., Nature, Vol. 356, p. 768 (1992)], a peptide-derived inhibitor containing 3-amino-4-oxobutanoic acid at its C-terminal, peptide type inhibitors containing various aspartic acid derivatives, such as Ac-Tyr-Val-Ala-Asp-$CH_2OC(O)Ar$ [N. A. Thornberry et al., Biochemistry, Vol. 33, pp. 3934–3940 (1994)], γ-pyron-3-acetic acid [M. J. Salvatore et al., Journal of Natural Products, Vol. 57, pp. 755–760 (1994)] etc. have been reported. As concerns cathepsin B or L inhibitors, peptidyl (acyloxy) methyl ketones are reported by D. Bromme et al. in Biological Chemistry Hoppe-Seyler, Vol. 375, pp. 343–347 (1994) and by B. M. Wazner et al. in the Journal of Medicinal Chemistry, Vol. 37, pp. 1833–1840 (1994); norleucinal-containing peptide-derived inhibitors are reported in Japanese Patent Unexamined Publication No. 155764/1993; peptidyl phenoxymethyl ketones are reported in WO-9404172; leucinal-containing peptide-derived inhibitors are reported in Japanese published unexamined patent application No. 202170/1992; epoxysuccinic acid derivatives are reported in Japanese published unexamained patent application No. 304075/1990; and norleucinal-containing peptide-derived inhibitors effective against bone diseases are reported in Japanese published unexamined patent application No. 268145/1990. Also, Japanese publication of translations of International patent application 510986/1994 reports on a peptide compound having a glutamic acid derivative at its C-terminal as a picornavirus protease inhibitor; actually synthesized compounds as such include the following:

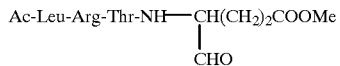

DISCLOSURE OF INVENTION

However, even these investigators have failed to provide a practically applicable therapeutic agent.

The object of the present invention is to provide a therapeutic drug that acts against various infectious diseases, immune diseases, bone diseases, neurologic diseases, inflammatory diseases and tumors, by specifically or concomitantly inhibiting ICE, cathepsin B and cathepsin L.

Against the above-described technical background, the present inventor extensively investigated protein decomposing enzyme inhibitors, and found that a peptide that contains an aspartic acid or a glutamic acid derivative and that may have a —CO—O— or —CO—S— bond, more specifically a compound represented by the formula:

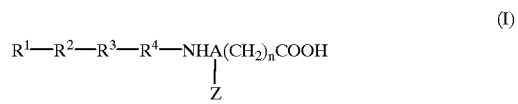

(I)

wherein $R^1$ is a hydrogen atom or an acyl group;

$R^2$, $R^3$ and $R^4$, same or different, are a bond, an amino acid residue or a group of the formula:

in which $R^5$ is a group resulting from removing the imino group from an amino acid residue;

Y is —O—, —S— or —$NR^6$— in which $R^6$ is a hydrogen atom or a lower alkyl group;

A is

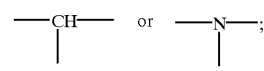

Z is a hydrogen atom, an acyl group or an optionally substituted hydrocarbon group; and n is 1 or 2;

provided that when n is 1, then A is

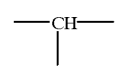

and Y is —S— or —$NR^6$—, and, at least one of $R^2$, $R^3$ and $R^4$ is the formula —Y—$R^5$, provided that when further all Y are —$NR^6$—, then at least one of the amino acid residues is not bound to hydrogen at the α-carbon thereof but substituted via carbon;

provided that when n is 2 and Z is an aldehyde group, then $R^1$ is an acyl group having 6 or more carbon atoms;

provided that when n is 2 and A is,

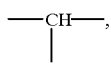

then at least one of $R^2$, $R^3$ and R4 is the formula $-Y-R^5-$;

or an ester or a salt thereof (hereinafter also referred to as compound (I)), serves excellently as a cysteine protease inhibitor (e.g. ICE inhibitor), and a compound of the formula:

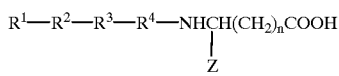
(I')

wherein $R^1$ is a hydrogen atom or an acyl group;

$R^2$, $R^3$ and $R^4$, same or different, are a bond, an amino acid residue or a group of the formula:

in which $R^5$ is a group resulting from removing the imino group from an amino acid residue;

Y is $-O-$, $-S-$ or $-NR^6-$ in which $R^6$ is a hydrogen atom or a lower alkyl group;

A is

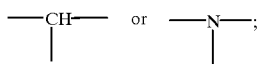

Z is a hydrogen atom, an acyl group or an optionally substituted hydrocarbon group; and n is 1 or 2;

provided that when n is 1, then A is

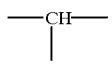

and Y is $-S-$ or $-NR^6-$, and, at least one of $R^2$, $R^3$ and $R^4$ is the formula $-Y-R^5$, provided that when further all Y are $-NR^6-$, then at least one of the amino acid residues is not bound to hydrogen at the a-carbon thereof but substituted via carbon;

provided that when n is 2 and A is,

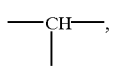

then at least one of $R^2$, $R^3$ and $R^4$ is the formula $-Y-R^5-$;

or an ester or a salt thereof (hereinafter also referred to as compound (I')), serves excellently as an ICE inhibitor, which is one kind of cystein protease inhibitor.

And, for the first time synthesized compound (I) or (I'), a compound of the formula:

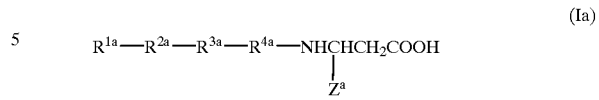
(Ia)

wherein $R^{1a}$ is an aralkyloxycarbonyl group;

$R^{2a}$, $R^{3a}$ and $R^{4a}$, same or different, are a bond, an amino acid residue or a group of the formula:

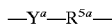

in which $R^{5a}$ is a group resulting from removing the imino group from an amino acid residue; and $Y^a$ is $-S-$ or $-NR^{6a}-$ in which $R^{6a}$ is a hydrogen atom or a lower alkyl group; $Z^a$ is an aldehyde or an acetal group;

provided that at least one of $R^{2a}$, $R^{3a}$ and $R^{4a}$ is the formula $-Y^a-R^{5a}$, provided that when all $Y^a$ are $-NR^{6a}-$, then at least one of the amino acid residues is not bound to hydrogen at the α-carbon thereof but substituted via carbon;

or an ester or a salt thereof (hereinafter also referred to as compound (Ia)), a compound of the formula:

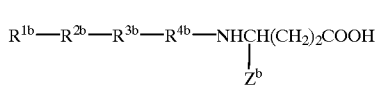
(Ib)

wherein $R^{1b}$ is an aralkyloxycarbonyl group, a cycloalkylcarbonyl group, a heterocyclic-carbonyl group, an arylcarbonyl group which may be substituted with hydroxyl, carboxyl or benzyloxycarbonyl, an arylsulfonyl group which may be substituted with hydroxyl;

$R^{2b}$, $R^{3b}$ and $R^{4b}$, same or different, are a bond, an amino acid residue or a group of the formula:

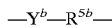

in which $R^{5b}$ is a group resulting from removing the imino group from an amino acid residue; $Y^b$ is $-O-$, $-S-$ or $-NR^{6b}-$ in which $R^6$b is a hydrogen atom or a lower alkyl group; and $Z^b$ is an aldehyde group, an acetal group, an acylalkylcarbonyl group or a substituted alkenyl group;

provided that at least one of $R^{2b}$, $R^{3b}$ and $R^{4b}$ is the formula $-Y^b-R^{5b}$;

or an ester or a salt thereof (hereinafter also referred to as compound (Ib)), and a compound of the formula:

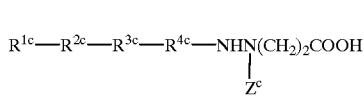
(Ic)

wherein $R^{1c}$ is an aralkyloxycarbonyl group or an arylcarbonyl group;

$R^{2c}$, $R^{3c}$ and $R^{4c}$, same or different, are a bond, an amino acid residue or a group of the formula:

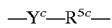

in which $R^{5c}$ is a group resulting from removing the imino group from an amino acid residue;

$Y^c$ is —O—, —S— or —NR$^{6c}$— in which R$^{6c}$ is a hydrogen atom or a lower alkyl group;

$Z^c$ is an aldehyde group, an acetal group, a substituted carbonyl group or an substituted alkenyl group; or an ester or a salt thereof, (hereinafter also referred to as compound (Ic)), serve excellently as a cystein protease inhibitor (e.g. ICE inhibitor). The inventor investigated further on the basis of these findings, and developed the present invention.

Accordingly, the present invention relates to:

(1) a pharmaceutical composition for inhibiting cysteine protease which comprises compound (I) and a pharmaceutically acceptable carrier, (2) a pharmaceutical composition for inhibiting cysteine protease which comprises compound (I') and a pharmaceutically acceptable carrier, (3) compound (Ia), (4) compound (Ib), (5) compound (Ic), (6) a pharmaceutical composition for inhibiting ICE which comprises compound (Ia), (Ib) or (Ic), and a pharmaceutically acceptable carrier and so on.

With respect to formulas (I) and (I') above, $R^1$ represents a hydrogen atom or an acyl group.

The "acyl group" represented by $R^1$ is exemplified by acyl groups derived from carboxylic acids that may be substituted, oxycarboxylic acids that may be substituted, sulfonic acids that may be substituted, sulfinic acids that may be substituted, etc., represented by $R^7CO—$, $R^8OCO—$, $R^9SO_2—$ and $R^{10}SO—$, respectively, in which $R^7$, $R^8$, $R^9$ and $R^{10}$ independently represent a hydrocarbon group or heterocyclic group that may be substituted.

The "hydrocarbon group" of the "hydrocarbon group that may be substituted" represented by $R^7$, $R^8$, $R^9$ or $R^{10}$, is exemplified by linear or branched aliphatic hydrocarbon groups such as alkyl groups and alkenyl groups; saturated or unsaturated alicyclic hydrocarbon groups such as cycloalkyl groups, cycloalkenyl groups and cycloalkadienyl groups; monocyclic or condensed polycyclic aryl groups and aralkyl groups, with preference given to aryl groups and aralkyl groups.

Alkyl groups exemplifying the "hydrocarbon group" represented by $R^7$, $R^8$, $R^9$ or $R^{10}$ include alkyl groups having 1 to 20 carbon atoms, such as methyl, ethyl, propyl, isopropyl, butyl, isobutyl, sec-butyl, tert-butyl, pentyl, isopentyl, neopentyl, tert-pentyl, 1-ethylpropyl, hexyl, isohexyl, heptyl, octyl, decyl, dodecyl, tridecyl, tetradecyl, hexadecyl, octadecyl, nonadecyl and eicosanyl.

Alkenyl groups exemplifying the "hydrocarbon group" represented by $R^7$, $R^8$, $R^9$ or $R^{10}$ include alkenyl groups having 2 to 20 carbon atoms, such as vinyl, allyl, isopropenyl, 1-propenyl, 2-methyl-1-propenyl, 1-butenyl, 2-butenyl, 3-butenyl, 2-ethyl-l-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl, and heptenyl, octenyl, decenyl, tetradecenyl, octadecenyl and eicosenyl, each of which has a double bond at a particular position.

Cycloalkyl groups exemplifying the "hydrocarbon group" represented by $R^7$, $R^8$, $R^9$ or $R^{10}$ include cycloalkyl groups having 3 to 20 carbon atoms, such as cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1] nonyl, bicyclo 4.2.1]nonyl, bicyclo[4.3.1]decyl and adamantyl.

Cycloalkenyl groups exemplifying the "hydrocarbon group" represented by $R^7$, $R^8$, $R^9$ or $R^{10}$ include cycloalkenyl groups having 4 to 20 carbon atoms, such as 2-cyclopentyl-1-yl, 3-cyclopenten-1-yl, 2-cyclohexen-1-yl and 3-cyclohexen-1-yl.

Cycloalkadienyl groups exemplifying the "hydrocarbon group" represented by $R^7$, $R^8$, $R^9$ or $R^{10}$ include cycloalkadienyl groups having 4 to 20 carbon atoms, such as 2,4-cyclopentadien-1-yl, 2,4-cyclohexadien-1-yl and 2,5-cyclohexadien-1-yl.

Aryl groups exemplifying the "hydrocarbon group" represented by $R^7$, $R^8$, $R^9$ or $R^{10}$ include aryl groups having 6 to 20 carbon atoms, such as phenyl, indenyl, naphthyl (1-naphthyl, 2-naphthyl), anthryl, phenanthryl, acenaphthylenyl and fluorenyl (9-fluorenyl, 1-fluorenyl).

Aralkyl groups exemplifying the "hydrocarbon group" represented by $R^7$, $R^8$, $R^9$ or $R^{10}$ include aralkyl groups having 7 to 20 carbon atoms, such as benzyl, phenethyl, 3-phenylpropyl, 1-naphthylmethyl, 2-naphthylmethyl, 9-fluorenylmethyl and trityl, with preference given to those whose alkyl moiety is a $C_{1-6}$ alkyl group, such as benzyl, phenethyl and 9-fluorenylmethyl. 10 Preferable alkyl groups exemplifying the "hydrocarbon group" represented by $R^7$, $R^8$, $R^9$ or $R^{10}$ include alkyl groups having 10 to 20 carbon atoms, such as decyl, dodecyl, tridecyl, tetradecyl, hexadecyl, octadecyl, nonadecyl and eicosanyl.

Preferable aryl groups exemplifying the "hydrocarbon group" represented by $R^7$, $R^8$, $R^9$ or $R^{10}$ include condensed polycyclic aryl groups having 7 to 20 carbon atoms, such as indenyl, naphthyl, anthryl, phenanthryl, acenaphthylenyl and fluorenyl.

Preferable aralkyl groups exemplifying the "hydrocarbon group" represented by $R^7$, $R^8$, $R^9$ or $R^{10}$ include aralkyl groups having 8 to 20 carbon atoms, such as phenethyl, 3-phenylpropyl, 1-naphthylmethyl, 2-naphthylmethyl, 9-fluorenylmethyl and trityl.

The "heterocyclic group" of the "heterocyclic group that may be substituted," represented by $R^7$, $R^8$, $R^9$ or $R^{10}$, is an aromatic heterocyclic group having at least one hetero atom of oxygen, sulfur or nitrogen as a ring component atom, and is exemplified by 5- to 8-membered monocyclic, bicyclic or tricyclic heterocyclic groups, including aromatic monocyclic heterocyclic groups such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pydidazinyl, pyrimidinyl, pyrazinyl, triazinyl and quinolyl; and bicyclic or tricyclic aromatic condensed heterocyclic groups such as benzofuranyl, isobenzofuranyl, benzo[b]thienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthylidinyl, purinyl, pteridinyl, carbazolyl, α-carbolinyl, β-carbolinyl, γ-carbolinyl, acridinyl, phenoxadinyl, phenothiazinyl, phenazinyl, phenoxathiinyl, thianthrenyl, phenatrizinyl, phenatrolinyl, indolidinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a] pyrimidinyl, 1,2,4-triazolo[4,3-a]pyridyl and 1,2,4-triazolo [4,3-a]pyridazinyl.

The "hydrocarbon group or heterocyclic group" of the "hydrocarbon group or heterocyclic group that may be substituted," represented by $R^7$, $R^8$, $R^9$ or $R^{10}$ above, may have 1 or more, preferably 1 to 3, substituents at appropriate positions, which are exemplified by amino groups, mono- or di-substituted amino groups, cyclic amino groups, amidino groups, carbamoyl groups, N-mono- or di-lower alkylcarbamoyl groups, carboxyl groups, lower alkoxycarbonyl groups, hydroxyl groups, lower alkoxy groups, lower alkenyloxy groups, cycloalkyloxy groups, aralkyloxy groups, aryl groups, aryloxy groups, mercapto groups, lower alkylthio groups, aralkylthio groups, arylthio groups, aralkyloxycarbonyl groups, heterocyclic groups, sulfo groups, cyano groups, azido groups, nitro groups, nitroso groups and halogen atoms.

Here, the term "lower" means that the alkyl moiety has 1 to 6 carbon atoms, unless otherwise specified.

Examplary substituents for the "mono- or di-substituted amino group" as a substituent for the "hydrocarbon group or heterocyclic group" represented by $R^7$, $R^8$, $R^9$ or $R^{10}$ above include lower alkyl groups (e.g., $C_{1-6}$ alkyl groups such as methyl, ethyl, propyl, isopropyl, butyl, isobutyl, sec-butyl, tert-butyl, pentyl, isopentyl, neopentyl, tert-pentyl, 1-ethylpropyl, hexyl and isohexyl), $C_{3-7}$ cycloalkyl groups (e.g., cyclopropyl, cyclobutyl, cyclopentyl, cyclohexyl), aryl groups, 5- to 8-membered monocyclic, bicylic or tricyclic heterocyclic groups having at least one hetero atom of nitrogen, oxygen or sulfur, $C_{7-11}$ aralkyl groups (e.g., benzyl, phenethyl, 3-phenylpropyl), $C_{1-4}$ acyl groups (e.g., formyl, acetyl), carbamoyl groups, N-mono- or di-lower alkylcarbamoyl groups, lower alkoxycarbonyl groups, hydroxyl groups, lower alkoxy groups and aralkyloxy groups. N,N-di-substituted amino groups include those wherein one substituent is any one of these substituents and the other is, for example, one of the above-mentioned lower alkyl groups, $C_{3-7}$ cycloalkyl groups, aryl groups or $C_{7-11}$ aralkyl groups.

Here, aryl groups and heterocyclic groups mentioned as examplary substituents for the "mono- or di-substituted amino group" are exemplified by the same aryl groups as those exemplifying the "hydrocarbon group that may be substituted," represented by $R^7$, $R^8$, $R^9$ or $R^{10}$ above, and the same heterocyclic groups as those exemplifying the "heterocyclic group that may be substituted."

N-mono- or di-lower alkylcarbamoyl groups, lower alkoxycarbonyl groups, lower alkoxy groups and aralkyloxy groups mentioned as examplary substituents for the "mono- or di-substituted amino group" are exemplified by the same groups as the N-mono- or di-lower alkylcarbamoyl groups, lower alkoxycarbonyl groups, lower alkoxy groups and aralkyloxy groups described below.

The "cyclic amino group" as a substituent for the "hydrocarbon group or heterocyclic group" represented by $R^7$, $R^8$, $R^9$ or $R^{10}$ above is exemplified by 1-azetidinyl, 1-pyrrolidinyl, piperidino, thiomorpholino, morpholino, 1-piperazinyl, and 1-piperazinyl having a lower alkyl group (e.g., a $C_{1-6}$ alkyl group such as methyl, ethyl, propyl, isopropyl, butyl, isobutyl, sec-butyl, tert-butyl, pentyl, isopentyl, neopentyl, tert-pentyl, 1-ethylpropyl, hexyl or isohexyl), an aralkyl group, an aryl group at its 4-position, or the like.

Here, aralkyl groups and aryl groups mentioned as substituents for 1-piperazinyl exemplifying the "cyclic amino group" are exemplified by the same aryl groups and aralkyl groups as those exemplifying the "hydrocarbon group that may be substituted," represented by $R^7$, $R^8$, $R^9$ or $R^{10}$ above.

The "N-mono- or di-lower alkylcarbamoyl group" as a substituent for the "hydrocarbon group or heterocyclic group" represented by $R^7$, $R^8$, $R^9$ or $R^{10}$ above is exemplified by N-mono-$C_{1-6}$ alkylcarbamoyl groups such as N-methylcarbamoyl, N-ethylcarbamoyl, N-propylcarbamoyl, N-isopropylcarbamoyl and N-butylcarbamoyl; and N,N-di-$C_{1-6}$ alkylcarbamoyl groups such as N,N-dimethylcarbamoyl, N,N-diethylcarbamoyl, N,N-dipropylcarbamoyl and N,N-dibutylcarbamoyl.

The "lower alkoxycarbonyl group" as a substituent for the "hydrocarbon group or heterocyclic group" represented by $R^7$, $R^8$, $R^9$ or $R^{10}$ above is exemplified by $C_{1-6}$ alkoxycarbonyl groups such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl and tert-pentyloxycarbonyl, with preference given to methoxycarbonyl, ethoxycarbonyl, propoxycarbonyl etc.

The "lower alkoxy group" as a substituent for the "hydrocarbon group or heterocyclic group" represented by $R^7$, $R^8$, $R^9$ or $R^{10}$ above is exemplified by alkoxy groups having 1 to 6 carbon atoms, such as methoxy, ethoxy, propoxy, isopropoxy, butoxy, isobutoxy, sec-butoxy, tert-butoxy, pentyloxy, isopentyloxy, tert-pentyloxy, neopentyloxy, hexyloxy, isohexyloxy, 1,1-dimethylbutoxy, 2,2-dimethylbutoxy and 3,3-dimethylbutoxy, with preference given to alkoxy groups having 1 to 4 carbon atoms, such as methoxy, ethoxy, propoxy, isopropoxy, butoxy and isobutoxy.

The "lower alkenyloxy group" as a substituent for the "hydrocarbon group or heterocyclic group" represented by $R^7$, $R^8$, $R^9$ or $R^{10}$ above is exemplified by alkenyloxy groups having 1 to 6 carbon atoms, such as allyloxy, 2-butenyloxy and 2-pentenyloxy.

The "cycloalkyloxy group" as a substituent for the "hydrocarbon group or heterocyclic group" represented by $R^7$, $R^8$, $R^9$ or $R^{10}$ above is exemplified by cycloalkyloxy groups having 1 to 6 carbon atoms, such as cyclobutyloxy, cyclopentyloxy and cyclohexyloxy.

The "aralkyloxy group" as a substituent for the "hydrocarbon group or heterocyclic group" represented by $R^7$, $R^8$, $R^9$ or $R^{10}$ above is exemplified by aralkyloxy groups having 7 to 20 carbon atoms, such as benzyloxy, phenethyloxy, 3-phenylpropyloxy, 1-naphthylmethyloxy, 2-naphthylmethyloxy, 9-fluorenylmethyloxy and trityloxy.

The "aryloxy group" as a substituent for the "hydrocarbon group or heterocyclic group" represented by $R^7$, $R^8$, $R^9$ or $R^{10}$ above is exemplified by aryloxy groups having 6 to 20 carbon atoms, such as phenyloxy, naphthyloxy, anthryloxy, phenanthryloxy, acenaphthylenyloxy and fluorenyloxy.

The "lower alkylthio group" as a substituent for the "hydrocarbon group or heterocyclic group" represented by $R^7$, $R^8$, $R^9$ or $R^{10}$ above is exemplified by alkylthio groups having 1 to 6 carbon atoms, such as methylthio, ethylthio, propylthio, isopropylthio, butylthio, isobutylthio, secbutylthio, tert-butylthio, pentylthio, isopentylthio, neopentylthio, tert-pentylthio, 1-ethylpropylthio, hexylthio and isohexylthio.

The "aralkylthio group" as a substituent for the "hydrocarbon group or heterocyclic group" represented by $R^7$, $R^8$, $R^9$ or $R^{10}$ above is exemplified by aralkylthio groups having 7 to 20 carbon atoms, such as benzylthio, phenethylthio, 3-phenylpropylthio, 1-naphthylmethylthio, 2-naphthylmethylthio, 9-fluorenylmethylthio and tritylthio.

The "arylthio group" as a substituent for the "hydrocarbon group or heterocyclic group" represented by $R^7$, $R^8$, $R^9$ or $R^{10}$ above is exemplified by arylthio group having 6 to 20 carbon atoms, such as phenylthio, naphthylthio, anthrylthio, phenanthrylthio, acenaphthylenylthio and fluorenylthio.

The "aryl group" as a substituents for the "hydrocarbon group or heterocyclic group" represented by $R^7$, $R^8$, $R^9$ or $R^{10}$ above is exemplified by the same "aryl group" as those exemplifying the "hydrocarbon group" of "hydrocarbon group that may be substituted for" represented by $R^7$, $R^8$, $R^9$ or $R^{10}$.

The "heterocyclic group" as a substituent for the "hydrocarbon group or heterocyclic group" represented by $R^7$, $R^8$, $R^9$ or $R^{10}$ above is exemplified by the same "heterocyclic groups" as those exemplifying the "heterocyclic group that may be substituted for," represented by $R^7$, $R^8$, $R^9$ or $R^{10}$ above.

The "halogen atom" as a substituent for the "hydrocarbon group or heterocyclic group" represented by $R^7$, $R^8$, $R^9$ or $R^{10}$ above is exemplified by fluorine, chlorine, bromine and iodine, with preference given to fluorine, chlorine, bromine etc.

The "aralkyloxycarbonyl group" as a substituent for the "hydrocarbon or heterocyclic group" represented by $R^7$, $R^8$, $R^9$ or $R^{10}$ above is exemplified by the same "aralkyloxycarbonyl group" as preferable example of $R^1$.

The "acyl group" represented by $R^1$ is preferably one wherein the "hydrocarbon group that may be substituted for," represented by $R^7$, $R^8$, $R^9$ or $R^{10}$ above, is an aryl group or an aralkyl group, and preferably has 10 to 20 carbon atoms.

Also, $R^1$ is preferably a group represented by the formula $R^7CO—$ or $R^8OCO—$ in which the symbols have the same definitions as those given above, for example, more preferably an aralkyloxycarbonyl group, aryloxycarbonyl group, aralkylcarbonyl group or an arylcarbonyl group, most preferably aralkyloxycarbonyl or arylcarbonyl group.

Preferable aralkyloxycarbonyl groups include aralkyloxycarbonyl groups having 7 to 20 carbon atoms, such as benzyloxycarbonyl, phenethyloxycarbonyl, 3-phenylpropyloxycarbonyl, 1-naphthylmethyloxycarbonyl, 2-naphthylmethyloxycarbonyl, 9-fluorenylmethyloxycarbonyl and trityloxycarbonyloxycarbonyl, with preference given to those whose alkyl moiety is a $C_{1-6}$ alkyl group, such as benzyloxycarbonyl, phenethyl and 9-fluorenylmethyloxycarbonyl, more preferably 9-fluorenylmethyloxycarbonyl.

Preferable aryloxycarbonyl groups include aryl groups having 6 to 20 carbon atoms, such as phenyloxycarbonyl, indenyloxycarbonyl, naphthyloxycarbonyl, anthryloxycarbonyl, phenanthryloxycarbonyl, acenaphthylenyloxycarbonyl and fluorenyloxycarbonyl.

Preferable aralkylcarbonyl groups include aralkylcarbonyl groups having 7 to 20 carbon atoms, such as benzylcarbonyl, phenethylcarbonyl, 3-phenylpropylcarbonyl, 1-naphthylmethyloxycarbonyl, 2-naphthylmethylcarbonyl, 9-fluorenylmethylcarbonyl and tritylcarbonyl, with preference given to those whose alkyl moiety is a $C_{1-6}$ alkyl group, such as benzylcarbonyl, phenethyl and 9-fluorenylmethylcarbonyl.

Preferable arylcarbonyl groups include aryl groups having 6 to 20 carbon atoms, such as phenylcarbonyl, indenylcarbonyl, naphthylcarbonyl, anthrylcarbonyl, phenanthrylcarbonyl, acenaphthylenylcarbonyl and fluorenylcarbonyl, more preferably naphthylcarbonyl.

With respect to formulas (I) and (I') above, $R^2$, $R^3$ and $R^4$, same or different, represent a bond, an amino acid residue or a group of the formula:

—Y—$R^5$— wherein $R^5$ represents a group resulting from removing the imino group from an amino acid residue; and Y represents —O—, —S— or —$NR^6$— in which $R^6$ represents a hydrogen atom or lower alkyl groups having 1 to 6 carbon atoms.

Here, "amino acid residue" represents by $R^2$, $R^3$ and $R^4$ and "group resulting from removing the imino group from an amino acid residue," represented by $R^5$ include the term amino acid is a generic designation for groups resulting from replacement of at least one hydrogen atom in the parent structure of carboxylic acid by an amino group, including α-, β-, γ- and δ-amino acids having a parent structure with 2 to 20 carbon atoms. Of these amino acids, α-amino acids are preferred, including protein component amino acids such as alanine, arginine, asparagine, aspartic acid, cysteine, glutamic acid, glutamine, glycine, histidine, leucine, isoleucine, lysine, methionine, phenylalanine, proline, serine, threonine, tryptophan, tyrosine and valine; and other amino acids such as norvaline, norleucine, 2-aminoadipic acid, 2-aminobutyric acid, 2-aminoisobutyric acid, 1-aminocyclopropanecarboxylic acid, 1-aminocyclopentanecarboxylic acid, 1-aminocyclohexanecarboxylic acid, thyronine, ornithine, hydroxyproline and hydroxylysine.

Also, the "amino acid residue" include cyclic imino acid. The "cyclic imino acid" is exemplified an optionally substituted cycloalkane carboxylic acid or an optionally substituted cycloalkene carboxylic acid which at least one of those methylene groups is substituted, specifically, such as proline, hydroxyproline, 3,4-dehydroproline, pipecoline acid,

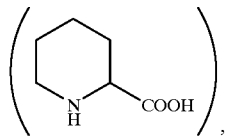

adilidine carboxylic acid, 2-azetidine carboxylic acid,

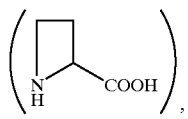

preferably proline, hydroxyproline or pipecoline acid.

The "group resulting from removing the imino group (—NH—) from an amino acid residue" represented by $R^5$ is exemplified by groups whose parent structure is based on one of linear or branched $C_{1-10}$ alkyl groups (e.g., methyl, ethyl, propyl, isopropyl, butyl, isobutyl, sec-butyl, tert-butyl, pentyl, isopentyl, neopentyl, tert-pentyl, 1-ethylpropyl, hexyl, isohexyl, heptyl, octyl, decyl); $C_{2-10}$ alkenyl groups (e.g., vinyl, allyl, isopropenyl, 1-propenyl, 2-methyl-1-propenyl, 1-, 2- or 3-butenyl, 2-ethyl-1-butenyl, 3-methyl-2-butenyl, 1-, 2-, 3- or 4-pentenyl, 4-methyl-3-pentenyl, 1-, 2-, 3-, 4- or 5-hexenyl, and heptenyl, octenyl and decenyl, each of which has a double bond at a particular position; $C_{7-20}$ aralkyl groups (e.g., benzyl, phenethyl, 3-phenylpropyl, 1-naphthylmethyl, 2-naphthylmethyl, 9-fluorenylmethyl); $C_{3-7}$ cycloalkyl groups (e.g., cyclopropyl, cyclobutyl, cyclopentyl, cyclohexyl, cycloheptyl); $C_{3-7}$ cycloalkenyl groups (e.g., 2-cyclopenten-1-yl, 3-cyclopenten-1-yl, 2-cyclohexen-1-yl and 3-cyclohexen-1-yl); $C_{6-15}$ aryl groups (e.g., phenyl, naphthyl, anthryl, phenanthryl, acenaphthylenyl, fluorenyl); $C_{3-20}$ monocyclic or condensed polycyclic heterocyclic aralkyl groups (e.g., 4-imidazolylmethyl, 3-pyridylmethyl, 4-thiazolylmethyl, 3-indolylmethyl, 3-quinolylmethyl). Those groups having patent structure bind Y and carbonyl group

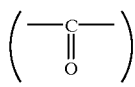

These groups may have 1 or more, preferably 1 to 3, substituents at appropriate positions, which are exemplified by amino groups, acyl-substituted amino groups, guanidino groups, acylguadino groups, acylamidino groups, amidino groups, acyl groups, carbamoyl groups, N-mono- or di-lower alkylcarbamoyl groups, carboxyl groups, lower alkoxycarbonyloxy groups, hydroxyl groups, acylhydroxyl groups, lower alkoxy groups, lower alkenyloxy groups, $C_{3-6}$ cycloalkyloxy groups, $C_{7-11}$ aralkyloxy groups, phenoxy groups, mercapto groups, acylmercapto groups, lower alkylthio groups, $C_{7-11}$ aralkylthio groups, phenylthio groups, sulfo groups, cyano groups, azide groups, nitro groups, nitroso groups and halogen atoms.

Here, the "acyl group" as a substituent for the above-mentioned acyl-substituted amino groups, acylguadino groups, acylamidino groups, acylhydroxyl groups and acylmercapto groups is exemplified by aliphatic acyl groups such as alkanoyl groups, alkenoyl groups, cycloalkanecarbonyl groups and alkanesulfonyl groups; aromatic acyl groups such as alloyl groups, arylalkanoyl groups, arylalkenoyl groups and arenesulfonyl groups; and heterocyclic aromatic acyl groups such as heterocyclic carbonyl groups and aromatic heterocyclic alkanoyl groups.

Alkanoyl groups exemplifying the substituent "acyl group" include lower ($C_{1-6}$) alkanoyl groups such as formyl, acetyl, propionyl, butyryl, isobutyryl, valeryl, isovaleryl, pivaloyl and hexanoyl.

Alkenoyl groups exemplifying the substituent "acyl group" include lower ($C_{3-8}$) alkenoyl groups such as acryloyl, methacryloyl, crotonoyl and isocrotonoyl.

Cycloalkanecarbonyl groups exemplifying the substituent "acyl group" include lower ($C_{3-7}$) cycloalkanecarbonyl groups such as cyclopropanecarbonyl groups, cyclobutanecarbonyl groups, cyclopentanecarbonyl groups and cyclohexanecarbonyl groups.

Alkanesulfonyl groups exemplifying the substituent "acyl group" include lower ($C_{1-6}$) alkanesulfonyl groups such as mesyl, ethanesulfonyl and propanesulfonyl.

Aroyl groups exemplifying the substituent "acyl group" include $C_{8-20}$ aroyl groups such as benzoyl, p-toluoyl, 1-naphthoyl and 2-naphthoyl.

Arylalkanoyl groups exemplifying the substituent "acyl group" include aryl ($C_{6-20}$)-lower ($C_{2-7}$) alkanoyl groups such as phenylacetyl, phenylpropionyl, hydroatropoyl and phenylbutyryl.

Arylalkenoyl groups exemplifying the substituent "acyl group" are alkenylcarbonyl groups substituted by an aryl group, including aryl ($C_{6-20}$)-lower ($C_{3-8}$) alkenoyl groups such as cinnamoyl and atropoyl.

Arenesulfonyl groups exemplifying the substituent "acyl group" are arylsulfonyl groups, including $C_{6-20}$ arylsulfonyl groups such as benzenesulfonyl and p-toluenesulfonyl.

Aromatic heterocyclic-carbonyl groups exemplifying the substituent "acyl group" include aromatic heterocyclic (5- to 8-membered monocyclic, bicyclic or tricyclic heterocyclic group having at least one hetero atom of oxygen, sulfur or nitrogen) carbonyl groups such as furoyl, thenoyl, nicotinoyl, isonicotinoyl, pyrrolecarbonyl, oxazolecarbonyl, thiazolecarbonyl, imidazolecarbonyl and pyrazolecarbonyl.

Heterocyclic alkanoyl groups exemplifying the substituent "acyl group" include alkylcarbonyl groups substituted by an aromatic or non-aromatic heterocyclic group, e.g., aromatic heterocyclic (5- to 8-membered monocyclic, bicyclic or tricyclic heterocyclic group having at least one hetero atom of oxygen, sulfur or nitrogen) lower ($C_{2-7}$) alkanoyl groups such as thienylacetyl, thienylpropanoyl, furylacetyl, thiazolylacetyl, 1,2,4-thiadiazolylacetyl and pyridylacetyl; and non-aromatic heterocyclic (5- to 8-membered monocyclic heterocyclic group having at least one hetero atom of oxygen, sulfur or nitrogen) lower ($C_{2-7}$) alkanoyl groups such as azetidinylcarbonyl, pyrrolidinylcarbonyl and piperidinylcarbonyl.

The above-described "lower alkoxycarbonyloxy group" is exemplified by $C_{1-6}$ alkoxy-carbonyloxy groups such as methoxycarbonyloxy, ethoxycarbonyloxy, propoxycarbonyloxy, isopropoxycarbonyloxy, butoxycarbonyloxy, isobutoxycarbonyloxy, sec-butoxycarbonyloxy, tert-butoxycarbonyloxy, pentyloxycarbonyloxy, isopentyloxycarbonyloxy, neopentyloxycarbonyloxy and tert-pentyloxycarbonyloxy.

The other groups mentioned above (acyl groups, N-mono- or di-lower alkylcarbamoyl groups, lower alkoxy groups, lower alkenyloxy groups, $C_{3-6}$ cycloalkyloxy groups, $C_{7-11}$ aralkyloxy groups, lower alkylthio groups, $C_{7-11}$ aralkylthio groups, halogen atoms) are exemplified by the same groups as those mentioned as example for the "acyl group" represented by $R^1$ and substituents for the "hydrocarbon group or heterocyclic group that may be substituted for," represented by $R^7$, $R^8$, $R^9$ or $R^{10}$, in the "acyl group."

$R^5$ is also exemplified by groups represented by the formula:

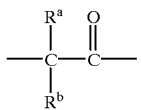

wherein $R^a$ and $R^b$, same or different, are a hydrogen atom or a $C_{1-8}$ alkyl group, and may bind together to form a ring structure. Here, the "$C_{1-8}$ alkyl group" represented by $R^a$ or $R^b$ is exemplified by methyl, ethyl, propyl, isopropyl, butyl, isobutyl, sec-butyl, tert-butyl, pentyl, isopentyl, neopentyl, tert-pentyl, 1-ethylpropyl, hexyl and isohexyl.

More specifically, $R^5$ is exemplified by groups resulting from removing the imino group from amino acids such as alanine, glutamic acid, glutamine, leucine, isoleucine, lysine, serine, threonine, valine, norvaline, norleucine, aminobutyric acid, 2-aminoisobutyric acid, more preferably, groups resulting from removing the imino group from amino acids such as valine, alanine, glutamic acid, 2-aminoisobutyric aicd.

With respect to formulas (I) and (I') above, Y represents —O—, —S— or —NR$^6$— in which $R^6$ represents a hydrogen atom or a lower alkyl group.

The "lower alkyl group" represented by $R^6$ is exemplified by linear or branched alkyl groups having 1 to 6 carbon atoms, such as methyl, ethyl, propyl, isopropyl, butyl, sec-butyl, tert-butyl, 1-ethylpropyl, pentyl, hexyl, 1,1-dimethylbutyl and 2,2-dimethylbutyl.

Y is preferably —O— or —NR$^6$—, or, —S— or —NR$^6$—.

$R^2$, $R^3$ and $R^4$ are preferably, the one is a bond and the other two are, same or different, amino acid residues.

With respect to formulas (I) and (I') above, Z represents a hydrogen atom, an acyl group or an optionally substituted hydrocarbon group.

The "acyl group" represented by Z is exemplified by acyl groups derived from oxycarboxylic acids that may be substituted, carboxylic acids that may be substituted, sulfonic acids that may be substituted, sulfinic acids that may be substituted, etc., represented by $R^{11}CO-$, $R^{12}OCO-$, $R^{13}SO_2-$ and $R^{14}SO-$, respectively, in which $R^{11}$, $R^{12}$, $R^{13}$ and $R^{14}$ independently represent a hydrogen atom or a hydrocarbon group that may be substituted).

The "hydrocarbon group that may be substituted" represented by $R^{11}$, $R^{12}$, $R^{13}$ or $R^{14}$, is exemplified by the same groups as those exemplifying the "hydrocarbon group that may be substituted," represented by $R^7$, $R^8$, $R^9$ or $R^{10}$ above.

Substituents for the "hydrocarbon group that may be substituted" represented by $R^{11}$, $R^{12}$, $R^{13}$ or $R^{14}$, are exemplified by the same substituents as those for the "hydrocarbon group that may be substituted" represented by $R^7$, $R^8$, $R^9$ or $R^{10}$ above, and by oxo groups, arylcarbonyloxy groups, arylsulfonyl groups and those groups represented by the formula:

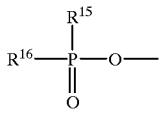

wherein $R^{15}$ and $R^{16}$ independently represent a hydrocarbon group or heterocyclic group that may be substituted.

Here, preferable "arylcarbonyloxy groups" is exemplified by arylcarbonyloxy groups having 6 to 20 carbon atoms, such as phenylcarbonyloxy indenylcarbonyloxy, naphthylcarbonyloxy, anthrylcarbonyloxy, phenanthrylcarbonyloxy, acenaphethylenylcarbonyloxy, fluorenylcarbonyloxy, etc.

The "aryl" group of those "arylcarbonyloxy groups" may be substituted for 1 to 5 substituents which are selected from halogen atoms (e.g. chloro, fluoro) and alkyl groups (e.g. $C_{1-6}$ alkyl groups such as methyl, ethyl, etc.) which may be substituted for halogen atoms (e.g. chloro, fluoro).

The "hydrocarbon group or heterocyclic group that may be substituted" represented by $R^{15}$ or $R^{16}$, is exemplified by the same groups as those exemplifying the "hydrocarbon group or heterocyclic group that may be substituted" represented by $R^7$, $R^8$, $R^9$ or $R^{10}$ above.

The "acyl group" represented by Z is preferably a group represented by the formula $R^{11}CO-$ in which the symbols have the same definitions as those given above.

The "hydrocarbon group" of "hydrocarbon group that may be substituted" represented by Z. is exemplified by the same groups as those exemplifying the "hydrocarbon group" of "hydrocarbon group that may be substituted for," represented by $R^7$, $R^8$, $R^9$ or $R^{10}$ above.

Substituents for the "hydrocarbon group that may be substituted" represented by Z, are exemplified by the same substituents as those for the "hydrocarbon group that may be substituted" represented by $R^7$, $R^8$, $R^9$ or $R^{10}$ above, and acyl groups are exemplified. These "acyl groups" are the same as those exemplifying the "acyl group" represented by Z above.

The "hydrocarbon group that may be substituted" represented by Z, is preferably a $C_{1-20}$ alkyl group that may be substituted for a $C_{1-6}$ alkoxy group, for instance.

Z is preferably an "acyl group" or a "hydrocarbon group that may be substituted"

Z is also preferably an aldehyde group (—CHO) or a derivative group thereof.

Here, the "derivative group" of "aldehyde" is a group that derives, or is derived from, an aldehyde group by an enzyme reaction etc. in vivo, or by an ordinary chemical reaction such as oxidation, reduction or removal, and is exemplified by those groups represented by the formula:

—COW or —C(OR$^c$)$_2$W wherein W represents a hydrogen atom, an azido, a lower alkyl group or a mono-, di- or tri-halogeno $C_{1-6}$ alkyl group; and $R^c$ represents a $C_{1-6}$ alkyl group, a $C_{7-20}$ aralkyl group or a $C_{2-7}$ alkylene group resulting from binding of two $R^c$ groups.

The "lower alkyl group" represented by W is exemplified by $C_{1-6}$ alkyl groups such as methyl, ethyl, propyl, isopropyl, butyl, isobutyl, sec-butyl, tert-butyl, pentyl, isopentyl, neopentyl, tert-pentyl, 1-ethylpropyl, hexyl and isohexyl.

The "mono-, di- or tri-halogeno $C_{1-6}$ alkyl group" represented by W is exemplified by chloromethyl, bromomethyl, fluoromethyl, dichloromethyl, trichloromethyl, trifluoromethyl and 2,2,2-trichloromethyl.

W is preferably a hydrogen atom, for instance.

The "$C_{1-6}$ aralkyl group" represented by $R^c$ is exemplified by methyl and ethyl; the "$C_{7-20}$ aralkyl group" is exemplified by benzyl, 1-naphthylmethyl and 2-naphthylmethyl; the "$C_{2-7}$ alkylene group resulting from binding of two $R^c$ groups" is exemplified by ethylene and propylene.

$R^c$ is preferably a methyl or benzyl group, for instance.

The "aldehyde or a derivative group thereof" represented by Z may bind to the C-terminal carboxyl group to form a cyclic structure represented by, for example, the formula:

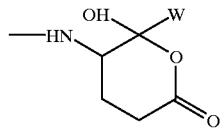

wherein the symbols have the same definitions as those given above.

With respect to formulas (I) and (I') above,

A represents

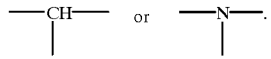

With respect to formulas (I) and (I') above, n represents 1 or 2.

Examplary esters of compounds represented by formulas (I) and (I') above include those used as synthesis intermediates for phenyl or benzyl esters that may be substituted by $C_{1-6}$ alkyl esters, nitro, $C_{1-6}$ alkoxy, $C_{1-6}$ alkoxycarbonyl etc., pharmacologically acceptable ones, and those that can turn to pharmacologically acceptable forms in vivo.

Here, the "$C_{1-6}$ alkyl ester" is exemplified by methyl esters, ethyl esters, propyl esters, isopropyl esters, butyl esters, isobutyl esters, sec-butyl esters, tert-butyl esters, pentyl esters, isopentyl esters, neopentyl esters, tert-pentyl esters, 1-ethylpropyl esters, hexyl esters and isohexyl esters.

The "$C_{1-6}$ alkoxy" is exemplified by methoxy, ethoxy, propoxy, isopropoxy, butoxy, isobutoxy, sec-butoxy, tert-butoxy, pentyloxy, isopentyloxy, tert-pentyloxy, neopentyloxy, hexyloxy, isohexyloxy, 1,1-dimethylbutoxy, 2,2-dimethylbutoxy and 3,3-dimethylbutoxy.

The "$C_{1-6}$ alkoxycarbonyl" is exemplified by methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl and tert-pentyloxycarbonyl.

The salt of the desired compound (I) or (I') of the present invention is preferably a pharmaceutically acceptable salt, exemplified by salts with inorganic bases, salts with organic bases, salts with inorganic acids, salts with organic acids and salts with basic or acidic amino acids. Preferable salts with inorganic bases include alkali metal salts such as sodium salt and potassium salt; alkaline earth metal salts such as calcium salt and magnesium salt; aluminum salt and ammonium salt. Preferable salts with organic bases include salts with trimethylamine, triethylamine, pyridine, picoline, ethanolamine, diethanolamine, triethanolamine, dicyclohexylamine and N,N'-dibenzylethylenediamine. Preferable salts with inorganic acids include salts with hydrochloric acid, hydrobromic acid, nitric acid, sulfuric acid and phosphoric acid. Preferable salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid and p-toluenesulfonic acid. Preferable salts with basic amino acids include salts with arginine, lysine and ornithine. Preferable salts with acidic amino acids include salts with aspartic acid and glutamic acid.

The above compound (I) or (I') include novel compounds (Ia), (Ib) and (Ic). The salts or esters of compounds (Ia), (Ib) and (Ic) are exemplified by the same salts or esters as above mentioned for the salts or esters of the compound (I) or (I').

With respect to formula (Ia), $R^{1a}$ represents an aralkyloxycarbonyl group.

The "aralkyloxycarbonyl group" represented by $R^{1a}$ is exemplified by the same "aralkyloxycarbonyl group" exemplified by preferable $R^1$.

$R^{1a}$ is preferably 9-fluorenylmethyloxycarbonyl, etc.

With respect to formulas (Ia), $R^{2a}$, $R^{3a}$ and $R^{4a}$, same or different, represent a bond, an amino acid residue or a group of the formula:

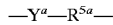

wherein $R^{5a}$ represents a group resulting from removing the imino group from an amino acid residue; and ya represents —O—, —S— or —$NR^{6a}$— in which $R^{6a}$ represents a hydrogen atom or lower alkyl groups having 1 to 6 carbon atoms.

The "amino acid residue" and "group represented by the formula —$Y^a$—$R^{5a}$—" represented by $R^{2a}$, $R^{3a}$ and $R^{4a}$ are exemplified by the same "amino acid residue" and "group represented by the formula —Y—$R^5$—" represented by $R^2$, $R^3$ and $R^4$ above.

The "group resulting from removing the imino group from an amino acid residue" represented by $R^{5a}$ is exemplified by "group resulting from removing the imino group from an amino acid residue" exemplified by $R^5$ above.

Here, the amino acid residue is preferably residue of amino acid which is selected from valine and aminoisobutyric acid, etc.

The "lower alkyl groups" represented by $R^{6a}$ is exemplified by "lower alkyl group" exemplified by $R^6$ above.

As for $R^{2a}$, $R^{3a}$ and $R^{4a}$, preferably, the one is a bond and the other two are, same or different, amino acid residues. These amino acid residue are preferably residues of amino acids which are selected from valine and aminoiso-butyric acid, etc.

With respect to formula (Ia), $Z^a$ represents an aldehyde group or an acetal group.

The "aldehyde or acetal group" represented by $Z^a$ is exemplified by the same group represented by the formula

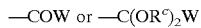

wherein the symbols have the same definitions as those gives above, exemplified by Z above.

$R^c$ is preferably methyl group, etc, and W is preferably hydrogen atom, etc. $Z^a$ is preferably aldehyde group, etc.

The compound (Ia) is preferably a compound, wherein $R^{1a}$ is an aralkyloxycarbonyl group, one of $R^{2a}$, $R^{3a}$ and $R^{4a}$ is a bond and the other two of those are residues of amino acids selected from valine and amino isobutyric acid, and $Z^a$ is an aldehyde group. As the compound (Ia), specifically, N-[N-(9-fluorenylmethyloxycarbonyl)-valylaminoisobutyl]-3-amino-4-oxobutanoic acid, N-{N-[N-(9-fluorenylmethyloxycarbonyl-valyl]-1-aminocyclohexanecarbonyl}-3-amino-4-oxobutanoic acid, N-{S-[N-(9-fluorenylmethyloxycarbonyl)-valyl]-2-mercaptopropionyl}-3-amino-4-oxobutanoic acid and their salts are more preferable.

With respect to formula (Ib), $R^{1b}$ represents an aralkyloxycarbonyl group, a cycloalkylcarbonyl group, a heterocyclic carbonyl group, an arylcarbonyl group which may be substituted by hydroxyl, carboxyl or benzyloxycarbonyl, an arylsulfonyl group which may be substituted by hydroxyl.

The "aralkyloxycarbonyl group" or the "arylcarbonyl group" is exemplified by the same "aralkyloxycarbonyl group" or "arylcarbonyl group" exemplified by preferably $R^1$ above.

The "cycloalkylcarbonyl group" represented by $R^{1b}$ include cycloalkylcarbonyl groups having 3 to 20 carbon atoms, such as cyclopropylcarbonyl, cyclobutylcarbonyl, cyclopentylcarbonyl, cyclohexylcarbonyl, cycloheptylcarbonyl, cyclooctylcarbonyl, bicyclo[2.2.1]heptylcarbonyl, bicyclo[2.2.2]octylcarbonyl, bicyclo[3.2.1]octylcarbonyl, bicyclo[3.2.2]nonylcarbonyl, bicyclo[3.3.1]nonylcarbonyl, bicyclo[4.2.1]nonylcarbonyl, bicyclo[4.3.1]decylcarbonyl and adamantylcarbonyl.

The "arylsulfonyl group" represented by $R^{1b}$ include arylsulfonyl groups having 6 to 20 carbon atoms, such as phenylsulfonyl, naphthylsulfonyl, anthrylsulfonyl, phenanthrylsulfonyl, acenaphthylenylsulfonyl and fluorenylsulfonyl.

The "heterocycle" of "heterocyclic carbonyl group" represented by $R^{1b}$ is exemplified by the same "heterocyclic group" exemplified by $R^1$ above.

$R^{1b}$ is preferably an aralkyloxycarbonyl group or an arylcarbonyl group, more preferably 9-fluorenylmethyloxycarbonyl or 2-naphthylcarbonyl.

With respect to formulas (Ib), $R^{2b}$, $R^{3b}$ and $R^{4b}$, same or different, represent a bond an amino acid residue or a group of the formula:

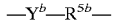

wherein $R^{5b}$ represents a group resulting from removing the imino group from an amino acid residue; and $Y^b$ represents —O—, —S— or $NR^{6b}$— in which $R^{6b}$ represents a hydrogen atom or lower alkyl groups having 1 to 6 carbon atoms.

The "amino acid residue" and "group represented by the formula —$Y^b$—$R^{5b}$—" represented by $R^{2b}$, $R^{3b}$ and $R^{4b}$ are exemplified by the same "amino acid residue" and "group represented by the formula —Y—$R^5$—" represented by $R^2$, $R^3$ and $R^4$ above.

The "group resulting from removing the imino group from an amino acid residue" represented by $R^{5b}$ is exemplified by "group resulting from removing the imino group from an amino acid residue" exemplified by $R^5$ above.

Here, the amino acid residue is preferably residue of amino acid which is selected from valine, proline, alanine and glutamic acid, etc.

The "lower alkyl groups" represented by $R^{6b}$ is exemplified by "lower alkyl group" exemplified by $R^6$ above.

$R^{2b}$, $R^{3b}$ and $R^{4b}$ are preferably, the one is a bond and the other two are, same or different, amino acid residues. These amino acid residues are preferably residues of amino acids which are selected from valine, proline, alanine and glutamic acid, etc.

With respect to formula (Ib), $Z^b$ represents an aldehyde group, an acetal group, an acylalkylcarbonyl group or a substituted alkenyl group.

The "aldehyde or acetal group" represented by $Z^b$ is exemplified by the same group represented by the formula —COW or —C(OR$^c$)$_2$W wherein the symbols have the same definitions as those given above, exemplified by Z above. $R^c$ is preferably methyl group, etc, and W is preferably hydrogen atom, etc. $Z^b$ is preferably aldehyde group, etc.

The "alkenyl group" of the "substituted alkenyl group" is exemplified by the same "alkenyl group" exemplified by the "hydrocarbon group" represented by $R^1$ above, vinyl, etc. is preferable.

The substituents of the "substituted alkenyl group" represented by $Z^b$ are exemplified by arylsulfonyl, alkylsulfonyl, arylsulfonyl, alkylcarbonyl, etc.

The "arylsulfonyl" or "arylcarbonyl" is exemplified by the same "arylsulfonyl" or "arylcarbonyl" exemplified by $R^{1b}$, phenylsulfonyl, phenylcarbonyl, etc. are preferable.

The "alkylsulfonyl groups" include alkyl groups having 1 to 20 carbon atoms, such as methylsulfonyl, ethylsulfonyl, propylsulfonyl, isopropylsulfonyl, butylsulfonyl, isobutylsulfonyl, sec-butylsulfonyl, tert-butylsulfonyl, pentylsulfonyl, isopentylsulfonyl, neopentylsulfonyl, tert-pentylsulfonyl, 1-ethylpropylsulfonyl, hexylsulfonyl, isohexylsulfonyl, heptylsulfonyl, octylsulfonyl, decylsulfonyl, dodecylsulfonyl, tridecylsulfonyl, tetradecylsulfonyl, hexadecylsulfonyl, octadecylsulfonyl, nonadecylsulfonyl and eicosanylsulfonyl, preferably propylsulfonyl, etc.

The "alkylcarbonyl groups" include alkyl groups having 1 to 20 carbon atoms, such as acetylcarbonyl, ethylcarbonyl, propylcarbonyl, isopropylcarbonyl, butylcarbonyl, isobutylcarbonyl, sec-butylcarbonyl, tert-butylcarbonyl, pentylcarbonyl, isopentylcarbonyl, neopentylcarbonyl, tert-pentylcarbonyl, 1-ethylpropylcarbonyl, hexylcarbonyl, isohexylcarbonyl, heptylcarbonyl, octylcarbonyl, decylcarbonyl, dodecylcarbonyl, tridecylcarbonyl, tetradecylcarbonyl, hexadecylcarbonyl, octadecylcarbonyl, nonadecylcarbonyl and eicosanylcarbonyl, preferably methylcarbonyl, etc.

The "acyl" group of the "acylalkylcarbonyl group" represented by $Z^b$ is exemplified by the same "acyl group" exemplified by Z above.

The "alkyl" group of the "acylalkylcarbonyl group" represented by $Z^b$ is exemplified by the same "alkyl" exemplified by "hydrocarbon ogroup" of "hydrocarbon group that may be substituted for" represented by $R^7$, $R^8$, $R^9$ and $R^{10}$ above.

As the "acylalkylcarbonyl group" represented by $Z^b$, arycarbonyloxycarbonyl groups which may be substituted by halogen atoms (e.g. chloro), etc. are preferable.

As $Z^b$, aldehyde group or acylalkylcarbonyl group is preferable, aldehyde group or 2,6-dichlorobenzoyloxymethylcarbonyl group is more preferable.

The compound (Ib) is preferably a compound, wherein $R^{1b}$ is aralkyloxycarbonyl or arylcarbonyl, one of $R^{2b}$, $R^{3b}$ and $R^{4b}$ is a bond and the other two are residues of amino acids selected from valine, proline, alamine and glutamic acid, and $Z^b$ is aldehyde or arylcarbonyloxycarbonyl which may be substituted by halogen atoms.

As the compound (Ib), specifically,

N-[N-(2-naphthoyl)-valyl-alanyl]-4-amino-5-oxopentanoic acid,

N-[N-(9-fluorenylmethyloxycarbonyl)-valyl-alanyl]-4-amino-5-oxo)pentanoic acid,

N-[N-(2-naphthoyl)-valyl-alanyl]-4-amino-5-oxo-6-(2,6-dichlorobenzoyloxy)hexanoic acid, N-[N-(2-naphthoyl)-glutamyl-alanyl]-4-amino-5-oxopentanoic acid, N-[N-(2-naphthoyl)-valyl-prolyl]-4-amino-5-oxopentanoic acid, N-{N-[N-(9-fluorenylmethyloxycarbonyl)-valyl]-1-aminocyclohexanecarbonyl}-4-amino-5-oxopentanoic acid, and their salts is are most preferable.

With respect to formula (Ic), $R^{1c}$ represents an aralkyloxycarbonyl group or an arylcarbonyl group.

The "aralkyloxycarbonyl group" or "arylcarbonyl group" represented by $R^{1c}$ is exemplified by the same "aralkyloxycarbonyl group" or "arylcarbonyl group" exemplified by preferable $R^1$ above, arylcarbonyl group, etc. is preferable.

As $R^{1c}$, specifically, 9-fluorenylmethyloxycarbonyl, 2-naphthylcarbonyl, etc. are preferable, and 2-naphthylcarbonyl is more preferable.

With respect to formula (Ic), $R^{2c}$, $R^{3c}$ and $R^{4c}$, same or different, represent a bond, an amino acid residue or a group of the formula:

—Y$^c$—R$^{5c}$— wherein $R^{5c}$ represents a group resulting from removing the imino group from an amino acid residue; Yc represents —O—, —S— or —NR$^{6c}$— in which $R^{6c}$ represents a hydrogen atom or lower alkyl groups having 1 to 6 carbon atoms.

The "amino acid residue" and "group represented by the formula —Y$^c$—R$^{5c}$—" represented by $R^{2c}$, $R^{3c}$ and $R^{4c}$ are exemplified by the same "amino acid residue" and "group represented by the formula —Y—R$^5$—" represented by $R^2$, $R^3$ and $R^4$ above.

The "group resulting from removing the imino group from an amino acid residue" represented by $R^{5c}$ is exemplified by "group resulting from removing the imino group from an amino acid residue" exemplified by $R^5$ above.

Here, the amino acid residue is preferably residue of amino acid which is selected from valine, alanine and aminoisobutyric acid, etc.

The "lower alkyl groups" represented by $R^{6c}$ is exemplified by "lower alkyl group" exemplified by $R^6$ above.

$R^{2c}$, $R^{3c}$ and $R^{4c}$ are preferably, the one is a bond and the other two are, same or different, amino acid residue. These amino acid residues are preferably residues of amino acids wahich are selected from valine, alanine and aminoisobutyric acid, etc.

With respect to formula (Ic), $Z^c$ represents an aldehyde group, an acetal group, a substituted carbonyl group or a substituted alkenyl group. As $Z^c$, an aldehyde group, a substituted carbonyl group or a substituted alkenyl group is preferable, and substituted carbonyl group or a substituted alkenyl group is more preferable.

The "aldehyde or acetal group" represented by $Z^c$ is exemplified by the same group represented by the formula —COW— or —C(OR$^c$)$_2$W wherein the symbols have the same definitions as those gives above, exemplified by Z above.

R$^c$ is preferably methyl group, etc, and W is preferably hydrogen atom, etc. Z$^c$ is preferably aldehyde group, etc.

The substituents of "substituted carbonyl group" or "substituted alkenyl group" represented by Z$^c$ are exemplified by "optionally substituted hydrocarbon group", the said "optionally substituted hydrocarbon group" is exemplified by the same "optionally substituted hydrocarbon group" represented by Z above.

As the "substituted alkenyl group" represented by Z$^c$, alkenyl groups (e.g. C$_{2-20}$ alkenyl such as vinyl, etc.) which are substituted by aryl groups (e.g. C$_{6-20}$ aryl such as phenyl, etc.) are preferable.

The "substituted carbonyl group" represented by Z$^c$ is exemplified by alkylcarbonyl group or alkenylcarbonyl group which may be substituted by halogen atom (e.g. chloro, fluoro, bromo), oxo, alkoxy (e.g. C$_{1-6}$ alkoxy such as methoxy, ethoxy, etc), aryl or acyl, preferably acyloxyalkylcarbonyl group, or alkylcarbonyl group which may be substituted by halogen atom, more preferably chloromethylcarbonyl or diphenylphosphynyloxyacetyl, etc.

The "alkyl" of the "alkylcarbonyl" and the "alkenyl" of the "alkenylcarbonyl" exemplified by the "substituted carbonyl group" represented by Z$^c$ are exemplified by the same "alkyl" and "alkenyl" exemplified by "hydrocarbon group" of "an optionally substituted hydrocarbon group" represented by Z above.

The "aryl" and "acyl" of the substituents of "alkylcarbonyl" and "alkenylcarbonyl" exemplified by "substituted carbonyl group" represented by Z$^c$ are exemplified by the same "aryl" exemplified by "hydrocarbon group" of "an optionally substituted hydrocarbon group" represented by Z above and "acyl" represented by Z above.

As for the compound (Ic), specifically,

N'-[N-(2-naphthoyl)-valyl-alanyl]-N-(2-carboxyethyl)-chloroacetohydrazide,

N'-[N-(2-naphthoyl)-valyl-alanyl]-N-(2-carboxyethyl)-diphenylphosphynyloxyacetohydrazide, and their salts are preferable.

The compound (I) or (I') of the present invention is described below and is produced using the method exemplified in Examples.

The compound (I) or (I') is produced using the method described below.

(A) In the case where A is,

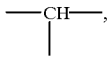

a compound of the formula (Id):

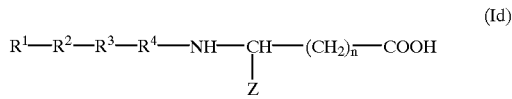

can be produced as follows:
(1) It can be produced by reacting a compound of the formula (II):

 (II)

wherein Q$^a$ represents a hydrogen atom or a carboxyl-protecting group, the other symbols have same definitions as those given above, or a salt thereof, with removing the carboxyl group-protecting group if necessary, or activating carboxylic acid if necessary, with a compound of the formula (III):

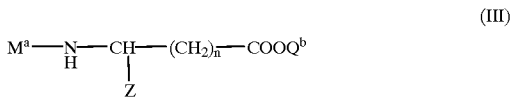 (III)

wherein M$^a$ represents a hydrogen atom or an amino protecting group, Q$^b$ represents a hydrogen atom or a carboxyl-protecting group, the other symbols have the same definitions as those given above, or a salt thereof, with removing the amino-protecting group if necessary before the reaction, then removing the carboxyl-protecting group represented by Q$^b$ if necessary after the reaction.

In the above reaction (1), useful methods of activating acid components, such as carboxylic acid, in the above-described reaction include the acid halid method, the azide method, the mixed acid anhydride method (isobutyloxycarbonyl chloride, pivalic chloride, or the like, is used as "another acid"), the symmetric acid anhydride method, the method using a condensing agent such as N,N'-carbodiimidazole, N,N'-dicyclohexylcarbodiimide, N,N'-diisopropylcarbodiimide, 1-ethyl-3-(3-dimethylaminopropyl)carbodiimide, N-ethoxycarbonyl-2-ethoxy-1,2-dihydroquinoline, diethyl phosphorocyanidate, diphenyl phosphorylazide, 2-(1H-benzotriazol-1-yl)-1,1,3,3-tetramethyluronium tetrafluoroborate, 2-(1 H-benzotriazol-1-yl)-1,1,3,3-tetramethyluronium hexafluorophosphate, benzotriazol-1-yl-oxy-tris (dimethylamino)phosphonium hexafluorophosphate, benzotriazol-1-yl-oxy-tris-pyrrolidino-phosphonium hexafluorophosphate, bromo-tris-pyrrolidino-phosphonium hexafluorophosphate, 2-(5-norbornene-2,3-dicarboxyimide)-tetramethyluronium tetrafluoroborate, or the like, the method wherein one of the above condensing agents is reacted in the presence of 4-dimethylaminopyridine, 3-hydroxy-3,4-dihydro-4-oxo-1, 2,3-benzotriazole, N-hydroxy succinimide, N-hydroxy-5-norbornene-2,3-dicarboxyimide, 1-hydroxybenzotriazole, or the like, and the activated ester method using one of these substances.

The above synthesis reaction (1) is normally carried out in a solvent, using compound (III) 0.5 to 10 mol equivalent to compound (II). Useful solvents include aromatic hydrocarbons such as benzene, toluene and xylene, halogenated hydrocarbons such as dichloromethane and chloroform, saturated hydrocarbons such as hexane, heptane and cyclohexane, ethers such as diethyl ether, tetrahydrofuran and dioxane, nitriles such as acetonitrile, sulfoxides such as dimethyl sulfoxide, acid amides such as N,N-dimethylformamide and esters such as ethyl acetate. These solvents may be used alone, or in combination of two or more kinds at an appropriate ratio, such as from 1:1 to 1:10. Reaction temperature is normally about −80 to 100° C., preferably about −50 to 50° C. Reaction time is normally about 1 to 96 hours, preferably about 1 to 72 hours.

With respect to the above reaction (1), in the case where the compound has the other functional groups (e.g. hydroxyl group, carboxyl group, amino group) besides protecting group represented by Q$^b$, it is protected as necessary and the protecting-group removed after the reaction. After the reaction, the product can be separated or purified by the known means.

(2) In the above reaction (1), compound (II) can be produced, using compounds of formulas:

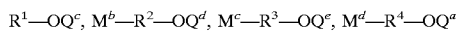

wherein $M^b$, $M^c$ and $M^d$, same or different, represent a hydrogen atom or protecting groups of amino group, hydroxyl group or thiol group; $Q^a$, $Q^c$, $Q^d$ and $Q^e$, same or different, represent hydrogen atom, protecting group of carboxylic acid, by sequentially binding them in the above method (1).

(3) In the above reaction (1), compound (III) can be produced using the method below.

(a) In the case where Z is an aldehyde group or the derivative thereof, a compound of formula (IIIa);

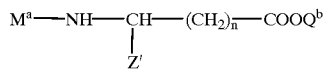
(IIIa)

wherein Z' represents an aldehyde group or the derivative thereof, the other symbols have the same definitions as those given above, or salt thereof, is produced by oxidizing a compound of formula (IV);

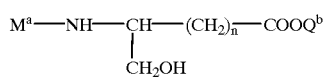
(IV)

wherein the symbols have the same definitions as those given above, or salt thereof.

Here, the "aldehyde group or the derivative thereof" represented by Z' is exemplified by the "aldehyde group or the derivative thereof" exemplified by Z above.

The above oxidizing reaction can be achieved by, for example, Jones oxidation using chromium oxide-sulfuric acid-pyridine, Collins oxidation using chromium oxidepyridine complex, chromic acid oxidation with pyridium chlorochromate, oxidation with activated dimethyl sulfoxide (DMSO) or oxidation with oxyammonium salt. Preferably, the reaction is effected by oxidation with activated DMSO. Activated DMSO oxidation is normally carried out in a solvent in the presence of both DMSO and an electrophilic reagent, in the presence of a base if necessary. Useful electrophilic reagents include dicyclohexylcarbodiimide, acetic anhydride, phosphorus pentoxide, chlorine and sulfur trioxide-pyridine complex. Useful bases include organic bases such as trimethylamine, triethylamine, diisopropylethylamine, pyridine, picoline, N-methylpyrrolidine, piperidine, N-methylpiperidine, N-methylmorpholine, 1,5-diazacyclo[4.3.0]non-5-ene, 1,4-diazabicyclo[2.2.2]octane, 1,8-diazabicyclo[5.4.0]-7-undecene. When sulfur trioxide-pyridine complex, for instance, is used, its amount is normally about 1 to 100 mol equivalents, preferably about 1 to 50 mol equivalents of trioxide-pyridine complex, and, about 1 to 100 mol equivalents, preferably about 1 to 50 mol equivalents of triethylamine as base per mol equivalent of compound (IV). DMSO itself may serve as a solvent, but solvents inert to the reaction may be used, including halogenated hydrocarbons such as chloroform, dichloromethane and 1,2-dichloroethane, ethers such as ethyl ether, tetrahydrofuran, dioxane and dimethoxyethane, esters such as ethyl acetate, hydrocarbons such as benzene and toluene, amides such as and N,N-dimethylformamide, and nitriles such as acetonitrile, amines such as pyridine . Reaction temperature is normally about −70 to 100° C., preferably about −20 to 50° C. Reaction time is normally about 0.5 to 72 hours, preferably about 0.5 to 24 hours.

The aldehyde obtained in the above reaction, being protected by acetal, etc., can be used in the above reaction (1). Acetals include dimethylacetal, diethylacetal, dimethylthioacetal, and cyclic acetal such as 1,3-dioxane, 1,3-dithiorane, etc.

In the case where acetal is dimethylacetal, it can be produced, disolving aldehyde in methanol or in combination of methanol and the other solvent (e.g. ethers such as tetrahydrofuran), in the presence of 0.01 to 0.2 mol equivalent of acid such as paratoluene acid, chloridehydrogen, to aldehyde, together with 1 to 200 mole equivalent, preferably 5 to 100 mole equivalent, of trimethyl orthoformate or tetramethoxysilan to aldehyde if necessary. The aldehyde obtained in the above reaction can be converted to imido by reacting appropriate primary amines.

(b) In the case where Z is, an optionally hydrocarbon group, an acyl group except for Z', or a hydrogen atom, a compound of formula (IIIb);

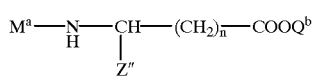
(IIIb)

wherein Z" is a hydrogen atom, an optionally hydrocarbon group, an acyl group except for Z, the other symbols have the same definitions as those given above, or salt thereof, can be produced using the following procedure.

It can be produced using aldehyde represented by Z' of compound (IIIa) obtained in the above (a) by Wittig reaction.

Also, a compound of formula (V);

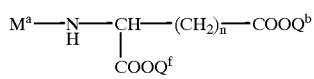
(V)

wherein $Q^f$ represents a lower alkyl group such as methyl, ethyl, the other symbols have the same definitions as those given above, or salt thereof, is reacted with alkyl anion of formula (VI);

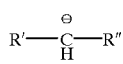
(VI)

wherein R' represents a hydrogen atom or an optionally substituted hydrocarbon group, R" represents an acyl group, to produce a compound of formula (IIIb-1);

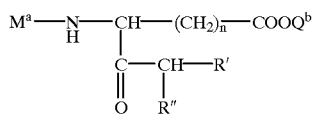
(IIIb-1)

wherein the symbols have the same definitions as those given above. Further, a compound of formula (IIIb-2);

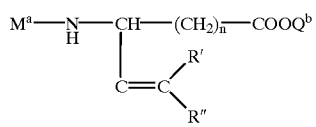
(IIIb-2)

wherein the symbols have the same definitions as those given above, is produced by reducing carbonyl group, introduced in the formula (IIIb-1), to alcohol and dehydrating it.

Further, carboxylic acid of a compound of formula

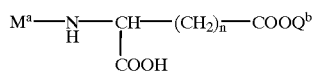
(VII)

wherein the symbols have the same definitions as those given above, being activated by the mixed acid anhydride method, or reacted with diazomethane, is treated with hydrogen halide, to produce a compound of formula (IIIb-3);

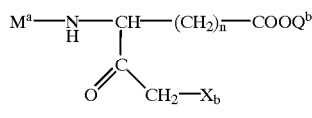
(IIIb-3)

wherein $X_b$ represents halogen atom such as chloro, bromo, etc., and the other symbols have the same definitions as those given above. Also, a compound of formula (IIIb-3) is reacted with R'''—COOH in the presence of a base, to produce a compound of formula (IIIb-4);

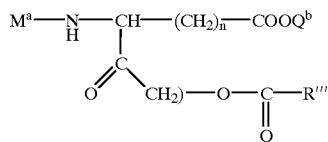
(IIIb-4)

wherein R''' represents an optionally substituted hydrocarbon group or heterocyclic group, and the other symbols have the same definitions as those given above.

The above reaction is normally carried out in a solvent in the presence of a base. Useful solvents include halogenated hydrocarbons such as chloroform, dichloromethane and 1,2-dichloroethane, ethers such as ethyl ether, tetrahydrofuran, dioxane and dimethoxyethane, esters such as ethyl acetate, hydrocarbons such as benzene and toluene, and amides such as pyridine and N,N-dimethylformamide. Useful bases include organic bases (e.g., alkylamines such as triethylamine, cyclic amines such as N-methylmorpholine and pyridine, aromatic amines such as N,N-dimethylaniline and N,N-diethylaniline) and inorganic bases (e.g., alkali metal carbonates such as sodium carbonate and potassium carbonate, alkali metal hydrogen carbonates such as sodium hydrogen carbonate and potassium hydrogen carbonate, alkali metal fluorides such as sodium fluoride and potassium fluoride). The amount of base used is normally about 1 to 10 mol equivalents, preferably about 1 to 5 mol equivalents per mol equivalent of compound (IIIb-3). Reaction time is normally about 1 to 72 hours, preferably about 1 to 24 hours.

Reaction temperature is normally about −10 to 150° C., preferably about 0 to 100° C.

These compound (IIIb-1) to (IIIb-4) are included in the compound (IIIb). Also, the compound (IIIb-3) is condensed with alcohols or compounds having sulfhydryl group, to produce the compound (IIIb) having ether linkage or thio-ether linkage. The thioether compound is oxidized to obtain the compound (IIIb) having sulfoxide group or sulfone group.

Here, the "an optionally hydrocarbon group" represented by R', "acyl group" represented by R'' and "an optionally hydrocarbon group on heterocyclic group" represented by R''' are exemplified by the same "hydrocarbon group that may be substituted", "heterocyclic group that may be substituted" and "acyl group" exemplified by $R^1$, $R^7$, $R^8$ and $R^9$ above.

(4) The compound (Id) can be produced by condensing the compound (II) and the compound (IV), or, the compound (V) and the compound (VII), by the above reaction (1), conducting alchols or —$COOQ^f$, —COOH to a variety of Z group, by the above reaction (3), the removing the protecting group as necessary, followed by purification as necessary.

(B) In the case where A is;

(1) A compound represented by formula (Ie):

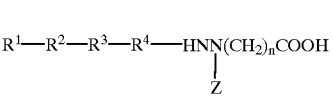
(Ie)

wherein symbols have the same definitions as those given above; an ester thereof or a salt thereof (hereinafter also referred to as compound (Ie)), can be produced by condensing the imino group of a compound represented by formula (VIII):

$$R^1—R^2—R^3—R^4—NHNH(CH_2)_nCOOQ^g \qquad (VIII)$$

wherein $Q^g$ represents a hydrogen atom or a protecting group of carboxylic acid, and the other symbols have the same definitions as those given above; an ester thereof or a salt thereof (hereinafter also referred to as compound (VIII)), by one of the above-mentioned methods, e.g., the acid halide method, with, for example, a compound represented by formula (IX):

(IX)

wherein $X^c$ represents a hydroxyl group or a halogen atom; the other symbols have the same definitions as those given above; an ester thereof or a salt thereof (hereinafter also referred to as compound (IX)), then removing the protecting group by one of the above-mentioned methods, followed by purification if necessary.

Compound (Ic) can also be produced-by condensing a monohalogenated acetic acid, as compound (IX), with compound (VIII) to yield a compound of formula (X);

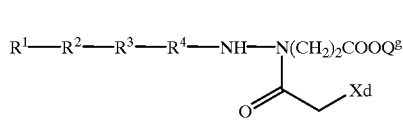

(X)

wherein $X^d$ represents a halogen atom, and the other symbols have the same definitions as those given above, replacing the halogen of compound (X) with an acid, then removing the protecting group by one of the above-mentioned methods, followed by purification if necessary. Useful acids include phosphinic acid, phosphonic acid, carboxylic acid, sulfinic acid, sulfonic acid and phenols. The reaction for replacing the halogen of compound (X) with an acid is normally carried out in a solvent in the presence of a base. Useful solvents include halogenated hydrocarbons such as chloroform, dichloromethane and 1,2-dichloroethane, ethers such as ethyl ether, tetrahydrofuran, dioxane and dimethoxyethane, esters such as ethyl acetate, hydrocarbons such as benzene and toluene, and amides such as pyridine and N,N-dimethylformamide. Useful bases include organic bases (e.g., alkylamines such as triethylamine, cyclic amines such as N-methylmorpholine and pyridine, aromatic amines such as N,N-dimethylaniline and N,N-diethylaniline) and inorganic bases (e.g., alkali metal carbonates such as sodium carbonate and potassium carbonate, alkali metal hydrogen carbonates such as sodium hydrogen carbonate and potassium hydrogen carbonate, alkali metal fluorides such as sodium fluoride and potassium fluoride). The amount of base used is normally about 1 to 10 mol equivalents, preferably about 1 to 5 mol equivalents per mol equivalent of compound (X). Reaction time is normally about 1 to 72 hours, preferably about 1 to 24 hours. Reaction temperature is normally about −10 to 150° C., preferably about 0 to 100° C.

(2) The compound (VIII) in the above (B)-(1), can be produced by using a compound of formula (XI);

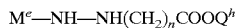

(XI)

wherein $M^e$ represents a hydrogen atom or a n amino-protecting group, $Q^h$ represents a hydrogen atom or a carboxyl-protecting group, the other symbols have the same definitions as those given above, or an ester or salt thereof (hereinafter also referred to as compound (XI)) and the compound (II), by the above-mentioned (1) of (A)-(1).

(3) Compound (XI) can, for example, be produced by adding a hydrazine or a hydrazide having one amino group protected by a protecting group to an acrylate, then removing the amino-protecting group by the above-mentioned method, followed by purification if necessary. In this case, the amino protecting group may be one of the above-mentioned protecting groups. For this reaction, the acrylate itself may serve as a solvent, but alcohols such as ethanol, propanol and tert-butanol, halogenated hydrocarbons such as chloroform, dichloromethane and 1,2-dichloroethane, ethers such as ethyl ether, tetrahydrofuran, dioxane and dimethoxyethane, esters such as ethyl acetate, hydrocarbons such as benzene and toluene, amides such as N,N-dimethylformamide, amines such as pyridine, etc. may be used as solvents. The reaction is accelerated by heating to about 50 to 200° C., preferably about 50 to 100° C.

(4) The compound (Ie) can be produced by, after conducting a compound of formula (XII);

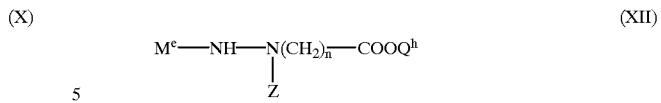

(XII)

wherein the symbols have the same definitions as those given above (hereinafter also referred to as compound (XII) by using the compound (XI) and the compound (IX) by the above-mentioned method (B)-(1), by using the compound (XII) and the compound (II) by the above-mentioned method (A)-(1).

The compound of the present invention can be produced using the following method described below.

With respect to general formula (I) above, it is possible to activate the carboxylic acid corresponding to $R^5$, that may have other functional groups protected with an appropriate protecting groups, and condensing it with an amine or thiol compound that may have other functional groups appropriately protected, whether the units represented by $R^1$, $R^2$, $R^3$ and $R^4$ are bound via amide bonds or carboxyl-ic acid thio ester bonds. If necessary, the condensing reaction may be followed by partial removal of the protective group and/or a purification process prior to the similar condensing reaction that follows. When the resulting final condensation product is given as a protected compound, the desired product can be obtained in pure form by removing all protecting groups, followed by purification if necessary.

The compound of the present invention is also produced using , the following method described below and exemplified in Example.

With respect to general formula (I) above, it is possible to activate the carboxylic acid corresponding to $R^5$, that may have other functional group(s) protected with an appropriate protecting group(s), and condensing it with an amine or alcohol compound that may have protected by other functional group(s) appropriately protected, whether the units represented by $R^1$, $R^2$, $R^3$ and $R^4$ are bound via amide bonds or ester bonds. If necessary, the condensing reaction may be followed by partial removal of the protecting group and/or a purification process prior to a similar condensing reaction that follows. When the resulting final condensation product is given as a protected compound, the desired product can be obtained in pure form by removing all protecting groups, followed by purification if necessary.

The compound (I) or (I') of the present invention is produced using the method described below, the following method and exemplified in Example.

With respect to formulas (I) and (I') above, a compound represented by formula (If):

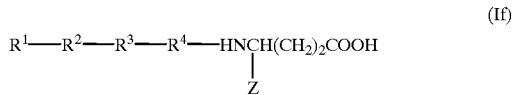

(If)

wherein the symbols have the same definitions as those given above, an ester thereof or a salt thereof (hereinafter also referred to as compound (If)), can be produced by sequentially binding $R^1$, $R^2$, $R^3$, $R^4$, each of which may be protected, and a compound represented by formula (IIf):

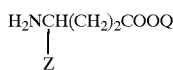
(IIf)

wherein Q represents a hydrogen atom or a carboxyl protecting group; the other symbols have the same definitions as those given above, an ester thereof or a salt thereof (hereinafter also referred to as compound (IIf)), in any order, then removing the protecting group, followed by purification if necessary. Binding of these units, whether via amide bonds, ester bonds or carboxylic acid thio ester bonds, can be achieved by activating the carboxylic acid etc. of the group corresponding to $R^5$, which may have other functional group(s) protected with an appropriate protecting group(s), and condensing it with an amine, alcohol or thiol compound that may have other functional groups appropriately protected. If necessary, the condensing reaction may be followed by partial removal of the protective group and/or a purification process prior to a similar condensing reaction that follows.

Useful methods of activating acid components, such as carboxylic acid, in the above-described reaction are exemplified by the same methods of activating carboxylic acid in the above reaction (1).

The above synthetic reaction is normally carried out in a solvent. Useful solvents include aromatic hydrocarbons such as benzene, toluene and xylene, halogenated hydrocarbons such as dichloromethane and chloroform, saturated hydrocarbons such as hexane, heptane and cyclohexane, ethers such as diethyl ether, tetrahydrofuran and dioxane, nitriles such as acetonitrile, sulfoxides such as dimethyl sulfoxide, acid amides such as N,N-dimethylformamide and esters such as ethyl acetate. These solvents may be used alone, or in combination of two or more kinds at an appropriate ratio, such as from 1:1 to 1:10. Reaction temperature is normally about −80 to 100° C., preferably about −50 to 50° C. Reaction time is normally about 1 to 96 hours, preferably about 1 to 72 hours.

Compound (IIf) represented by the formula:

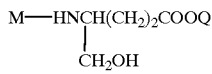
(IIIf)

wherein M represents a hydrogen atom or an amino protecting group; the other symbols have the same definitions as those given above; an ester thereof or a salt thereof (hereinafter also referred to as compound (IIIf)), can be produced to yield an aldehyde, which may be protected by acetal etc.

Compound (If) can also be produced by sequentially binding compounds corresponding to $R^1$, $R^2$, $R^3$ and $R^4$, each of which may be protected, and compound (IIIf) having its amino-protecting group removed, in any order, then removing the protecting group, followed by purification as necessary, and oxidizing the alcohol, followed by purification as necessary. Compound (If) can also be produced by sequential binding $R^1$, $R^2$, $R^3$, $R^4$, each of which may be protected, and compound (IIIf), in any order, then oxidizing the alcohol to remove the protecting group, followed by purification if necessary.

This oxidizing reaction can be achieved by, for example, Jones oxidation using chromium oxide-sulfuric acidpyridine, Collins oxidation using chromium oxide-pyridine complex, chromic acid oxidation with pyridium chlorochromate, oxidation with activated dimethyl sulfoxide (DMSO) or oxidation with oxyammonium salt. The reaction is effected by oxidation with activated DMSO. Activated DMSO oxidation is normally carried out in a solvent in the presence of both DMSO and an electrophilic reagent. Useful electrophilic reagents include dicyclohexylcarbodiimide, acetic anhydride, phosphorus pentoxide, chlorine and sulfur trioxide-pyridine complex. When sulfur trioxide-pyridine complex, for instance, is used, its amount is normally about 1 to 10 mol equivalents, preferably about 1 to 5 mol equivalents, per mol equivalent of triethylamine and compound (IIIf). DMSO itself may serve as a solvent, but solvents inert to the reaction may be used, including halogenated hydrocarbons such as chloroform, dichloromethane and 1,2-dichloroethane, ethers such as ethyl ether, tetrahydrofuran, dioxane and dimethoxyethane, esters such as ethyl acetate, hydrocarbons such as benzene and toluene, amides such as N,N-dimethylformamide, amines such as pyridine, and nitriles such as acetonitrile. Reaction temperature is normally about −70 to 100° C., preferably about −20 to 50° C. Reaction time is normally about 0.5 to 72 hours, preferably about 0.5 to 24 hours.

A compound represented by formula (Ig):

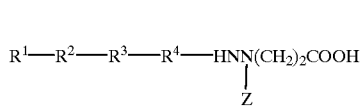
(Ig)

wherein the symbols have the same definitions as those given above; an ester thereof or a salt thereof (hereinafter also referred to as compound (Ig)), can be produced by condensing the imino group of a compound represented by formula (IVg):

$$R^1-R^2-R^3-R^4-NHNH(CH_2)_2COOQ \quad (IVg)$$

wherein the symbols have the same definitions as those given above; an ester thereof or a salt thereof (hereinafter also referred to as compound (IVg)), by one of the above-mentioned methods, e.g., the acid halide method, using, for example, a compound represented by formula (Vg):

$$Z-X^g \quad (Vg)$$

wherein $X^g$ represents a hydroxyl group or a halogen atom; the other symbol has the same definitions as those given above; an ester thereof or a salt thereof (hereinafter also referred to as compound (Vg)), then removing the protecting group by one of the above-mentioned methods, followed by purification if necessary.

Compound (Ig) can also be produced by condensing a monohalogenated acetic acid, as compound (Vg), with compound (IVg) to yield compound (Ig), replacing the halogen of compound (Ig) with an acid, then removing the protecting group by one of the above-mentioned methods, followed by purification as necessary. Useful acids include phosphinic acid, phosphonic acid, carboxylic acid, sulfinic acid, sulfonic acid and phenols. The reaction for replacing the halogen of compound (Ig) with an acid is normally carried out in a solvent in the presence of a base. Useful solvents include halogenated hydrocarbons such as chloroform, dichloromethane and 1,2-dichloroethane, ethers such as ethyl ether, tetrahydrofuran, dioxane and dimethoxyethane, esters such as ethyl acetate, hydrocarbons such as benzene and toluene, and amides such as N,N-dimethylformamide, and amines such as pyridine. Useful bases include organic bases (e.g., alkylamines such as triethylamine, cyclic amines such as N-methylmorpholine and pyridine, aromatic amines such as N,N-dimethylaniline and N,N-diethylaniline) and inorganic bases (e.g., alkali metal carbonates such as sodium carbonate and potassium carbonate, alkali metal hydrogen carbonates such as sodium hydrogen carbonate and potassium hydrogen carbonate, alkali metal fluorides such as sodium fluoride and potassium fluoride). The amount of base used is normally about 1 to 10 mol equivalents, preferably about 1 to 5 mol equivalents per mol equivalent of compound (VIg). Reaction time is normally about 1 to 72 hours, preferably about 1 to 24 hours. Reaction temperature is normally about −10 to 150° C., preferably about 0 to 100° C.

Compound (Ig) can also be produced as follows: Specifically, it can be produced by binding a compound represented by formula (IIg):

  (IIg)

wherein symbols have the same definitions as those given above, having its amino group protected by a protecting group, an ester thereof or a salt thereof (hereinafter also referred to as compound (IIg)), after being converted to a compound represented by formula (VIIg):

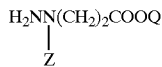  (VIIg)

wherein symbols have the same definitions as those given above (hereinafter also referred to as compound (VIIg)) by the same method as that used to produce compound (Ig) from compound (IVg), and $R^1$, $R^2$, $R^3$ and $R^4$, each of which may be protected, in a way similar to that described above, then removing the protecting group, followed by purification if necessary.

Compound (IVg) can be produced by binding $R^1$, $R^2$, $R^3$ and $R^4$, each of which may be protected, and compound (IIg) in a way similar to that used to bind compound (Ig).

Compound (IIg) can, for example, be produced by adding a hydrazide having one amino group protected by a protecting group to an acrylate, then removing the amino protecting group by the above-mentioned method, followed by purification as necessary. In this case, the amino protecting group may be one of the above-mentioned protecting groups. For this reaction, the acrylate itself may serve as a solvent, but alcohols such as ethanol, propanol and tert-butanol, halogenated hydrocarbons such as chloroform, dichloromethane and 1,2-dichloroethane, ethers such as ethyl ether, tetrahydrofuran, dioxane and dimethoxyethane, esters such as ethyl acetate, hydrocarbons such as benzene and toluene, amines such as pyridine, and amides such as N,N-dimethylformamide etc. may be used as solvents. The reaction is accelerated by heating to about 50 to 200° C., preferably about 50 to 100° C.

The above synthesis reaction may employ the following various protecting groups for amino groups, carboxyl groups, hydroxyl groups, carbonyl groups etc.

Protecting groups for amino groups include amide forming protecting groups such as formyl, acetyl, chloroacetyl, dichloroacetyl, trichloroacetyl, trifluoroacetyl, acetoacetyl and o-nitrophenylacetyl; carbamate-forming protecting groups such as tert-butoxycarbonyl, benzyloxycarbonyl, p-methoxybenzyloxycarbonyl, p-nitrobenzyloxycarbonyl, 2-chlorobenzyloxycarbonyl, 2,4-dichlorobenzyloxycarbonyl, benzhydryloxycarbonyl, 2,2,2-trichloroethoxycarbonyl, 2-trimethylsilylethoxycarbonyl, 1-methyl-1-(4-biphenyl)ethoxycarbonyl, 9-fluorenylmethoxy-carbonyl, 9-anthrylmethoxycarbonyl, isonicotinyloxycarbonyl and 1-adamantyloxycarbonyl; and trityl and phthaloyl.

Protecting groups for hydroxyl groups include ether-forming protecting groups such as methoxymethyl, benzyloxymethyl, tert-butoxymethyl, 2-methoxyethoxymethyl, 2-(trimethylsilyl)ethoxymethyl, methylthiomethyl, 2-tetrahydropyranyl, 4-methoxy-4-tetrahydropyranyl, 2-tetrahydropyranyl, benzyl, p-methoxybenzyl, p-nitrobenzyl, o-nitrobenzyl, 2,6-dichlorobenzyl and trityl; silyl ether-forming protecting groups such as trimethylsilyl, triethylsilyl, triisopropylsilyl, isopropyldimethylsilyl, diethylisopropylsilyl, tert-butyldimethylsilyl, tert-butyldiphenylsilyl, tribenzylsilyl, triphenylsilyl and methyldiphenylsilyl; and ester-forming protecting groups such as formyl, acetyl, chloroacetyl, dichloroacetyl, trichloroacetyl, pivaloyl, benzoyl, benzyloxycarbonyl and 2-bromobenzyloxycarbonyl.

Preferable protecting groups for carboxyl groups include ester-forming protecting groups such as methyl, ethyl, methoxymethyl, methoxyethoxymethyl, benzyloxymethyl, tert-butyl, benzyl, p-methoxybenzyl, p-nitrobenzyl, o-nitrobenzyl, benzhydryl, trityl, 2,2,2-trichloroethyl, 2-trimethylsilylethyl, allyl, cyclohexyl, cyclopentyl and phenacyl; and silyl ester-forming protecting groups such as trimethylsilyl, triethylsilyl, tert-butyldimethylsilyl, isopropyldimethylsilyl and dimethylphenylsilyl.

Protecting groups for carbonyl groups include acetal-, ketal-, dithioacetal- or dithioketal-forming protecting groups such as dimethyl, diethyl, dibenzyl and diacetyl; protecting groups that form 1,3-dioxane or 1,3-dioxolane that may be substituted; protecting groups that form 1,3-dithiane or 1,3-dithiolane; and substituted hydrazone-forming protecting groups such as N,N-dimethyl and 2,4-dinitrophenyl.

Methods of removing these protecting groups for amino groups, hydroxyl groups, carbonyl groups and carboxyl groups include the method using an acid, the method using a base, the method based on reduction, the method using ultraviolet irradiation, the method using hydrazine, the method using phenylhydrazine, the method using sodium N-methyldithiocarbamate, the method using tetrabutylammonium fluoride, the method using palladium acetate, the method using mercury chloride and the method using a Lewis acid; these common methods and other known means can be used as appropriate.

Here, the method using an acid is a common method of hydrolyzing amides, esters, silyl esters, silyl ethers, etc., and is applied to remove corresponding protecting groups. This method is often used to deprotect such groups as amino groups protected by, for example, tert-butoxycarbonyl, p-methoxybenzyloxycarbonyl, benzhydryloxycarbonyl, 9-anthrylmethoxycarbonyl, 1-methyl-1-(4-biphenyl) ethoxycarbonyl, 1-adamantyloxycarbonyl or trityl; and hydroxyl groups protected by, for example, methoxymethyl, tert-butoxymethyl, 2-tetrahydropyranyl, 4-methoxy-4-tetrahydropyranyl, 2-tetrahydrofuranyl or trityl. Preferable acids include organic acids such as formic acid, 1-trifluoroacetic acid, benzenesulfonic acid and p-toluenesulfonic acid; and inorganic acids such as hydrochloric acid, hydrobromic acid and sulfuric acid.

The method using a base, like that using an acid, is a common method of hydrolyzing amides, esters etc., and is applied to remove corresponding protecting groups. For example, organic bases are effective in deprotecting amino groups protected by 9-fluorenylmethoxycarbonyl. Preferable bases include inorganic bases, e.g., alkali metal hydroxides such as lithium hydroxide, sodium hydroxide and potassium hydroxide, alkaline earth metal hydroxides such as magnesium hydroxide and calcium hydroxide, alkali metal carbonates such as sodium carbonate and potassium carbonate, alkaline earth metal carbonates such as magnesium carbonate and calcium carbonate, alkali metal hydrogen carbonates such as sodium hydrogen carbonate and potassium hydrogen carbonate, alkali metal acetates such as sodium acetate and potassium acetate, alkaline earth metal phosphates such as calcium phosphate and magnesium phosphate, alkali metal hydrogen phosphates such as disodium hydrogen phosphate and dipotassium hydrogen phosphate, and aqueous ammonia; and organic bases such as trimethylamine, triethylamine, diisopropylethylamine, pyridine, picoline, N-methylpyrrolidine, piperidine, N-methylpiperidine, N-methylmorpholine, 1,5-diazabicyclo [4.3.0]non-5-ene, 1,4-diazabicyclo[2.2.2]octane and 1,8-diazabicyclo[5.4.0]-7-undecene.

The method based on reduction is applied to deprotect such groups as amino groups protected by, for example, trichloroacetyl, trifluoroacetyl, o-nitrophenylacetyl, 2,2,2-trichloroethoxycarbonyl, benzyloxycarbonyl, p-nitrobenzyloxycarbonyl, 2,4-dichlorobenzyloxycarbonyl, isonicotinyloxycarbonyl or trityl; hydroxyl groups protected by, for example, benzyl or p-nitrobenzyl; and carboxyl groups protected by, for example, benzyloxymethyl, benzyl, p-nitrobenzyl, phenacyl, 2,2,2-trichloroethyl or benzhydryl. Preferable reduction methods include reduction using sodium borohydride, reduction using zinc/acetic acid and catalytic reduction.

The method using ultraviolet irradiation is used to deprotect hydroxyl groups and carboxyl groups protected by, for example, o-nitrobenzyl.

The method using hydrazine is used to deprotect amino groups protected by, for example, phthaloyl (e.g., phthalimide groups).

The method using phenylhydrazine is used to deprotect amino groups protected by, for example, acetoacetyl.

The method using sodium N-methyldithiocarbamate is used to deprotect amino groups and hydroxyl groups protected by, for example, chloroacetyl.

The method using tetrabutylammonium fluoride is used to remove the protecting group from, for example, 2-trimethylsilylethyl carbamate, silyl ethers and silyl esters, to obtain amino groups, hydroxyl groups and carboxyl groups, respectively.

The method using palladium acetate is used to remove the protecting group from, for example, allyl esters, to obtain carboxyl groups.

The method using mercury chloride is used to deprotect hydroxyl groups protected by, for example, methylthiomethyl.

The method using a Lewis acid is used to deprotect hydroxyl groups protected by, for example, 2-methoxyethoxymethyl. Preferable Lewis acids include zinc bromide and titanium tetrachloride.

The intermediates, products and final products obtained by the above synthesis reaction, as necessary, can be isolated and purified by the conventional or the following method for separation and purification, such as concentration, vacuum concentration, solvent extraction, crystallization, recrystallization, chromatography, etc.

The compound of the present invention, represented by general formula (I) or (I'), or a pharmacologically acceptable ester or a salt thereof, having activity of inhibiting cystein protease (ICE, cathepsin B, shock cathepsin L, etc, preferably ICE, etc.) is safe with low toxicity, and can be used to treat and prevent various infectious diseases, immune diseases, bone diseases, neurologic diseases, tumors, inflammatory diseases etc., including meningitis, salpingitis, enteritis, inflammatory enteritis, hyperacidic enteritis, sepsis, septic shock, disseminated intravascular coagulation, adult respiratory distress, arthritis, bile duct disease, colitis, encephalitis, endocarditis, glomerular nephritis, hepatitis, myocarditis, pancreatitis, pericarditis, reperfusion disorder, angitis, acute and delayed allergies, graft rejection, psoriasis, asthma, type I diabetes mellitus, multiple sclerosis, allergic dermatitis, acute and chronic myelocytic leukemia, tissue calcium deficiency, rheumatism, rheumatoid arthritis, arthrosteitis, senile and climacteric osteoporosis, immobile and traumatic osteoporosis, arteriosclerosis, periodontitis, spatial pulmonary fibrosis, hepatic cirrhosis, systemic sclerosis, keloid, Alzheimer's disease and IL-1-producing tumors, in humans and other mammals (e.g., mice, rats, rabbits, dogs, cats, monkeys, bovines, swines). In particular, it is preferably used to treat and prevent bone diseases (e.g. rheumatoid arthritis) or septic shock, for instance.

The compound of the present invention, represented by general formula (I) or (I'), or a pharmaceutically acceptable ester or a salt thereof, can be administered orally or non-orally, as such, or as formulated with a pharmaceutically acceptable carrier, in the form of solid preparations such as tablets, capsules, granules and powders, or liquid preparations such as syrups and injectable preparations.

The prophylactic/therapeutic preparation of the present invention can be produced by commonly used methods such as mixing, kneading, granulation, tableting, coating, sterilization and emulsification, depending on preparation form. These preparations can be produced with reference toe for example, the provisions given under various terms of the General Rules for Preparations, Pharmacopoeia of Japan.

The content of compound (I) or (I') in the preparation of the present invention is normally about 0.01 to 100% by weight, preferably about 0.1 to 50% by weight, and more preferably about 0.5 to 20% by weight, relative to the entire preparation, depending on preparation form.

Pharmaceutically acceptable carriers are various organic or inorganic carrier substances in common use as pharmaceutical materials, including excipients, lubricants, binders and disintegrating agents for solid preparations, and solvents, dissolution aids, suspending agents, isotonizing agents, buffers and smoothing agents for liquid preparations. Other pharmaceutical additives such as preservatives, antioxidants, coloring agents and sweetening agents may be used as necessary. Preferable excipients include lactose, sucrose, D-mannitol, starch, crystalline cellulose and light silicic anhydride. Preferable lubricants include magnesium stearate, calcium stearate, talc and colloidal silica. Preferable binders include crystalline cellulose, sucrose, D-mannitol, dextrin, hydroxypropyl cellulose, hydroxypropylmethyl cellulose and polyvinylpyrrolidone. Preferable disintegrating agents include starch, carboxymethyl cellulose, carboxymethyl cellulose calcium, crosscarmellose sodium and carboxymethyl starch sodium. Preferable solvents include water for injection, alcohol, propylene glycol, macrogol, sesame oil and corn oil. Preferable dissolution aids include polyethylene glycol, propylene glycol, D-mannitol, benzyl benzoate, ethanol, tris-aminomethane, cholesterol, triethanolamine, sodium carbonate and sodium citrate. Preferable suspending agents include surfactants such as stearyltriethanolamine, sodium lauryl sulfate, laurylaminopropionic acid, lecithin, benzalkonium chloride, benzethonium chloride and monostearic glycerol, and hydrophilic polymers such as polyvinyl alcohol, polyvinylpyrrolidone, carboxymethyl cellulose sodium, methyl cellulose, hydroxymethyl cellulose, hydroxyethyl cellulose and hydroxypropyl cellulose. Preferable isotonizing agents include sodium chloride, glycerol and D-mannitol. Preferable buffers include buffer solutions of phosphates, acetates, carbonates and citrates. Preferable smoothing agents include benzyl alcohol. Preferable preservatives include p-oxybenzoic acid esters, chlorobutanol, benzyl alcohol, phenethyl alcohol, dehydroacetic acid and sorbic acid. Preferable antioxidants include sulfites and ascorbic acid.

The compound of the present invention may be orally or non-orally administered to humans and other animals suffering from various diseases as described above, at doses of, for example, 0.01 to 500 mg/day, preferably 0.1 to 50 mg/day, more preferably 1 to 20 mg/day, per kg body weight.

Although the dose varies depending on kind of compound (I) or (I'), route of administration, symptoms, patient age etc., it can be administered at 0.1 to 50 mg/day, preferably 1 to 20 mg/day, per kg of body weight, in 1 to 6 portions, for oral administration to an adult patient with rheumatoid arthritis.

The compound (I) and (I') of the present invention can also be used as appropriately formulated with other pharmaceutically active components. Such active components include oxonin, indomethacin, methotrexate, auranofin and bucillamine.

Abbreviations for amino acids, compounds and others used in the present specification are based on abbreviations specified by the IUPAC-IUB Commission on Biochemical Nomenclature or abbreviations in common use in relevant fields. Some examples are given below. When an optical isomer may be present in amino acid, it is of the L-configuration, unless otherwise stated.

Gly or G: Glycine
Ala or A: Alanine
Val or V: Valine
Leu or L: Leucine
Ile or I: Isoleucine
Ser or S: Serine
Thr or T: Threonine
Cys or C: Cysteine
Met or M: Methionine
Glu or E: Glutamic acid
Asp or D: Aspartic acid
Lys or K: Lysine
Arg or R; Arginine
His or H: Histidine
Phe or F; Phenylalanine
Tyr or Y: Tyrosine
Trp or W: Tryptophan
Pro or P: Proline
Asn or N: Asparagine
Gln or Q: Glutamine
Ach: 1-aminocyclohexane carboxylic acid
Acp: 1-aminocyclopentane carboxylic acid
Aib: Aminoisobutyric acid
Nle: Norleucine
Abu: 2-aminobutyric acid
Nva: Norvaline
β-Ala: β-alanine
Fmoc: 9-fluorenylmethoxycarbonyl
$Bu^t$: tert-butyl
DCC: N,N'-dicyclocarbodiimide
HONB: 1-hydroxy-5-norbornene-2,3-dicarboxyimide
HOBt: 1-hydroxybenzotriazole
Ac: Acetyl
Z: Benzyloxycarbonyl
Boc: t-butoxycarbonyl
Bzl: Benzyl
WSCD: 1-ethyl-3-(3-dimethylamino-propyl)carbodiimide
BOP: Benzotriazol-1-yl-oxy-tris(dimethyl-amino) phosphonium hexafluorophosphate
TFA: Trifluoroacetic acid
AcOEt: Ethyl acetate
DMF: Dimethylformamido
THF: Tetrahydrofuran
TEA: Triethylamine
DMSO: Dimethylsulfoxide
Ph: Phenyl

BEST MODE FOR CARRYING OUT THE INVENTION

The present invention is hereinafter described in more detail by means of the following reference examples and examples, which are not to be construed as limitative to the present invention and may be varied, as long as the scope of the present invention is not deviated from.

REFERENCE EXAMPLE 1

Cloning of CDNA of Human Peripheral Monocytic IL-1β Converting Enzyme (ICE)

To amplify ICE CDNA by the polymerase chain reaction method, the following four primers were synthesized with reference to the published base sequence of human peripheral monocytic IL-1β converting enzyme (ICE) [Nancy A. Thornberry, Nature, Vol. 356, pp. 768–774 (1992)].

Sense primer No. 1:
5'-AAAAGGAGAGAAAAGCCATG-3'(Sequence ID number:1) Sense primer No. 2:
5'-pGGAATTCCAAAGCCATGGCCGACAAGGT-3' (Sequence ID number:2) Anti-sense primer No. 3:
5'-pGGAATTCCTTCCTGCCCGCAGACATTCA-3' (Sequence ID number:3) Anti-sense primer No. 4:
5'-TTTACAGAACGATCTCTTCA-3'(Sequence ID number:4)

5 μl of a solution of CDNA library λgtll derived from human peripheral monocytes (Clontech Laboratory) and 45 μl of distilled water were mixed and incubated at 90° C. for 10 minutes, after which the mixture was quenched in ice. After two primers (primer Nos. 1 and 4 above; each 50 pmol) were added, the reaction (at 94° C. for 2 minutes, at 55° C. for 2 minutes and at 72° C. for 1.5 minutes) was repeated in 50 cycles using $Vent^R$ DNA polymerase (New England Biolabs). To this reaction mixture, two other primers (primer Nos. 2 and 3 above; each SO pmol) were added, followed by the same reaction as above. Separation of the PCR product by 1.2% agarose gel electrophoresis confirmed the presence of an amplified DNA fragment at a position corresponding to the size (1,256 bp) expected from the base sequence of human peripheral monocytic ICE. This DNA fragment was recovered from the gel and subcloned into the plasmid vector $pBluescript^R$ II $KS^+$ (STRATAGENE). The base sequence of the CDNA portion was determined to be identical to an already reported sequence by the dideoxynucleotide synthetic chain termination method [J. Messing et al., Nucleic Acids Research, Vol. 9, p. 309 (1981)]. The plasmid containing this cDNA fragment was named pICE-5.

REFERENCE EXAMPLE 2

Expression of ICE in *Escherichia coli* MM294 (DE3)

With the plasmid pICE-5 as prepared in Reference Example 1 as a template, the ICE gene was amplified using a primer having a BamHI site added to its 5'-terminal. The amplified gene was inserted into pET-3c, a plasmid vector for expression in *Escherichia coli* [Methods in Enzymology, ed. D. V. Goeddel, Vol. 185, p. 68, Academic Press (1990)]. The thus-constructed plasmid was named pET-ICE. Escherichiacoli MM294 (DE3) was transformed with pET-ICE and allowed to express ICE under control of the T7 promotor [Methods in Enzymology, Vol. 185, p. 60 (1990)]. The transformed *E. coli* was cultured; the cultured cells were ultrasonically disrupted and subjected to SDS-polyacrylamide gel electrophoresis (SDS-PAGE), resulting in the detection of a unique band corresponding to ICE near 49 kDal. Since the expressed product formed an inclusion body, ICE was crudely purified from the precipitate fraction of the ultrasonically disrupted transformant.

REFERENCE EXAMPLE 3
Preparation of antiserum against recombinant ICE

Crudely purified recombinant ICE as prepared in Reference Example 2 was mixed with an equal amount of Freund's complete adjuvant; about 1 ml of this mixture was inoculated to a rabbit. A mixture of a standard preparation of crudely purified ICE and an equal amount of Freund's incomplete adjuvant was then injected 3 times at 2-week intervals; blood was collected at 7 days following final injection. The blood was kept standing at 37° C. for 30 minutes and subsequently at 4° C. overnight, after which it was centrifuged to yield an antiserum against ICE.

REFERENCE EXAMPLE 4
Preparation of recombinant DNA for ICE gene expression in insect cells After the plasmid pICE-5 as prepared in Reference Example 1 was digested with restriction enzyme EcoRI, the ICE CDNA fragment was recovered via agarose gel electrophoresis. Next, to the restriction enzyme EcoRI site of pVL-1393, a vector for expression in insect cells (Invitrogen Corporation), the above cDNA fragment was inserted by the action of T4 DNA ligase and ATP to yield the expression plasmid pVL-ICE.

REFERENCE EXAMPLE 5
ICE gene expression in insect cells

Using the plasmid described in Reference Example 4 (pVL-ICE), the insect cell Sf9 was transformed as directed in the instruction manual provided with the MAXBAC Baculovirus Expression System (Invitrogen Corporation). The insect cell Sf9 was infected with the resulting recombinant virus at an m.o.i. (viral particle count per cell) of 1, followed by cultivation for 4 days. Virus-infected cells were recovered and subjected to Western blotting; a unique band, reactive to the antiserum obtained in Reference Example 3, was confirmed at positions corresponding to molecular weights of 25,000 and 15,800. After the cells infected with the recombinant virus were ultrasonically disrupted, the supernatant was recovered via centrifugation and treated as reported by Nancy A. Thornberry et al. [Nature, Vol. 356, pp. 768–774 (1992)]. ICE activity for reaction to the synthetic substrate (Ac-Y-V-A-D-MCA) was thereby detected.

REFERENCE EXAMPLE 6
Crude purification of ICE

Two ml of the ICE expression recombinant virus suspension as prepared in Reference Example 5 was added to the insect cell Sf9 cultured in 2 1 of Sf900 medium containing 5% fetal calf serum (FCS) ($1.5 \times 10^6$ cells/ml) to cause infection. Post-infection cultivation was conducted at 27° C. in a spinner flask for 4 days. Cultured cells were recovered (hereinafter all operations conducted on ice), washed 3 times with PBS (–), and suspended in a hypotonic buffer (20 mM KCl, 25 mM HEPES, pH 7.4, 5 MM $MgCl_2$, 1 MM EDTA, 1 MM PMSF, 10 μg/ml pepstatin and leupeptine) to $10^8$ cells/ml. After the suspension was kept standing on ice for 20 minutes, cells were disrupted (25 times) using a Dounce homogenizer. Disrupted cells were removed via centrifugation; ammonium sulfate was added to the supernatant to 40% saturation; the precipitate fraction was removed via centrifugation. Ammonium sulfate was further added to 80% saturation; the precipitate was recovered. The precipitate was dissolved in buffer A (20 mM KCl, 25 mM HEPES, pH 7.4, 5 mM EDTA, 2 mM DTT, 1 mM PMSF, 0.1% NP-40, 10% glycerol) and dialyzed against buffer A overnight.

After the precipitate was removed from the above dialyzate via centrifugation (30,000×g, 30 minutes), the supernatant was passed through a DEAE Sepharose Fast Flow column (1.6×10 cm), previously equilibrated with buffer A. The effluent fraction was recovered and used as an ICE enzyme solution.

REFERENCE EXAMPLE 7
Preparation of Z—NH—CH($CH_2OH$)$CH_2CH_2CO_2Bu^t$ 3.00 g (8.89 mmol) of Z—Glu(OBu$^t$)—OH was dissolved in 25 ml of tetrahydrofuran; 1.75 mg (9.78 mmol) of HONB and 2.11 mg (10.2 mmol) of DCC were added at 0° C. After the reaction mixture was stirred at 0° C. for 70 minutes and 28° C. for 30 minutes, the insoluble substances were filtered off. The filtrate was concentrated under reduced pressure and dissolved in 12.5 ml of tetrahydrofuran and 12.5 ml of methanol. This solution was added drop by drop to a mixed solution of 1.68 mg (44.5 mmol) of sodium borohydride in 5 ml of water and 20 ml of methanol, being cooled with icesodium chloride, followed by stirring for 15 minutes. After completion of the reaction, 26.1 ml (336 mmol) of acetone was added; the resulting insoluble substances were filtered off; the filtrate was concentrated under reduced pressure. To the oily substance thus obtained, ethyl acetate was added; the solution was washed with a saturated aqueous solution of sodium hydrogen carbonate and saturated saline, and dried with anhydrous sodium sulfate. After the desiccant was filtered off, the filtrate was concentrated under reduced pressure to yield 3.16 g (100%) of the title compound.

REFERENCE EXAMPLE 8
Preparation of Z—NH—CH(CH($OCH_3$)$_2$)$CH_2CH_2CO_2BU^t$ 2.88 g (8.91 mmol) of Z—NH—CH($CH_2OH$)$CH_2CH_2CO_2Bu^t$ as obtained in Reference Example 7 was dissolved in 18 ml of dimethyl sulfoxide; 3.72 ml (26.7 mmol) of triethylamine was added at 0° C.; subsequently, a solution of 2.83 g (17.8 mmol) of sulfur trioxide-pyridine complex in 18 ml of dimethyl sulfoxide was added drop by drop, followed by stirring for 20 minutes. After completion of the reaction, ice water and ethyl acetate were added; the organic layer was separated, washed with a saturated aqueous solution of sodium hydrogen carbonate and saturated saline, then dried with anhydrous sodium sulfate. After the desiccant was filtered off, the filtrate was concentrated under reduced pressure; to the resulting oily substance, 200 ml of methanol, 19.5 ml of trimethyl orth-formate and 84.7 mg (0.445 mmol) of p-toluenesulfonic acid were added, followed by overnight stirring at 28° C. After completion of the reaction, the reaction mixture was concentrated under reduced pressure; ethyl acetate was added; the solution was washed with a saturated aqueous solution of sodium hydrogen carbonate and saturated saline, then dried with anhydrous sodium sulfate. After the desiccant was filtered off, the filtrate was concentrated under reduced pressure, after which it was purified by silica gel column chromatography (30 g silica gel, hexane:ethyl acetate=2:1) to yield 3.03 g (92.8%) of the title compound.

Elemental Analysis Calculated (+0.1 $H_2O$): C, 61.80; H, 7.97; N, 3.79 Found: C, 61.53; H, 7.80; N, 3.71

REFERENCE EXAMPLE 9

Preparation of $H_2N$—CH(CH($OCH_3$)$_2$)$CH_2CH_2CO_2Bu^t$ 470 mg (1.28 mmol) of Z—NH—CH(CH($OCH_3$)$_2$)$CH_2CH_2CO_2Bu^t$ as obtained in Reference Example 8 was dissolved in 6 ml of tetrahydrofuran; palladium black was added. After nitrogen replacement, hydrogen was passed for 60 minutes. The palladium black was filtered off; the filtrate was concentrated under reduced pressure to yield 2.88 mg (96.6%) of the title compound.

REFERENCE EXAMPLE 10

Preparation of 2-Naphthoyl-Val-Ala-Glu(OBu$^t$)—OH

Z—Glu(OBu$^t$)$^{13\ OH}$ (5.06 g, 15 mmol) was hydrogenated in a mixture of N HCl (15 ml) and THF (100 ml) over palladium black as a catalyst at room temperature for 7 hours. After filtration of the catalyst, THF was evaporated. The residual aqueous solution containing H-Glu(OBu$^t$)—OH HCl was diluted with DMF (50 ml) and triethylamine (4.2 ml) was added under cooling. To this was added Z-Ala-ONb which was prepared in acetonitrile using Z-Ala-OH (4.46 g, 20 mmol), HONb (3.95 g, 22 mmol) and DCC (4.33 g, 21 mmol) followed by removal of N,N'-dicyclohexcylurea by filtration. The mixture was stirred at room temperature for 17 hours. After evaporation of the solvent, the residue was dissolved in ethyl acetate and washed with N HCl and brine, dried over anhydrous sodium sulfate, and concentrated by evaporation. To the residual solution, N,N'-dicyclohexylamine was added to give crystalline, which was recrystallized from ethanol-ethyl acetate to give Z-Ala-Glu(OBu$^t$)—OH N,N'-dicyclohexylamine salt (7.06 g, 80%).

The dipeptide N,N'-dicyclohexylamine salt (7.04 g, 12 mmol) was dissolved in ethyl acetate and the solution was washed with N $H_2SO_4$ and water to remove N,N'-dicyclohexylamine, dried over anhydrous sodium sulfate, and evaporated. The resulting dipeptide was hydrogenated in the mixture of THEF (50 ml) and N HCl (12 ml) over palladium black as described above. After removal of the catalyst, THF was evaporated. The residual aqueous solution was diluted with DMF (30 ml) followed by addition of triethyl amine under cooling. An acetonitrile solution of Z-Val-ONb (14.4 mmol), which was prepared in a similar manner to that described above, was added and stirred at room temperature for 17 hours. The solvent was evaporated and the residue taken up in ethyl acetate. The mixture was washed with N HCl and water, dried over anhydrous sodium sulfate, and evaporated. The residue was recrystallized from ether-petroleum ether to give Z-Val-Ala-Glu(OBut)—OH (5.77 g, 94.8%).

The benzyloxycarboinyl group of the tripeptide (1.52 g, 3 mmol) was removed by hydrogenation over palladium black in the mixture of N HCl (3 ml) and DMF (20 ml) in a similar manner to that described above. At the end of the reaction, partially protected tripeptide hydrochloride was precipitated. After addition of water to dissolve the tripeptide, the catalyst was removed by filtration. The solvent was concentrated to about 15 ml and water (15 ml) was added. After addition of N-ethylmorpholine (1.28 ml, 10 mmol), 2-Naphthoyl chrolide (380 mg, 2 mmol) was added 4 portion-wise under vigorous stirring. The mixture was stirred at room temperature for 17 hours. Triethyl amine (256 ml, 1.83 mmol) and the chloride (380 mg, 2 mmol) were further added. After stirring at room temperature for 30 minutes, the mixture was diluted with water, adjusted to pH 2, and extracted with ethyl acetate. The organic layer was washed with N HCl and water, dried over anhydrous sodium sulfate, and evaporated. The residue were recrystallized from ethyl acetate-petroleum ether. 1.17 g (73.9%).

Silica gel thin layer chromatography: Rf=0.54 (chroloform:methanol:acetic acid=90:10:5).

REFERENCE EXAMPLE 11

Preparation of 2-Naphthoyl-Val-Ala-Glu(OEt)—OH

This compound was synthesized in a similar procedure to that of Reference Example 10 using H-Glu(OEt)—OH HCl in place of H-Glu(OBut)—OH HCl.

Silica gel thin layer chromatography: Rf=0.50 (chloroform:methanol=acetic acid=90:10:5).

REFERENCE EXAMPLE 12

Preparation of Z—NHCH($COCH_2Br$)$CH_2CH_2COOEt$

Z-Glu(OEt)—OH (1.24 g, 4 miol) was dissolved in anhydrous THF (20 ml). To this were added N-ethylmorpholine (0.616 ml, 5.6 mmol) and isobutylchloroformate (0.681 ml, 5.2 mmol) at −20° C., and the mixture was stirred at −15° C. for 15 minutes. A solution of diazomethane (8 mmol) in ether (10 ml) was added at this temperature, and stirred at room temperature for 2 hours. Again, the solution was cooled to −20° C., the mixture of 48% HBr (8 ml)-acetic acid (8 ml) was added, and then stirred at −10° C. for 15 minutes. The mixture was diluted with water and extracted ethyl acetate. The organic layer was washed with water, saturated $NaHCO_3$ and water, dried over sodium sulfate, and evaporated. The residue was recrystallized from ethyl aacetate and petroleum ether. 1.2 g (77.7%).

Silica gel thin layer chromatography: RF=0.41 (chloroform:methanol:acetic acid=90:10:5).

REFERENCE EXAMPLE13

Preparation of Z—NHCH($COCH_2Br$)$CH_2CH_2COOBu^t$

This compound was synthesized in the same method as that of Reference Example 12 using Z-Glu(OBu$^t$)—OH (3.37 g, 10 mmol). The desired product was obtained as an oil.

REFERENCE EXAMPLE 14

Preparation of 2-Naphthoyl-Val-Ala-NHCH($COOCH_2Br$)$CH_2CH_2COOBu^t$

To a solution of 2-Naphthoyl-Val-Ala-Glu(OBu$^t$)—OH (527 mg, 1 mmol) in THF (10 ml) was added N-methylmorpholine (0.143 ml, 1.3 mmol) and isobutyl chloroformate at −20° C., and the mixture was stirred at −15° C. for 15 minutes. The mixture was further cooled to −20° C., and a solution of diazomethane (2 mmol) in ether (2 ml) was added. After stirring at room temperature for 2 hours, a mixture of 48% HBr (1 ml) and acetic acid (1 ml) was added at −20° C. and stirred at −10° C. for 15 minutes. Ethyl acetate and water were added and the organic layer was washed with water, saturated $NaHCO_3$, and brine, dried over anhydrous sodium sulfate, and evaporated. The residue was recrystallized from ethyl acetate and petroleum ether. 211 mg (35%). * mmol). 1.27 g (92.5%).

Elemental analysis

Calculated: C, 57.62 H, 6.34 N, 9.95 Found: C, 57.59 H, 6.42 N, 7.06

REFERENCE EXAMPLE 15
Preparation of 2-Naphthoyl-Val-Ala-NHCH(COCH$_2$Br)CH$_2$CH$_2$COOEt This compound was obtained in a similar manner to that described in Reference Example 14 using 2-Naphthoyl-Val-Ala-Glu(OEt)—OH (2.68 g, 5.37 mmol). 1.38 g (44.5%)

Elemental analysis

Calculated: C, 56.35 H, 5.78 N, 7.30 Found: C, 56.61 H, 5.98 N, 7.31

REFERENCE EXAMPLE 16
Preparation of H-Val-Ala-NH—CH[CH(OCH$_3$)$_2$]CH$_2$CH$_2$CO$_2$Bu$^t$ WSCD-HCl (120 mg, 0.627 mmol) was added to a stirred DMF solution (3 ml) of Z-Val-Ala-OH (202 mg, 0.627 mmol) and H$_2$N—CH[CH(OCH$_3$)$_2$]CH$_2$CH$_2$CO$_2$Bu$^t$ (133 mg, 0.570 mmol) as obtained in Reference Example 9 and HOBt (84.7 mg, 0.627 mmol)) at 0° C. The reaction mixture was stirred for 22 h at room temperature and concentrated invacuo. The residue was washed with H$_2$O and dried. The product (250 mg, 0.465 mmol) was hydrogenated in THF over Pd black for 4 h, filtered and concentrated invacuo to give the title compound (211 mg, 67.5%)

REFERENCE EXAMPLE 17
Preparation of Z—NHCH(CH$_2$CH$_2$CO$_2$Bu$^t$)CHOHCH$_2$SO$_2$Ph a) Preparation of Z-Glu(OBu$^t$)—CH$_2$SO$_2$Ph 1.6M n-BuLi in hexane (8.14 ml) was added to a stirred solution of CH$_3$SO$_2$Ph (925 mg, 5.92 mmol) in THF (20 ml) at 0° C. Z-Glu(OBu$^t$)—OCH$_3$ (2.16 g, 640 mmol) in THF (20 ml) was added to the solution at –78° C. The reaction mixture was stirred for 20 min at –30° C. Aqueous NH$_4$Cl was added to the reaction mixture and the solution was extracted with AcOEt. The organic layer was washed with brine, dried over anhydrous Na$_2$SO$_4$, and concentrated in vacuo. The residue was crystallized from hexane to give the title compound (2.08 g, 74.1%).

Elemental analysis

Calculated for C$_{24}$H$_{30}$O$_7$NS: C, 60.49; H, 6.34; N, 2.94. Found: C, 60.19; H, 6.15; N, 3.03 b) Preparation of Z—NHCH(CH$_2$CH$_2$CO$_2$Bu$^t$)CHOHCH$_2$SO$_2$Ph

Z-Glu(OBu$^t$)—CH$_2$SO$_2$Ph (2.00 g, 4.21 mmol) as obtained in Reference Example 17-a) in THF (20 ml) was added to a stirred solution of NaBH$_4$ (795 mg, 21.0 mmol) in methanol (16 ml) and H$_2$O (4 ml) at –50° C. The reaction mixture was stirred for 30 min at –30° C. and acetone (6.2 ml) was added. AcOEt was added to the solution and the organic layer was washed with brine, dried over anhydrous Na$_2$SO$_4$, and concentrated invacuo. The residue was crystallized from ether and hexane to give the title compound (1.38 g, 68.9%).

Calculated for C$_{24}$H$_{32}$O$_7$NS: C, 60.23; H, 6.74; N, 2.93. Found: C, 60.34; H, 6.50; N, 2.95

REFERENCE EXAMPLE 18
Preparation of Z-Glu(OBu$^t$)—CH$_2$SCH$_2$CH$_2$CH$_3$ Potassium carbonate (500 mg, 3.63 mmol) and CH$_3$CH$_2$CH$_2$SH (131 μl, 1.45 mmol) were added to a stirred solution of Z-Glu(OBu$^t$)—CH$_2$Br (500 mg, 1.21 mmol) in DMF (6 ml) at room temperature. The reaction mixture was stirred for 19 h and AcOEt was added. The solution was washed with brine, dried over anhydrous Na$_2$SO$_4$ and concentrated in vacuo. The residue was chromatographed on silica gel using hexane-AcOEt, (5:1) as a solvent and the eluate was concentrated in vacuo to give the title compound (236 mg, 47.8%).

REFERENCE EXAMPLE 19
Preparation of Z—NHCH(CH$_2$CH$_2$CO$_2$Bu$^t$)CHOHCH$_2$SO$_2$CH$_2$CH$_2$CH$_3$ A solution of metachloroperbenzoic acid (341 mg, 1.38 mmol) in CH$_2$Cl$_2$ (5 ml) was added to a stirred solution of Z-Glu(OBu$^t$)—CH$_2$SCH$_2$CH$_2$CH$_3$ (236 mg, 0.576 mmol) as obtained in Reference Example 18 in CH$_2$Cl$_2$ (10 ml) at 0° C. The reaction mixture was stirred for 40 min at room temperature and AcOEt was added. The solution was washed with aqueous NaHCO$_3$ and brine, dried over anhydrous Na$_2$SO$_4$, and concentrated in vacuo to give 249 mg of Z-Glu(OBu$^t$)—CH$_2$SO$_2$CH$_2$CH$_2$CH$_3$.

Z-Glu(OBu$^t$)—CH$_2$SO$_2$CH$_2$CH$_2$CH$_3$ (249 mg, 0.564 mmol) in TEF (2.5 ml) was added to a stirred solution of NaBH$_4$ (107 mg, 2.82 mmol) in methanol (2 ml) and H$_2$O (0.5 ml) at –50° C. The reaction mixture was stirred for 20 min at –30° C. and acetone (828 μl) was added. After AcOEt and water were added to the solution, the organic layer was washed with aqueous NaHCO$_3$ and brine, dried over anhydrous Na$_2$SO$_4$, and concentrated in vacuo to give the title compound (193 mg, 77.2%).

REFERENCE EXAMPLE 20
Preparation of Fmoc-NH—CH(CH$_2$OH)CH$_2$COOBu$^t$ 4.1 g Fmoc-Asp(OBu$^t$)—OH was dissolved in tetrahydrofuran; 1.39 g of HONB and 2.37 g of DCC were added at 0° C. while the solution was stirred. After the reaction mixture was stirred at 0° C. for 1 hour and 28° C. for 14 hours, the insoluble substances were filtered off. The filtrate was concentrated under reduced pressure and dissolved in a mixed solvent of methanol (15 ml) and tetrahydrofuran (15 ml). This solution was added drop by drop to a solution of 1.89 g of NaBH$_4$ in 6 ml of water and 24 ml of methanol at –10° C. with stirring. After being stirred at –10° C. for 30 minutes, the solution was cooled to –60° C., and adjusted to pH 3 by the addition of 6 M hydrochloric acid. Ethyl acetate was added; the organic layer was washed with 10% aqueous citric acid, saturated aqueous sodium hydrogen carbonate and saturated saline. After being dried with anhydrous sodium sulfate, the organic layer was concentrated under reduced pressure, followed by the addition of hexane to the residue, to yield 3.45 g (86.8%) of the title compound as a white powder.

Elemental analysis

Calculated: C, 69.50; H, 6.85; N, 3.52 Found: C, 69.57; H, 6.71; N, 3.76

REFERENCE EXAMPLE 21
Preparation of Fmoc-NH—CH[CH(OCH$_3$)$_2$]CH$_2$COOBu$^t$ 1.0 g of Fmoc-NH—CH(CH$_2$OH)CH$_2$COOBu$^t$ was dissolved in 5 ml of dimethyl sulfoxide; 1.0 ml of triethylamine was added. While the solution was stirred at 0° C., a solution of 0.8 g of sulfur trioxide-pyridine complex in 5 ml of dimethyl sulfoxide was added drop by drop. After being stirred at 15° C. for 20 minutes, the reaction mixture was separated into fractions by the addition of ice water and ethyl acetate. The organic layer was washed with 10% aqueous citric acid, saturated aqueous sodium hydrogen carbonate and saturated saline. After being dried with anhydrous sodium sulfate, the organic layer was concentrated under reduced pressure; 100 ml of methanol, 10 ml of trimethyl o-formate and 50 mg of p-toluenesulfonic acid were added to the residue, followed by stirring at 28° C. for 14 hours, after which the mixture was concentrated under reduced pressure. To the residue, ethyl acetate was added; the mixture was washed with saturated aqueous sodium hydrogen carbonate and saturated saline. After being dried with anhydrous sodium sulfate, the organic layer was concentrated under reduced pressure; the residue was purified through a silica gel column (2.8 cm dia.×20 cm) with ethyl acetate-:hexane (1:2) as an eluent; the fraction containing the desired product was concentrated under reduced pressure to yield the title compound as a colorless oily substance.

REFERENCE EXAMPLE 22
Preparation of Z—NH—CH(CH(OCH$_3$)$_2$)CH$_2$CO$_2$Bu$^t$ In the asame manner as in Reference Example 7 and 8, the title compound was obtained using Z-Asp(OBu$^t$)—OH.

Elemental analysis

Calculated: C, 60.86; H, 7.72; N, 3.94 Found: C, 60.84; H, 7.61; N, 4.04

EXAMPLE 1
Preparation of (+)Camphorsulfonyl-Val-Ala-HN—CH(CH(OCH$_3$)$_2$)CH$_2$CH$_2$CO$_2$Bu$^t$ 150 mg (0.373 mmol) of (+)Camphorsulfonyl-Val-Ala-OH, 104 mg (0.447 mmol) of H$_2$N—CH(CH(OCH$_3$)$_2$)CH$_2$CH$_2$CO$_2$Bu$^t$ as obtained in Reference Example 9 and HOBt (50.4 mg, 0.373 mmol) were dissolved in 2 ml of dimethylformamide; 71.4 mg (0.373 mmol) of WSCD·HCl was added at 0° C. The reaction mixture was stirred at 0° C. for 15 minutes and 28° C. for 24 hours. After completion of the reaction, the reaction mixture was concentrated under reduced pressure; the residue was dissolved in ethyl acetate and washed with a 10% aqueous solution of citric acid, a saturated aqueous solution of sodium hydrogen carbonate and saturated saline, then dried with anhydrous sodium sulfate. After the desiccant was filtered off, the filtrate was concentrated under reduced pressure, followed by trituration in hexane, to yield 151 mg (65.6%) of the title compound.

Elemental analysis

Calculated: C, 56.38; H, 8.32; N, 6.80 Found: C, 56.03; H, 8.35; N, 7.11

EXAMPLE 2
Preparation of (+)Camphorsulfonyl-Val-Ala-HN—CH(CHO)—CH$_2$CH$_2$CO$_2$H 110 mg (0.178 mmol) of (+)Camphorsulfonyl-Val-Ala-HN—CH(CH(OCH$_3$)$_2$)CH$_2$CH$_2$CO$_2$Bu$^t$ as obtained in Example 1 was dissolved in 2 ml of TFA, stirred for 2.5 hours, and concentrated under reduced pressure. The resulting oily substance was triturated in ether to yield 72.7 mg (79.2%) of the title compound as a powder.

Elemental analysis

Calculated (+0.5 H$_2$O): C, 52.66; H, 7.30; N, 8.01 Found: C, 52.54; H, 7.36; N, 8.07

EXAMPLE 3
Preparation of (−)Camphorsulfonyl-Val-Ala-HN—CH(CH(OCH$_3$)$_2$)CH$_2$CH$_2$CO$_2$Bu$^t$ 150 mg (0.373 mmol) of (−)Camphorsulfonyl-Val-Ala-OH, 104 mg (0.447 mmol) of H$_2$N—CH(CH(OCH$_3$)$_2$)CH$_2$CH$_2$CO$_2$Bu$^t$ as obtained in Reference Example 9 and 50.4 mg (0.373 mmol) of 1-hydroxybenzotriazole were dissolved in 2 ml of dimethylformamide; 71.4 mg (0.373 mmol) of WSCD·HCl was added at 0° C. The reaction mixture was stirred at 0° C. for 15 minutes and 28° C. for 24 hours. After completion of the reaction, the reaction mixture was concentrated under reduced pressure; the residue was dissolved in ethyl acetate and washed with a 10% aqueous solution of citric acid, a saturated aqueous solution of sodium hydrogen carbonate and saturated saline, then dried with anhydrous sodium sulfate. After the desiccant was filtered off, the filtrate was concentrated under reduced pressure, followed by trituration in hexane, to yield 142 mg (61.7%) of the title compound as a powder.

Elemental analysis

Calculated: C, 56.38; H, 8.32; N, 6.80 Found: C, 56.13; H, 8.02; N, 6.90

EXAMPLE 4
Preparation of (−)Camphorsulfonyl-Val-Ala-HN—CH(CHO)—CH$_2$CH$_2$CO$_2$H 110 mg (0.178 mmol) of (−)Camphorsulfonyl-Val-Ala-HN—CH(CH(OCH$_3$)$_2$)CH$_2$CH$_2$CO$_2$Bu$^t$ as obtained in Example 3 was dissolved in 2 ml of TFA, stirred for 2.5 hours, and concentrated under reduced pressure. The resulting oily substance was powdered by the addition of ether to yield 79.2 mg (86.3%) of the title compound.

Elemental analysis

Calculated (+H$_2$O): C, 51.77; H, 7.37; N, 7.87 Found: C, 51.89; H, 7.28; N, 7.70

EXAMPLE 5
Preparation of 1-Naphthylacetyl-Val-Ala-HN—CH(CH(OCH$_3$)$_2$)—CH$_2$CH$_2$CO$_2$BU$^t$ 139 mg (0.390 mmol) of 1-Naphthylacetyl-Val-Ala-OH, 100 mg (0.429 mmol) of H$_2$N-CH(CH(OCH$_3$)$_2$)CH$_2$CH$_2$CO$_2$Bu$^t$ as obtained in Reference Example 9 and 52.7 mg (0.390 mmol) of HOBt were dissolved in 2 ml of dimethylformamide; 74.7 mg (0.390 mmol) of WSCD·HCl was added at 0° C., followed by stirring at 0° C. for 15 minutes and 28° C. for 15 hours. After completion of the reaction, the reaction mixture was concentrated under reduced pressure; a saturated aqueous solution of sodium hydrogen carbonate was added to the residue; the resulting precipitate was collected by filtration and washed thoroughly with water to yield 175 mg (78.6%) of the title compound.

Elemental analysis

Calculated (+0.2 H$_2$O): C, 64.72; H, 7.95; N, 7.30 Found: C, 64.63; H, 7.74; N, 7.41

EXAMPLE 6
Preparation of 1-Naphthylacetyl-Val-Ala-HN—CH(CHO)—CH$_2$CH$_2$CO$_2$H 120 mg (0.210 mmol) of 1-Naphthylacetyl-Val-Ala-HN—CH(CH(OCH$_3$)$_2$)CH$_2$CH$_2$CO$_2$Bu$^t$ as obtained in Example 5 was dissolved in 2.5 ml of TFA and stirred for 1.5 hours, after which 250 ml of water was added, followed by stirring for 3 hours. After the solution was concentrated under reduced pressure, the resulting oily substance was triturated in ether to yield 95.3 mg (96.7%) of the title compound as a powder.

Elemental analysis

Calculated (+0.7 H$_2$O): C, 62.28; H, 6.77; N, 8.72 Found: C, 62.02; H, 6.73; N, 8.66

EXAMPLE 7
Preparation of 2-Naphthylacetyl-Val-Ala-HN—CH(CH(OCH$_3$)$_2$)—CH$_2$CH$_2$CO$_2$Bu$^t$ 139 mg (0.390 mmol) of 2-Naphthylacetyl-Val-Ala-OH, 100 mg (0.429 mmol) of H$_2$N-CH(CH(OCH$_3$)$_2$)CH$_2$CH$_2$CO$_2$Bu$^t$ as obtained in Reference Example 9 and 52.7 mg (0.390 mmol) of HOBt were dissolved in 2 ml of dimethylformamide; 74.7 mg (0.390 mmol) of WSCD·HCl was added at 0° C., followed by stirring at 0° C. for 15 minutes and 28° C. for 16 hours. After completion of the reaction, the reaction mixture was concentrated under reduced pressure; a saturated aqueous solution of sodium hydrogen carbonate was added to the residue; the resulting precipitate was collected by filtration and washed thoroughly with water to yield 175 mg (78.3%) of the title compound.

Elemental analysis

Calculated (+0.6 $H_2O$): C, 64.52; H, 7.96; N, 7.28 Found: C, 64.46; H, 7.86; N, 7.39

EXAMPLE 8

Preparation of 2-Naphthylacetyl-Val-Ala-HN—CH(CHO)—$CH_2CR_2CO_2H$ 120 mg (0.210 mmol) of 2-Naphthylacetyl-Val-Ala-HN—CH(CH($OCH_3$)2)CH2CH2CO2$Bu^t$ as obtained in Example 7 was dissolved in 2.5 ml of TFA and stirred for 1.5 hours, after which 250 ml of water was added, followed by stirring for 3 hours. After the solution was concentrated under reduced pressure, the resulting oily substance was solidified by the addition of ether to yield 92.5 mg (93.8%) of the title compound.

Elemental analysis

Calculated (+O.6 $H_2O$): C, 62.51; H, 6.77; N, 8.75 Found: C, 62.35; H, 6.79; N, 8.87

EXAMPLE 9

Preparation of 1-Naphthoyl-Val-Ala-HN—CH(CH($OCH_3$)$_2$)—$CH_2CH_2CO_2Bu^t$ 161 mg (0.471 mmol) of 1-Naphthoyl-Val-Ala-OH, 110 mg (0.471 mmol) of $H_2N$-CH(CH($OCH_3$)$_2$) $CH_2CH_2CO_2Bu^t$ as obtained in Reference Example 9 and 63.7 mg (0.471 mmol) of HOBt were dissolved in 2.5 ml of dimethylformamide; 90.4 mg (0.471 mmol) of WSCD·HCl was added at 0° C., followed by stirring at 0° C. for 15 minutes and 28° C. for 16 hours. After completion of the reaction, ethyl acetate was added; the solution was washed with water, a saturated aqueous solution of sodium hydrogen carbonate and saturated saline, and dried with anhydrous sodium sulfate. After the desiccant was filtered off, the filtrate was concentrated under reduced pressure, after which it was solidified by the addition of ether and hexane to yield 184 mg (69.9%) of the title compound.

Elemental analysis

Calculated: C, 64.61; H, 7.77; N, 7.53 Found: C, 64.27; H, 7.56; N, 7.83

EXAMPLE 10

Preparation of 1-Naphthoyl-Val-Ala-HN—CH(CHO) $CH_2CH_2CO_2H$ 150 mg (0.269 mmol) of 1-Naphthoyl-Val-Ala-HN—CH(CH($OCH_3$)$_2$)$CH_2CH_2CO_2Bu^t$ as obtained in Example 9 was dissolved in 3.2 ml of TFA and stirred for 55 minutes, after which 320 ml of water was added, followed by stirring for 1.5 hours. After the solution was concentrated under reduced pressure, the resulting oily substance was solidified by the addition of ether to yield 117 mg (95.3%) of the title compound.

Elemental analysis

Calculated (+1.5 $H_2O$): C, 59.74; H, 6.68; N, 8.71 Found: C, 59.79; H, 6.32; N, 8.81

EXAMPLE 11

Preparation of 2-Naphthoyl-Val-Ala-HN—CH(CH($OCH_3$)$_2$)—$CH_2CH_2CO_2Bu^t$ 161 mg (0.471 mmol) of 2-Naphthoyl-Val-Ala-OH, 110 mg (0.471 mmol) of $H_2N$—CH(CH($OCH_3$)$_2$) $CH_2CH_2CO_2Bu^t$ as obtained in Reference Example 9 and 63.7 mg (0.471 mmol) of HOBt were dissolved in 2.5 ml of dimethylformamide; 90.4 mg (0.471 mmol) of WSCD·HCl was added at 0° C., followed by stirring at 0° C. for 15 minutes and 28° C. for 16 hours. After completion of the reaction, ethyl acetate was added; the solution was washed with water, a saturated aqueous solution of sodium hydrogen carbonate and saturated saline, and dried with anhydrous sodium sulfate. After the desiccant was filtered off, the filtrate was concentrated under reduced pressure, after which it was solidified by the addition of ether and hexane to yield 200 mg (75.9%) of the title compound.

Elemental analysis

Calculated: C, 64.61; H, 7.77; N, 7.53 Found: C, 64.27; H, 7.56; N, 7.83

EXAMPLE 12

Preparation of 2-Naphthoyl-Val-Ala-HN—CH(CHO) $CH_2CH_2CO_2H$ 150 mg (0.269 mmol) of 2-Naphthoyl-Val-Ala-HN—CH(CH($OCH_3$)$_2$)$CH_2CH_2CO_2Bu^t$ as obtained in Example 11 was dissolved in 3.2 ml of TFA and stirred for 55 minutes, after which 320 ml of water was added, followed by stirring for 1.5 hours. After the solution was concentrated under reduced pressure, the resulting oily substance was solidified by the addition of ether to yield 118 mg (95.9%) of the title compound.

Elemental analysis

Calculated (+$H_2O$): C, 60.88; H, 6.60; N, 8.87 Found: C, 60.65; H, 6.55; N, 8.89

EXAMPLE 13

Preparation of 1-Naphthalenesulfonyl-Val-Ala-HN—CH(CH($OCH_3$)$_2$) $CH_2CH_2CO_2Bu^t$ 100 mg (0.264 mmol) of 1-Naphthalenesulfonyl-Val-Ala-OH, 61.7 mg (0.264 mmol) of $H_2N$—CH(CH($OCH_3$)$_2$) $CH_2CH_2CO_2Bu^t$ as obtained in Reference Example 9 and 35.7 mg (0.264 mmol) of HOBt were dissolved in 1.5 ml of dimethylformamide; 50.7 mg (0.264 mmol) of WSCD·HCl was added at 0° C. The reaction mixture was stirred at 0° C. for 10 minutes and 28° C. overnight. After completion of the reaction, the reaction mixture was concentrated under reduced pressure, the residue was dissolved in ethyl acetate; the resulting solution was washed with a 10% aqueous solution of citric acid, a saturated aqueous solution of sodium hydrogen carbonate and saturated saline, and dried with anhydrous sodium sulfate. After the desiccant was filtered off, the filtrate was concentrated under reduced pressure, after which it was solidified by the addition of ether-hexane to yield 134 mg (85.5%) of the title compound.

Elemental analysis

Calculated (+0.1 $H_2O$): C, 58.49; H, 7.31; N, 7.06 Found: C, 58.23; H, 7.02; N, 7.28

EXAMPLE 14

Preparation of 1-Naphthalenesulfonyl-Val-Ala-HN—CH(CHO)—$CH_2CH_2CO_2H$ 120 mg (0.202 mmol) of 1-Naphthalenesulfonyl-Val-Ala-HN—CH(CH($OCH_3$)$_2$)$CH_2CH_2CO_2Bu^t$ as obtained in Example 13 was dissolved in 2.4 ml of TFA and stirred for 35 minutes, after which 240 ml of water was added, followed by stirring for 5 hours. After the solution was concentrated under reduced pressure, the resulting oily substance was solidified by the addition of ether to yield 90.5 mg (91.1%) of the title compound.

Elemental analysis

Calculated (+0.5 $H_2O$): C, 55.19; H, 6.04; N, 8.39 Found: C, 55.06; H, 6.18; N, 8.38

EXAMPLE 15

Preparation of 2-Naphthalenesulfonyl-Val-Ala-HN—CH(CH(OCH$_3$)$_2$)CH$_2$CH$_2$CO$_2$Bu$^t$ 100 mg (0.264 mmol) of 2-Naphthalenesulfonyl-Val-Ala-OH, 61.7 mg (0.264 mmol) of H$_2$N—CH(CH(OCH$_3$)$_2$)CH$_2$CH$_2$CO$_2$Bu$^t$ as obtained in Reference Example 9 and 35.7 mg (0.264 mmol) of HOBt were dissolved in 1.5 ml of dimethylformamide; 50.7 mg (0.264 mmol) of WSCD·HCl was added at 0° C. The reaction mixture was stirred at 0° C. for 10 minutes and 28° C. overnight. After completion of the reaction, the reaction mixture was concentrated under reduced pressure; the residue was dissolved in ethyl acetate; the resulting solution was washed with a 10% aqueous solution of citric acid, a saturated aqueous solution of sodium hydrogen carbonate and saturated saline, and dried with anhydrous sodium sulfate. After the desiccant was filtered off, the filtrate was concentrated under reduced pressure, after which it was solidified by the addition of ether-hexane to yield 127 mg (81.1%) of the title compound.

Elemental analysis

Calculated (+0.2 H$_2$O): C, 58.31; H, 7.32; N, 7.03 Found: C, 58.17; H, 7.09; N, 7.28

EXAMPLE 16

Preparation of 2-Naphthalenesulfonyl-Val-Ala-HN—CH(CHO)—CH$_2$CH$_2$CO$_2$H 120 mg (0.202 mmol) of 2-Naphthalenesulfonyl-Val-Ala-HN—CH(CH(OCH$_3$)$_2$)CH$_2$CH$_2$CO$_2$Bu$^t$ as obtained in Example 15 was dissolved in 2.4 ml of TFA and stirred for 35 minutes, after which 240 ml of water was added, followed by stirring for 5 hours. After the solution was concentrated under reduced pressure, the resulting oily substance was solidified by the addition of ether to yield 93.6 mg (94.3%) of the title compound.

Elemental analysis

Calculated (+0.5 H$_2$O): C, 55.19; H, 6.04; N, 8.39 Found: C, 55.10; H, 6.12; N, 8.48

EXAMPLE 17

Preparation of 1-(Hydroxy)-2-naphthoyl-Val-Ala-HN—CH(CH(OCH$_3$)$_2$)CH$_2$CH$_2$CO$_2$Bu$^t$ 149 mg (0.415 mmol) of 1-(Hydroxy)-2-naphthoyl-Val-Ala-OH, 96.8 mg (0.415 mmol) of H$_2$N—CH(CH(OCH$_3$)$_2$)CH$_2$CH$_2$CO$_2$Bu$^t$ as obtained in Reference Example 9 and 74.3 mg (0.415 mmol) of HONB were dissolved in 2 ml of dimethylformamide; 79.5 mg (0.415 mmol) of WSCD·HCl was added at 0° C. The reaction mixture was stirred at 0° C. for 1 hour and 28° C. for 16 hours. After completion of the reaction, ethyl acetate was added; the solution was washed with water, a saturated aqueous solution of sodium hydrogen carbonate and saturated saline, and dried with anhydrous sodium sulfate. After the desiccant was filtered off, the filtrate was concentrated under reduced pressure, after which it was purified by silica gel column chromatography (4 g silica gel, hexane:ethyl acetate=1:1) to yield 128 mg (53.7%) of the title compound.

Elemental analysis

Calculated (+H$_2$O): C, 60.90; H, 7.67; N, 7.10 Found: C, 60.48; H, 7.38; N, 7.50

EXAMPLE 18

Preparation of 1-(Hydroxy)-2-naphthoyl-Val-Ala-HN—CH(CHO)—CH$_2$CH$_2$CO$_2$H 110 mg (0.192 mmol) of 1-(Hydroxy)-2-naphthoyl-Val-Ala-HN—CH(CH(OCH$_3$)$_2$)CH$_2$CH$_2$CO$_2$Bu$^t$ as obtained in Example 17 was dissolved in 2.3 ml of trifluoroacetic acid and stirred for 55 minutes, after which 230 ml of water was added, followed by stirring for 110 minutes. After the solution was concentrated under reduced pressure, the resulting oily substance was solidified by the addition of ether and hexane to yield 92.4 mg (constant) of the title compound.

Elemental analysis

Calculated (+1.8 H$_2$O): C, 57.20; H, 6.52; N, 8.34 Found: C, 56.85; H, 6.35; N, 8.77

EXAMPLE 19

Preparation of 3-(Eydroxy)-2-naphthoyl-Val-Ala-HN—CH(CH(OCH$_3$)$_2$)CH$_2$CH$_2$CO$_2$Bu$^t$ 163 mg (0.454 mmol) of 3-(Hydroxy)-2-naphthoyl-Val-Ala-OH, 117 mg (0.500 mmol) of H$_2$N—CH(CH(OCH$_3$)$_2$)CH$_2$CH$_2$CO$_2$Bu$^t$ as obtained in Reference Example 9 and 81.4 mg (0.454 mmol) of HONB were dissolved in 2 ml of dimethylformamide; 87.1 mg (0.454 mmol) of WSCD·HCl was added at 0° C. The reaction mixture was stirred at 0° C. for 20 minutes and 28° C. for 22.5 hours. After completion of the reaction, ethyl acetate was added; the solution was washed with water, a saturated aqueous solution of sodium hydrogen carbonate and saturated saline, and dried with anhydrous. sodium sulfate. After the desiccant was filtered off, the filtrate was concentrated under reduced pressure, after which it was solidified by the addition of ether and hexane to yield 172 mg (66.0%) of the title compound.

Elemental analysis

Calculated: C, 62.81; H, 7.55; N, 7.32 Found: C, 62.50; H, 7.48; N, 7.28

EXAMPLE 20

Preparation of 3-(Hydroxy)-2-naphthoyl-Val-Ala-HN—CH(CHO)—CH$_2$CH$_2$CO$_2$H 130 mg (0.227 mmol) of 3-(Hydroxy)-2-naphthoyl-Val-Ala-HN—CH(CH(OCH$_3$)$_2$)CH$_2$CH$_2$CO$_2$Bu$^t$ as obtained in Example 19 was dissolved in 3 ml of TFA and stirred for 1 hour, after which 300 ml of water was added, followed by stirring for 40 minutes. After the solution was concentrated under reduced pressure; the resulting oily substance was solidified by the addition of ether and hexane to yield 105 mg (98.3%) of the title compound.

Elemental analysis

Calculated (+H$_2$O): C, 58.89; H, 6.38; N, 8.58 Found: C, 58.88; H, 6.19; N, 8.41

EXAMPLE 21

Preparation of 2-Quinaldyl-Val-Ala-HN—CH(CH(OCH$_3$)$_2$)—CH$_2$CH$_2$CO$_2$Bu$^t$ 170 mg (0.495 mmol) of 2-Quinaldyl-Val-Ala-OH, 139 mg (0.594 mmol) of H$_2$N—CH(CH(OCH$_3$)$_2$)CH$_2$CH$_2$CO$_2$Bu$^t$ as obtained in Reference Example 9 and 66.9 mg (0.495 mmol) of HOBt were dissolved in 2.5 ml of dimethylformamide; 94.9 mg (0.495 mmol) of WSCD·HCl was added at 0° C. The reaction mixture was stirred at 0° C. for 10 minutes and 28° C. for 17 hours. After completion of the reaction, ethyl acetate was added; the solution was washed with a saturated aqueous solution of sodium hydrogen carbonate and saturated saline, and dried with anhydrous sodium sulfate. After the desiccant was filtered off, the filtrate was concentrated under reduced pressure to yield 250 mg (90.3%) of the title compound as an oily substance.

Elemental analysis

Calculated (+0.3 H$_2$O): C, 61.72; H, 7.61; N, 9.93 Found: C, 61.71; A, 7.52; N, 9.85

EXAMPLE 22

Preparation of 2-Quinaldyl-Val-Ala-HN—CH(CHO)CH$_2$CH$_2$CO$_2$H 150 mg (0.268 mmol) of 2-Quinaldyl-Val-Ala-HN—CH(CH(OCH$_3$)$_2$)CH$_2$CH$_2$CO$_2$Bu$^t$ as obtained in Example 21 was dissolved in 3 ml of TFA and stirred for 70 minutes, after which 0.3 ml of water was added. After the solution was concentrated under reduced pressure, the resulting residue was solidified by the addition of ether to yield 102 mg (82.8%) of the title compound.

Elemental analysis

Calculated (+1.3 $H_2O$): C, 57.56; H, 6.43; N, 11.67 Found: C, 57.72; H, 6.13; N, 11.31

EXAMPLE 23

Preparation of 3-Quinaldyl-Val-Ala-HN—CH(CH(OCH$_3$)$_2$)CH$_2$CH$_2$CO$_2$Bu$^t$ 200 mg (0.582 mmol) of 3-Quinaldyl-Val-Ala-OH, 163 mg (0.699 mmol) of H$_2$N—CH(CH(OCH$_3$)$_2$)CH$_2$CH$_2$CO$_2$Bu$^t$ as obtained in Reference Example 9 and 78.7 mg (0.582 mmol) of HOBt were dissolved in 3 ml of dimethylformamide; 112 mg (0.582 mmol) of WSCD·HCl was added at 0° C. The reaction mixture was stirred at 0° C. for 1 hour and 28° C. for 22 hours. After completion of the reaction, ethyl acetate was added; the solution was washed with a saturated aqueous solution of sodium hydrogen carbonate and saturated saline, and dried with anhydrous sodium sulfate. After the desiccant was filtered off, the filtrate was concentrated under reduced pressure to yield 257 mg (79.1%) of the title compound as an oily substance.

Elemental analysis

Calculated: C, 62.35; H, 7.58; N, 10.03 Found: C, 62.16; H, 7.50; N, 10.08

EXAMPLE 24

Preparation of 3-Quinaldyl-Val-Ala-HN—CH(CHO)CH$_2$CH$_2$CO$_2$H·TFA 200 mg (0.358 mmol) of 3-Quinaldyl-Val-Ala-HN—CH(CH(OCH$_3$)$_2$)CH$_2$CH$_2$CO$_2$Bu$^t$ as obtained in Example 23 was dissolved in 4 ml of TFA and stirred for 2.5 hours, after which 0.4 ml of water was added. After the solution was concentrated under reduced pressure, the resulting residue was solidified by the addition of ether to yield 165 mg (constant) of the title compound.

Elemental analysis

Calculated: C, 52.63; H, 5.12; N, 9.82 Found: C, 53.00; H, 5.46; N, 9.65

EXAMPLE 25

Preparation of 6-(Hydroxy)-2-naphthalenesulfonyl-Val-Ala-HN—CH(CH(OCH$_3$)$_2$)CH$_2$CH$_2$CO$_2$Bu$^t$ 154 mg (0.376 mmol) of 6-(Hydroxy)-2-naphthalenesulfonyl-Val-Ala-OH, 87.7 mg (0.376 mmol) of H$_2$N—CH(CH(OCH$_3$)$_2$)CH$_2$CH$_2$CO$_2$Bu$^t$ as obtained in Reference Example 9 and 50.8 mg (0.376 mmol) of HOBt were dissolved in 2 ml of dimethylformamide; 72.1 mg (0.376 mmol) of WSCD·HCl was added at 0° C. The reaction mixture was stirred at 0° C. for 1 hour and 28° C. for 17 hours. After completion of the reaction, ethyl acetate was added; the solution was washed with water, a saturated aqueous solution of sodium hydrogen carbonate and saturated saline, and dried with anhydrous sodium sulfate. After the desiccant was filtered off, the filtrate was concentrated under reduced pressure, after which it was solidified by the addition of ether and hexane to yield 151 mg (64.3%) of the title compound.

Elemental analysis

Calculated: C, 57.13; H, 7.11; N, 6.89 Found: C, 56.82; H, 6.87; N, 7.08

EXAMPLE 26

Preparation of 6-(Hydroxy)-2-naphthalenesulfonyl-Val-Ala-HN—CH(CHO)CH$_2$CH$_2$CO$_2$H 130 mg (0.208 mmol) of 6-(Hydroxy)-2-naphthalenesulfonyl-Val-Ala-HN—CH(CH(OCH$_3$)$_2$)CH$_2$CH$_2$CO$_2$Bu$^t$ as obtained in Example 25 was dissolved in 3 ml of TFA and stirred for 80 minutes, after which 300 ml of water was added, followed by stirring for 100 minutes. After the solution was concentrated under reduced pressure, the resulting oily substance was solidified by the addition of ether and hexane to yield 115 mg (constant) of the title compound.

Elemental analysis

Calculated (+0.7 $H_2O$): C, 53.11; H, 5.89; N, 8.08 Found: C, 53.13; H, 6.06; N, 7.78

EXAMPLE 27

Preparation of 4-Phenylbenzoyl-Val-Ala-HN—CH(CH(OCH$_3$)$_2$)—CH$_2$CH$_2$CO$_2$Bu$^t$ 170 mg (0.461 mmol) of 4-Phenylbenzoyl-Val-Ala-OH, 129 mg (0.554 mmol) of H$_2$N—CH(CH(OCH$_3$)$_2$)CH$_2$CH$_2$CO$_2$Bu$^t$ as obtained in Reference Example 9 and 62.3 mg (0.461 mmol) of HOBt were dissolved in 2.5 ml of dimethylformamide; 88.4 mg (0.461 mmol) of WSCD·HCl was added at 0° C. The reaction mixture was stirred at 0° C. for 10 minutes and 28° C. for 16 hours. After completion of the reaction, the reaction mixture was concentrated under reduced pressure; a saturated aqueous solution of sodium hydrogen carbonate was added to the residue; the resulting precipitate was collected by filtration, washed thoroughly with water to yield 225 mg (83.7%) of the title compound.

Elemental analysis

Calculated: C, 65.84; H, 7.77; N, 7.20 Found: C, 65.56; H, 7.69; N, 7.49

EXAMPLE 28

Preparation of 4-Phenylbenzoyl-Val-Ala-HN—CH(CHO)CH$_2$CH$_2$CO$_2$H 150 mg (0.258 mmol) of 4-Phenylbenzoyl-Val-Ala-HEN—CH(CH(OCH$_3$)$_2$)CH$_2$CH$_2$CO$_2$Bu$^t$ as obtained in Example 27 was dissolved in 3 ml of TFA and stirred for 70 minutes, after which 0.3 ml of water was added. After the solution was concentrated under reduced pressure, the resulting residue was solidified by the addition of ether to yield 120 mg (96.8%) of the title compound.

Elemental analysis

Calculated (+$H_2O$): C, 62.51; H, 6.66; N, 8.41 Found: C, 62.28; H, 6.41; N, 8.68

EXAMPLE 29

Preparation of Fmoc-Val-Ala-NH—CH[CH(OCH$_3$)$_2$]CH$_2$CH$_2$COOBu$^t$ 370 mg of Z—NH—CH[CH(OCH$_3$)$_2$]CH$_2$CH$_2$COOBu$^t$ was dissolved in 2 ml of tetrahydrofuran and reduced in a hydrogen stream for 2 hours with palladium black as a catalyst. After the catalyst was removed, the solution was concentrated under reduced pressure to yield NH$_2$—CH[CH(OCH$_3$)$_2$]CH$_2$CH$_2$COOBu$^t$, which was then dissolved in 5 ml of dimethylformamide; after 410 mg of Fmoc-Val-Ala-OH was added to this solution, 135 mg of HOBt and 200 mg of WSCl·HCl were added with stirring at 0° C. After stirring at 0° C. for 1 hour and 28° C. for 14 hours, the solution was concentrated under reduced pressure. Water was added to the residue to yield a white powder, which was then thoroughly washed with water to yield 250 mg (40.0%) of the title compound.

Elemental analysis

Calculated (+0.4 $H_2O$): C, 64.52; H, 7.61; N, 6.64 Found: C, 64.24; H, 7.39; N, 6.94

EXAMPLE 30
Preparation of Fmoc-Val-Ala-HN—CH(CHO)CH$_2$CH$_2$COOH

To 90 mg of Fmoc-Val-Ala-HN—CH[CH(OCH$_3$)$_2$]CH$_2$CH$_2$COOBu$^t$ as obtained in Example 29, 2 ml of trifluoroacetic acid and 200 μl of water were added; the mixture was kept standing at 28° C. for 4 hours. After the solution was concentrated under reduced pressure, the resulting residue was solidified by the addition of ether-hexane to yield 65 mg of the title compound as a white powder.

Elemental analysis

Calculated (+H$_2$O): C, 62.10; H, 6.51; N, 7.76 Found: C, 61.86; H, 6.46; N, 7.76

EXAMPLE 31
Preparation of Z—NH—NH—CH$_2$CH$_2$COOBu$^t$ 13.2 g of Z—NH—NH$_2$ and 12 ml of CH$_2$=CH—COOBu$^t$ were dissolved in 2 ml of DMF, followed by stirring at 85° C. for 16 hours. This reaction mixture was purified through a silica gel column (3.2 cm dia.×38 cm) with ethyl acetate:hexane (1:5 to 1:2) as an eluent; the fraction containing the desired product was concentrated under reduced pressure; the residue was solidified by the addition of hexane to yield 7.89 g of the desired product as a white powder.

Elemental analysis

Calculated: C, 61.21; H, 7.53; N, 9.52 Found: C, 61.12; H, 7.37; N, 9.37

EXAMPLE 32
Preparation of NH$_2$-HN—CH$_2$CH$_2$COOBu$^t$·2pTosOH 1.5 g of Z—NH—NH—CH$_2$CH$_2$—COOBu$^t$ was dissolved in 50 ml of tetrahydrofuran, and reduced in a hydrogen stream for 2 hours with palladium black as a catalyst. After the catalyst was removed, the solution was concentrated under reduced pressure and solidified by the addition of ether to yield 2.35 g of NH$_2$—NH—CH$_2$CH$_2$COOBu$^t$·2pTosOH as a white powder.

Elemental analysis

Calculated (+H$_2$O): C, 48.26; A, 6.56; N, 5.36 Found: C, 48.18; H, 6.26; N, 5.49

EXAMPLE 33
Preparation of 2-Naphthoyl-Val-Ala-NH—NH—CH$_2$CH$_2$COOBu$^t$ 1.72 g of 2-Naphthoyl-Val-Ala-OH and 3.53 g of NH$_2$—NH—CH$_2$CH$_2$COOBu$^t$·2pTosOE were dissolved in 25 ml of DMF; while this solution was stirred at 0° C., 2.4 ml of diisopropylethylamine, 0.98 g of HONB and 1.01 g of WSCD·HCl were added. After stirring at 0° C. for 1 hour and 28° C. for 14 hours, ethyl acetate was added; the solution was washed with a saturated aqueous sodium hydrogen carbonate and saturated saline. After being dried with anhydrous sodium sulfate, the organic layer was concentrated under reduced pressure; the residue was solidified by the addition of ether to yield 1.70 g of the desired product as a white powder.

Elemental analysis

Calculated: C, 64.44; H, 7.49; N, 11.56 Found: C, 64.25; E, 7.32; N, 11.36

EXAMPLE 34
Preparation of 2-Naphthoyl-Val-Ala-NH—N(COCH=CH$_2$)—CH$_2$CH$_2$COOBu$^t$ 100 mg of 2-Naphthoyl-Val-Ala-NH—NH—CH$_2$CH$_2$COOBu$^t$ was dissolved in 1 ml of DMF; while this solution was stirred at 0° C., 28 μl of NMM and 20 μl of acryloyl chloride were added. After stirring at 0° C. for 1 hour, ethyl acetate was added; the solution was washed with a 10% aqueous citric acid, a saturated aqueous sodium hydrogen carbonate and saturated saline. After being dried with anhydrous sodium sulfate, the organic layer was concentrated under reduced pressure; the residue was solidified by the addition of ether to yield 107 mg of the desired product as a white powder.

Elemental analysis

Calculated: C, 64.55; H, 7.28; N, 10.38 Found: C, 64.25; H, 7.16; N, 10.41

EXAMPLE 35
Preparation of 2-Naphthoyl-Val-Ala-NH—N(COCH=CH$_2$)—CH$_2$CH$_2$COOH 95 mg of 2-Naphthoyl-Val-Ala-NH-N(COCH=CH$_2$)—CH$_2$CH$_2$COOBu$^t$ was dissolved in 2 ml of TFA and kept standing at 25° C. for 30 minutes. This solution was concentrated under reduced pressure; the residue was solidified by the addition of ether to yield 64 mg of the desired product as a white powder.

Elemental analysis

Calculated (+0.5 H$_2$O): C, 60.96; H, 6.55; N, 11.37 Found: C, 61.26; H, 6.29; N, 11.43

EXAMPLE 36
Preparation of 2-Naphthoyl-Val-Ala-NH—N(COCH$_2$Cl)—CH$_2$CH$_2$COOH In the same manner as in Examples 34 and 35, 37 mg of the title compound was obtained using 60 mg of 2-Naphthoyl-Val-Ala-NH—NH—CH$_2$CH$_2$COOBu$^t$ and 11.8 μl of ClCH$_2$COCl.

Elemental analysis

Calculated (+H$_2$O): C, 55.12; H, 5.97; N, 10.71 Found: C, 55.44; H, 6.03; N, 10.46

EXAMPLE 37
Preparation of 2-Naphthoyl-Val-Ala-NH—N(COCOOCH$_2$CH$_3$)—CH$_2$CH$_2$COOBu$^t$ In the same manner as in Example 34, 121 mg of the title compound was obtained using 100 mg of 2-Naphthoyl-Val-Ala-NH—NH—CH$_2$CH$_2$COOBu$^t$ and 28 μl of ethyloxalyl chloride.

Elemental analysis

Calculated: C, 61.63; H. 6.90; N, 9.58 Found: C, 61.61; H, 6.99; N, 9.69

EXAMPLE 38
Preparation of 2-Naphthoyl-Val-Ala-NH—N(COCOOCH$_2$CH$_3$)—CH$_2$CH$_2$COOH In the same manner as in Example 35, 79 mg of the title compound was obtained using 110 mg of 2-Naphthoyl-Val-Ala-NH—N(COCOOCH$_2$CH$_3$)—CH$_2$CH$_2$COOBu$^t$.

Elemental analysis

Calculated (+0.8 H$_2$O): C, 57.51; H, 6.24; N, 10.31 Found: C, 57.92; H, 6.26; N, 9.89

EXAMPLE 39
Preparation of 2-Naphthoyl-Val-Ala-NH—N(COCH=CH—C$_6$H$_5$)—CH$_2$CH$_2$COOBu$^t$ In the same manner as in Example 34, 128 mg of the title compound was obtained using 100 mg of 2-Naphthoyl-Val-Ala-NH—NH—CH$_2$CH$_2$COOBu$^t$ and 40 mg of cinnamic acid chloride.

Elemental analysis

Calculated: C, 68.27; H, 7.04; N, 9.10 Found: C, 68.23; H, 6.97; N, 8.63

EXAMPLE 40
Preparation of 2-Naphthoyl-Val-Ala-NH-N(COCH=CH-$C_6H_5$)—$CH_2CH_2COOH$ In the same manner as in Example 35, 72 mg of the title compound was obtained using 100 mg of 2-Naphthoyl-Val-Ala-NH-N(COCH=CH-$C_6H_5$)—$CH_2CH_2COOBu^t$.

Elemental analysis

Calculated (+0.7 $H_2O$): C, 65.07; H, 6.41; N, 9.79 Found: C, 64.94; A, 6.27; N, 10.09

EXAMPLE 41
Preparation of 2-Naphthoyl-Val-Ala-NH—N($COCH_2CH_2C_6H_5$)—$CH_2CH_2COOBu^t$ In the same manner as in Example 34, 176 mg of the title compound was obtained using 100 mg of 2-Naphthoyl-Val-Ala-NH—NH—$CH_2CH_2COOBu^t$ and 54 μl of phenylpropionic acid chloride.

Elemental analysis

Calculated (+0.25 $H_2O$): C, 67.56; H, 7.37; N, 9.00 Found: C, 67.27; H, 7.24; N, 9.12

EXAMPLE 42
Preparation of 2-Naphthoyl-Val-Ala-NH—N($COCH_2CH_2C_6H_5$)—$CH_2CH_2COOH$ In the same manner as in Example 35, 111 mg of the title compound was obtained using 140 mg of 2-Naphthoyl-Val-Ala-NH-N($COCH_2CH_2C_6H_5$)—$CH_2CH_2COOBu^t$.

Elemental analysis

Calculated (+0.75 $H_2O$): C, 64.74; H, 6.75; N, 9.74 Found: C, 64.82; A, 6.62; N, 10.03

EXAMPLE 43
Preparation of 2-Naphthoyl-Val-Ala-Aib-NH—NH—$CH_2CH_2COOBu^t$

In the same manner as in Example 33, 391 mg of the title compound was obtained using 376 mg of 2-Naphthoyl-Val-Aib-OH and 606 mg of $NH_2$—NH—$CH_2CH_2COOBu^t$·2pTosOH.

Elemental analysis

Calculated (+0.1 $H_2O$): C, 64.80; H, 7.69; N, 11.20 Found: C, 64.87; H, 7.96; N, 10.90

EXAMPLE 44
Preparation of 2-Naphthoyl-Val-Ala-NH—N[$COCH_2OP(O)(C_6H_5)_2$]—$CH_2CH_2COOH$ 121 mg of 2-Naphthoyl-Val-Ala-NH-N($COCH_2Br$)-$CH_2CH_2COOBu^t$ as synthesized in the same manner as in Example 34, 52.4 mg of diphenylphosphinic acid and 35 mg of KF were dissolved in 2 ml of DMF, followed by reaction at 65° C. for 16 hours. Ethyl acetate was added; the organic layer was washed with a saturated aqueous sodium hydrogen carbonate and saturated saline. After being dried with anhydrous sodium sulfate, the organic layer was concentrated under reduced pressure; the residue was purified through a silica gel column (1.7 cm dia.×4.5 cm) with chloroform containing 2% methanol as an eluent; the fraction containing the desired product was concentrated under reduced pressure to yield Naphthoyl-Val-Ala-NH-N[$COCH_2OP(O)(C_6H_5)_2$]-$CH_2CH_2COOBu^t$ as a colorless oil, which was then dissolved in 1 ml of TFA and kept standing at 25° C. for 30 minutes. The solution was concentrated under reduced pressure; the residue was powdered by the addition of ether to yield 36 mg of the desired product as a white powder.

Elemental analysis

Calculated (+1.5 $H_2O$): C, 60.58; H, 5.93; N, 7.85 Found: C, 60.37; H, 5.85; N, 8.38

EXAMPLE 45
Preparation of 2-Naphthoyl-Val-Ala-NH-N[$COCH_2OCO$ (2',6'-$Cl_2$-$C_6H_3$) ]-$CH_2CH_2COOH$ In the same manner as in Example 44, 33 mg of the title compound was obtained using 121 mg of 2-Naphthoyl-Val-Ala-NH-N($COCH_2Br$)-$CH_2CH_2COOBu^t$ and 46 mg of 2,6-di-chlorobenzoic acid.

Elemental analysis

Calculated (+0.75 $H_2O$): C, 55.32; H, 5.02; N, 8.32 Found: C, 55.35; H, 5.27; N, 8.67

EXAMPLE 46
Preparation of 2-Naphthoyl-Val-Aib-NH-N[$COCH_2OP(O)(C_6H_5)_2$]—$CH_2CH_2COOH$ In the same manner as in Example 44, 65 mg of the title compound was obtained using 186 mg of 2-Naphthoyl-Val-Aib-NH-N($COCH_2Br$)-$CH_2CH_2COOBu^t$ and 79 mg of diphenyl-phosphinic acid.

Elemental analysis

Calculated (+$H_2O$): C, 61.83; H, 6.03; N, 7.80 Found: C, 61.53; H, 6.00; N, 7.90

EXAMPLE 47
Preparation of Fmoc-Val-S-CH($CH_3$)-CONH—CH[CH($OCH_3$)$_2$]—$CH_2CH_2COOBu^t$ 3.4 g of Fmoc-Val-OH was dissolved in 100 ml of acetonitrile; while this solution was stirred at 0° C., 1.8 g of HONB and 2.06 g of DCC were added. After stirring at 0° C. for 1 hour and 28° C. for 14 hours, the insoluble substances were filtered off. After 0.9 ml of 2-mercaptopropionic acid and 1.4 ml of triethylamine were added to the filtrate, the mixture was stirred at 28° C. for 14 hours. Solvent was evaporated under reduced pressure. To the residue, ether was added; the organic layer was washed with water, 10% aqueous citric acid and saturated saline. After being dried with anhydrous sodium sulfate, the organic layer was concentrated under reduced pressure; the residue was solidified by the addition of hexane to yield Fmoc-Val-S-CH($CH_3$)—COOH as a white powder.

370 mg of Z—NH—CH[CH($OCH_3$)$_2$]$CH_2CH_2COOBu^t$ as obtained in Reference Example 8 was dissolved in 2 ml of tetrahydrofuran, and reduced in a hydrogen stream for 2 hours with palladium black as a catalyst. After the catalyst was removed, the solution was concentrated under reduced pressure to yield $NH_2$—CH[CH($OCH_3$)$_2$]$CH_2CH_2COOBu^t$ as a colorless oily substance, which was then dissolved in 5 ml of acetonitrile. After 450 mg of Fmoc-Val-S-CH($CH_3$)—COOH, as obtained above, was added to the solution, 140 mg of HOBt and 210 mg of DCC were added while the solution was stirred at 0° C. After stirring at 0° C. for 1 hour and 28° C. for 14 hours, the insoluble substances were filtered off; the filtrate was concentrated under reduced pressure. To the residue, ether was added; the organic layer was washed with saturated aqueous sodium hydrogen carbonate and saturated saline. After being dried with anhydrous sodium sulfate, the organic layer was concentrated under reduced pressure; the residue was solidified by the addition of hexane to yield a white powder, which was then purified through a silica gel column (1.7 cm dia.×8.5 cm) with chloroform as an eluent; the fraction containing the desired product was concentrated under reduced pressure; the residue was triturated in hexane to yield 143 mg (22.2%) of the title compound as a white powder.

Elemental analysis

Calculated (+0.5 $H_2O$): C, 63.09; H, 7.24; N, 4.33 Found: C, 63.22; H, 7.27; N, 4.46

EXAMPLE 48

Preparation of Fmoc-Val-S-CH($CH_3$)—CONH—CH(CHO) $CH_2CH_2COOH$

To 100 mg of Fmoc-Val-S-CH($CH_3$)—CONH—CH[CH (O$CH_3$)$_2$]$CH_2CH_2$COOBu$^t$ as obtained in Example 47, 2 ml of trifluoroacetic acid and 200 μl of water were added; this mixture was kept standing at 28° C. for 4 hours. After being concentrated under reduced pressure, the residue was triturated in ether-hexane to yield 100 mg of the title compound as a white powder.

Elemental analysis

Calculated (+0.5 $H_2O$): C, 61.19; H, 6.05; N, 5.10 Found: C, 61.24; H, 6.29; N, 4.82

EXAMPLE 49

Preparation of Fmoc-Val-S-$CH_2$-CONH—CH[CH(O$CH_3$)$_2$] $CH_2CH_2$COOBu$^t$ 3.4 g of Fmoc-Val-OH was dissolved in 100 ml of acetonitrile; while this solution was stirred at 0° C., 1.8 g of HONB and 2.06 g of DCC were added. After stirring at 0° C. for 1 hour and 28° C. for 14 hours, the insoluble substances were filtered off. After 1.0 ml of mercaptoacetic acid and 1.4 ml of triethylamine were added to the filtrate, followed by stirring at 28° C. for 14 hours, the mixture was concentrated under reduced pressure. To the residue, ether was added; the organic layer was washed with water, 10% aqueous citric acid and saturated saline. After being dried with anhydrous sodium sulfate, the organic layer was concentrated under reduced pressure; the residue was powdered by the addition of hexane to yield Fmoc-Val-S-CH($CH_3$)—COOH (3.75 g) as a white powder.

370 mg of Z—NH—CH[CH(O$CH_3$)$_2$]$CH_2CH_2$COOBu$^t$ as obtained in Reference Example 8 was dissolved in 2 ml of tetrahydrofuran, and reduced in a hydrogen stream for 2 hours with palladium black as a catalyst. After the catalyst was removed, the solution was concentrated under reduced pressure to yield $NH_2$-CH[CH(O$CH_3$)$_2$]$CH_2CH_2$COOBu$^t$ as a colorless oily substance, which was then dissolved in 5 ml of acetonitrile. After 414 mg of Fmoc-Val-S-$CH_2$-COOH as obtained above was added to the solution, 140 mg of HOBt and 210 mg of DCC were added while the solution was stirred at 0° C. After stirring at 0° C. for 1 hour and 28° C. for 14 hours, the insoluble substances were filtered off; the filtrate was concentrated under reduced pressure. To the residue, ether was added; the organic layer was washed with saturated aqueous sodium hydrogen carbonate and saturated saline. After being dried with anhydrous sodium sulfate, the organic layer was concentrated under reduced pressure; the residue was solidified by the addition of hexane to yield a white powder, which was then purified through a silica gel column (1.7 cm dia.×8.5 cm) with chloroform as an eluent; the fraction containing the desired product was concentrated under reduced pressure to yield 327 mg (52.0%) of the title compound as a white powder.

Elemental analysis

Calculated: C, 63.04; H, 7.05; N, 4.46 Found: C, 62.76; H, 7.04; N, 4.53

EXAMPLE 50

Preparation of Fmoc-Val-S-$CH_2$-CONH—CH(CHO) $CH_2CH_2COOH$

To 100 mg of Fmoc-Val-S-CH($CH_3$)—CONH—CH[CH (O$CH_3$)$_2$]—$CH_2CH_2$COOBu$^t$ as obtained in Example 49, 2 ml of trifluoroacetic acid and 200 μl of water were added; this mixture was kept standing at 28° C. for 4 hours. After being concentrated under reduced pressure, the residue was solidified by the addition of ether-hexane to yield 75.4 mg of the title compound as a white powder.

Elemental analysis

Calculated (+0.25 $H_2O$): C, 61.06; E, 5.79; N, 5.27 Found: C, 60.92; H, 6.04; N, 5.05

EXAMPLE 51

Preparation of Fmoc-Val-Aib-NH—CH[CH(O$CH_3$)$_2$] $CH_2CH_2$COOBu$^t$ 370 mg of Z—NH—CH[CH(O$CH_3$)$_2$]$CH_2CH_2$COOBu$^t$ as obtained in Reference Example 8 was dissolved in 2 ml of tetrahydrofuran and reduced in a hydrogen stream for 2 hours with palladium black as a catalyst. After the catalyst was removed, the solution was concentrated under reduced pressure to yield $NH_2$-CH[CH(O$CH_3$)$_2$]$CH_2CH_2$COOBu$^t$ as a colorless oily substance, which was then dissolved in 5 ml of dimethylformamide. After 425 mg of Fmoc-Val-Aib-OH was added to the solution, 135 mg of HOBt and 200 mg of WSCD·HCl were added while the solution was stirred at 0° C. After stirring at 0° C. for 1 hour and 28° C. for 14 hours, the mixture was concentrated under reduced pressure. To the residue, ethyl acetate was added; the organic layer was washed with saturated aqueous sodium hydrogen carbonate and saturated saline. After being dried with anhydrous sodium sulfate, the organic layer was concentrated under reduced pressure; the residue was triturated in hexane to yield a white powder, which was then purified through a silica gel column (1.7 cm dia.×8.5 cm) with chloroform as eluent; the fraction containing the desired product was concentrated under reduced pressure; the residue was solidified by the addition of hexane to yield 370 mg of the title compound as a white powder.

Elemental analysis

Calculated (+0.25 $H_2O$): C, 65.25; H, 7.74; N, 6.52 Found: C, 64.96; H, 7.75; N, 6.33

EXAMPLE 52

Preparation of Fmoc-Val-Aib-NH—CH(CHO) $CH_2CH_2COOH$

To 210 mg of Fmoc-Val-Aib-NH—CH[CH(O$CH_3$)$_2$] $CH_2CH_2$COOBu$^t$ as obtained in Example 51, 4 ml of trifluoroacetic acid and 200 μl of water were added; this mixture was kept standing at 28° C. for 4 hours. After being concentrated under reduced pressure, the residue was triturated in ether-hexane to yield 157 mg of the title compound as a white powder.

Elemental analysis

Calculated (+0.25 $H_2O$): C, 64.25; H, 6.60; N, 5.75 Found: C, 64.23; H, 6.77; N, 7.53

EXAMPLE 53

Preparation of Fmoc-Aib-Aib-NH—CH[CH(O$CH_3$)$_2$] $CH_2CH_2$COOBu$^t$ 200 mg of Z—NH—CH[CH(O$CH_3$)$_2$]$CH_2CH_2$COOBu$^t$ as obtained in Reference Example 8 was dissolved in 2 ml of tetrahydrofuran and reduced in a hydrogen stream for 2 hours with palladium black as a catalyst. After the catalyst was removed, the solution was concentrated under reduced pressure to yield $NH_2$-CH[CH(O$CH_3$)$_2$]$CH_2CH_2$COOBu$^t$ as a colorless oily substance, which was then dissolved in 5 ml of dimethylformamide. After 180 mg of Fmoc-Aib-Aib-OH was added to the solution, 68 mg of HOBt and 100 mg of WSCD·HCl were added while the solution was stirred at 0° C. After stirring at 0° C. for 1 hour and 28° C. for 14 hours, the mixture was concentrated under reduced pressure. To the residue, ethyl acetate was added; the organic layer was washed with saturated aqueous sodium hydrogen carbonate and saturated saline. After being dried with anhydrous sodium sulfate, the organic layer was concentrated under reduced pressure; the residue was triturated in hexane to yield a white powder, which was then purified through a silica gel column (1.7 cm dia.×8.5 cm) with chloroform as eluent; the fraction containing the desired product was concentrated under reduced pressure; the residue was solidified by the addition of hexane to yield 248 mg of the title compound as a white powder.

Elemental analysis

Calculated (+0.25 E20): C, 64.33; H, 7.62; N, 6.62 Found: C, 64.36; H, 7.76; N, 6.62

EXAMPLE 54

Preparation of Fmoc-Aib-Aib-NH—CH(CHO)CH$_2$CH$_2$COOH

To 110 mg of Fmoc-Aib-Aib-NH—CH[CH(OCH$_3$)$_2$]CH$_2$CH$_2$COOBu$^t$ as obtained in Example 53, 2 ml of trifluoroacetic acid and 100 μl of water were added; this mixture was kept standing at 28° C. for 4 hours. After being concentrated under reduced pressure, the residue was solidified by the addition of ether-hexane to yield 64 mg of the title compound as a white powder.

Elemental analysis

Calculated (+2 H$_2$O); C, 60.10; H, 6.66; N, 7.51 Found C, 60.03; H, 6.07; N, 7.50

EXAMPLE 55

Preparation of Fmoc-Val-S-CH(CH$_3$)—CONH—CH[CH(OCH$_3$)$_2$]—CH$_2$COOBu$^t$ 3.4 g of Fmoc-Val-OH was dissolved in 100 ml of acetonitrile; 1.8 g of HONB and 2.06 g of DCC were added at 0° C. while the solution was stirred. After the reaction mixture was stirred at 0° C. for 1 hour and 28° C. for 14 hours, the insoluble substances were filtered off. To the filtrate, 0.9 ml of 2-mercaptopropionic acid and 1.4 ml of triethylamine were added, followed by stirring at 28° C. for 14 hours, after which the mixture was concentrated under reduced pressure. To the residue, ether was added; the organic layer was washed with water, 10% aqueous citric acid and saturated saline. After being dried with anhydrous sodium sulfate, the organic layer was concentrated under reduced pressure; hexane was added to the residue to yield a white powder.

To 450 mg of Fmoc-NH—CH[CH(OCH$_3$)$_2$]CH$_2$COOBu$^t$ as obtained in Reference Example 21, 10 ml of dimethylformamide containing 20% piperidine was added; the mixture was kept standing at 28° C. for 1 hour. The mixture was concentrated under reduced pressure; the resulting residue was purified through a silica gel column (1.7 cm dia.×8.5 cm) with ethyl acetate:hexane (1:5) as an eluent; the fraction containing the desired product was concentrated under reduced pressure to yield NH$_2$-CH[CH(OCH$_3$)$_2$]CH$_2$COOBu$^t$ as a colorless oily substance. This substance was dissolved in 5 ml of acetonitrile; after 450 mg of Fmoc-Val-S-CH(CH$_3$)—COOH was added, 140 mg of HOBt and 210 mg of DCC were added at 0° C. while the solution was stirred. After the reaction mixture was stirred at 0° C. for 1 hour and 28° C. for 14 hours, the insoluble substances were filtered off; the filtrate was concentrated under reduced pressure. To the residue, ether was added; the organic layer was washed with saturated aqueous sodium hydrogen carbonate and saturated saline. After being dried with anhydrous sodium sulfate, the organic layer was concentrated under reduced pressure; hexane was added to the residue to yield a white powder, which was purified through a silica gel column (1.7 cm dia.×8.5 cm) with chloroform as an eluent; the fraction containing the desired product was concentrated under reduced pressure; hexane was added to the residue to yield 179 mg (28.5%) of the title com-pound as a white powder.

Elemental analysis

Calculated: C, 63.04; H, 7.05; N, 4.46 Found: C, 63.08; H, 6.93; N, 4.69

EXAMPLE 56

Preparation of Fmoc-Val-S-CH(CH$_3$)—CONH—CH(CHO)CH$_2$COOH

To 100 mg of Fmoc-Val-S-CH(CH$_3$)—CONH—CH[CH(OCH$_3$)$_2$]—CH$_2$COOBu$^t$ as obtained in Example 55, 2 ml of trifluoroacetic acid and 200 μl of water were added; the mixture was kept standing at 28° C. for 4 hours. After being concentrated under reduced pressure, the mixture was triturated in ether-hexane to yield 65 mg of the title compound as a white powder.

Elemental analysis

Calculated: C, 61.58; H, 5.74; N, 5.32 Found: C, 61.36; H, 5.93; N, 5.18

EXAMPLE 57

Preparation of Fmoc-Val-S-CH$_2$-CONH—CH[CH(OCH$_3$)$_2$]CH$_2$COOBu$^t$ 3.4 g of Fmoc-Val-OH was dissolved in 100 ml of acetonitrile; 1.8 g of HONB and 2.06 g of DCC were added at 0° C. while the solution was stirred. After the reaction mixture was stirred at 0° C. for 1 hour and 28° C. for 14 hours, the insoluble substances were filtered off. To the filtrate, 1.0 ml of mercaptopropionic acid and 1.4 ml of triethylamine were added, followed by stirring at 28° C. for 14 hours, after which the mixture was concentrated under reduced pressure. To the residue, ether was added; the organic layer was washed with water, 10% aqueous citric acid and saturated saline. After being dried with anhydrous sodium sulfate, the organic layer was concentrated under reduced pressure; hexane was added to the residue to yield a white powder (3.75 g).

To 440 mg of Fmoc-NH—CH[CH(OCH$_3$)$_2$]CH$_2$COOBu$^t$ as obtained in Reference Example 21, 10 ml of dimethylformamide containing 20% piperidine was added; the mixture was kept standing at 28° C. for 1 hour. The mixture was concentrated under reduced pressure; the resulting residue was purified through a silica gel column (1.7 cm dia.×8.5 cm) with ethyl acetate:hexane (1:5) as an eluent; the fraction containing the desired product was concentrated under reduced pressure to yield NH$_2$-CH[CH(OCH$_3$)$_2$]CH$_2$COOBu$^t$ as a colorless oily substance. This substance was dissolved in 5 ml of acetonitrile; after 414 mg of Fmoc-Val-S-CH$_2$-COOH as obtained in Example 6 was added, 140 mg of HOBt and 210 mg of DCC were added at 0° C. while the solution was stirred. After the reaction mixture was stirred at 0° C. for 1 hour and 28° C. for 14 hours, the insoluble substances were filtered off; the filtrate was concentrated under reduced pressure. To the residue, ether was added; the organic layer was washed with saturated aqueous sodium hydrogen carbonate and saturated saline. After being dried with anhydrous sodium sulfate, the organic layer was concentrated under reduced pressure; hexane was added to the residue to yield a white powder, which was purified through a silica gel column (1.7 cm dia.×8.5 cm) with chloroform as an eluent; the fraction containing the desired product was concentrated under reduced pressure; hexane was added to the residue to yield 343 mg (55.8%) of the title compound as a white powder.

Elemental analysis

Calculated: C, 62.52; H, 6.89; N, 4.56 Found: C, 62.43; H, 6.91; N, 4.58

EXAMPLE 58

Preparation of Fmoc-Val-S-CH$_2$-CONH—CH(CRO)CH$_2$COOH

To 120 mg of Fmoc-Val-S-CH$_2$-CONH—CH[CH(OCH$_3$)$_2$]—CH$_2$COOBu$^t$ as obtained in Example 57, 2 ml of trifluoroacetic acid and 200 μl of water were added; the mixture was kept standing at 28° C. for 4 hours. After being concentrated under reduced pressure, the residue was triturated in ether-hexane to yield 91.5 mg of the title compound as a white powder.

Elemental analysis

Calculated (+0.3 H$_2$O): C, 60.28; H, 5.58; N, 5.41 Found: C, 60.50; H, 5.88; N, 5.11

EXAMPLE 59

Preparation of Fmoc-Val-Aib-NH—CH[CH(OCH$_3$)$_2$]CH$_2$COOBu$^t$

To 440 mg of Fmoc-NH—CH[CH(OCH$_3$)$_2$]CH$_2$COOBu$^t$ as obtained in Reference Example 21, 10 ml of dimethylformamide containing 20% piperidine was added; the mixture was kept standing at 28° C. for 1 hour. The mixture was concentrated under reduced pressure; the resulting residue was purified through a silica gel column (1.7 cm dia.×8.5 cm) with ethyl acetate:hexane (1:5) as an eluent; the fraction containing the desired product was concentrated under reduced pressure to yield NH$_2$-CH[CH(OCH$_3$)$_2$]CH$_2$COOBu$^t$ as a colorless oily substance. This substance was dissolved in 5 ml of dimethylformamide; after 425 mg of Fmoc-Val-Aib-OH was added, 130 mg of HOBt and 200 mg of WSCD·HCl were added at 0° C. while the solution was stirred. After the reaction mixture was stirred at 0° C. for 1 hour and 28° C. for 14 hours, the filtrate was concentrated under reduced pressure. To the residue, ethyl acetate was added; the organic layer was washed with saturated aqueous sodium hydrogen carbonate and saturated saline. After being dried with anhydrous sodium sulfate, the organic layer was concentrated under reduced pressure; hexane was added to the residue to yield a white powder, which was purified through a silica gel column (1.7 cm dia.×8.5 cm) with chloroform as an eluent; the fraction containing the desired product was concentrated under reduced pressure; hexane was added to the residue to yield 390 mg of the title compound as a white powder.

Elemental analysis

Calculated (+0.25 H$_2$O): C, 64.79; H, 7.59; N, 6.67 Found: C, 64.85; H, 7.40; N, 6.54

EXAMPLE 60

Preparation of Fmoc-Val-Aib-NH—CH(CHO)CH$_2$COOH

To 280 mg of Fmoc-Val-Aib-NH—CH[CH(OCH$_3$)$_2$]CH$_2$COOBu$^t$ as obtained in Example 59, 4 ml of trifluoroacetic acid and 200 μl of water were added; the mixture was kept standing at 28° C. for 4 hours. After being concentrated under reduced pressure, the mixture was solidified by the addition of ether-hexane to yield 214 mg of the title compound as a white powder.

Elemental analysis

Calculated (+0.5 H$_2$O): C, 63.15; H, 6.43; N, 7.59 Found: C, 63.34; H, 6.52; N, 7.61

EXAMPLE 61

Preparation of Fmoc-Aib-Aib-NH—CH[CH(OCH$_3$)$_2$]CH$_2$COOBu$^t$

To 220 mg of Fmoc-NH—CH[CH(OCH$_3$)$_2$]CH$_2$COOBu$^t$ as obtained in Reference Example 21, 10 ml of dimethylformamide containing 20% piperidine was added; the mixture was kept standing at 28° C. for 1 hour. The mixture was concentrated under reduced pressure; the resulting residue was purified through a silica gel column (1.7 cm dia.×8.5 cm) with ethyl acetate:hexane (1:5) as an eluent; the fraction containing the desired product was concentrated under reduced pressure to yield NH$_2$-CH[CH(OCH$_3$)$_2$]CH$_2$COOBu$^t$ as a colorless oily substance. This substance was dissolved in 5 ml of dimethylformamide; after 180 mg of Fmoc-Aib-Aib-OH was added, 68 mg of HOBt and 100 mg of WSCD·HCl were added at 0° C. while the solution was stirred. After the reaction mixture was stirred at 0° C. for 1 hour and 28° C. for 14 hours, it was concentrated under reduced pressure; ethyl acetate was added to the residue; the organic layer was washed with saturated aqueous sodium hydrogen carbonate and saturated saline. After being dried with anhydrous sodium sulfate, the organic layer was concentrated under reduced pressure; hexane was added to the residue to yield 207 mg of the title compound as a white powder.

Elemental analysis

Calculated (+0.5 H$_2$O): C, 63.85; H, 7.47; N, 6.77 Found: C, 63.61; H, 7.49; N, 7.01

EXAMPLE 62

Preparation of Fmoc-Aib-Aib-NH—CH(CHO)CH$_2$COOH

To 107 mg of Fmoc-Aib-Aib-NH—CH[CH(OCH$_3$)$_2$]CH$_2$COOBu$^t$ as obtained in Example 61, 2 ml of trifluoroacetic acid and 100 μl of water were added; the mixture was kept standing at 28° C. for 4 hours. After being concentrated under reduced pressure, the residue was triturated in ether-hexane to yield 79 mg of the title compound as a white powder.

Elemental analysis

Calculated (+H$_2$O): C, 61.47; H, 6.30; N, 7.97 Found: C, 61.59; H, 6.21; N, 8.27

EXAMPLE 63

Preparation of 2-Naphthoyl-Val-Ala-NHCH(COCH$_2$OCOC$_6$F$_5$)CH$_2$CH$_2$COOBu$^t$ 2-Naphthoyl-Val-Ala-OH (121 mg, 0.2 mmol) as obtained in Reference Example 14 was dissolved in DMF (10 ml) and KF (33 mg, 0.6 mmol) was added followed by stirring for 3 minutes at room temperature. Pentafluorobenzoic acid (49 mg, 0.23 mmol) was added and the mixture was stirred for 17 hours at room temperature. Pentafluorobenzoic acid (49 mg, 0.23 mmol) was added again and stirred for an additional 24 hours. Ethyl acetate was added and the solution was washed with water, 5% aqueous NaHCO$_3$ and water, then dried over anhydrious sodium silica gel (6 g) using ethyl acetatetoluene (5:2) as eluent. The fractions containing desired product was collected and the solvent was evaporated. The residue was triturated with petroleum ether to give a white powder. 32 mg (22%).

Elemental analysis Calculated: C, 58.77; H, 5.21; N, 5.71. Found: C, 59.33; H, 5.44; N, 5.94.

EXAMPLE 64

Preparation of 2-Naphthoyl-Val-Ala-NHCH(COCH$_2$OCOC$_6$F$_5$)CH$_2$CH$_2$COOH

2-Naphthoyl-Val-Ala-NHCH(COCH$_2$OCOC$_6$F$_5$)CH$_2$CH$_2$COOBu$^t$ (20 mg, 0.027 mmol) as obtained in Example 63 was treated with TFA (0.2 ml) for 30 minutes at room temperature. A mixture of ether-petroleum ether was added to give a powder. 16 mg (87%)

Elemental analysis

Calculated: C, 56.56; H, 4.45; N, 6.18. Found: C, 56.62; H, 4.65; N, 6.30.

EXAMPLE 65

Preparation of 2-Naphthoyl-Val-Ala-NHCH[COCH$_2$OCO (2,6-Cl$_2$-C$_6$H$_3$)]CH$_2$CH$_2$COOBu$^t$ 2-Naphthoyl-Val-Ala-NHCH(COCH$_2$OCOC$_6$F$_5$)CH$_2$CH$_2$COOBu$^t$ (121 mg, 0.2 mmol) as obtained in Reference Example 14 was dissolved in DMF (10 ml) together with KF (35 mg, 0.6 mmol), and the mixture was stirred for 3 minutes at room temperature, 2,6-Dichlorobenzoic acid (46 mg, 0.24 mmol) was added and the solution was stirred at room temperature for 3 hours. The solvent was evaporated and the residue taken up in ethyl acetate. The solution was washed successively with brine, saturated NaHCO$_3$, and brine, dried over sodium sulfate, and evaporated. The residue was triturated with ethyl acetate-ether-petroleum ether to give a white powder. 117 mg (82%).

Elemental analysis

Calculated: C, 60.51; H, 5.78; N, 5.88. Found: C, 60.80; H, 6.07; N, 6.33.

EXAMPLE 66

Preparation of 2-Naphthoyl-Val-Ala-NHCH[COCH$_2$OCO (2,6-Cl$_2$-C$_6$H$_3$) CH$_2$CH$_2$COOH This compound was obtained in the same manner as in Example 64 using 2-Naphthoyl-Val-Ala-NHCH[COCH$_2$OCO(2,6-Cl$_2$-C$_6$H$_3$)]CH$_2$CH$_2$COOBu$^t$ (60 mg, 0.084 mmol). 41 mg (74%).

Elemental analysis

Calculated (+0.5H$_2$O): C, 57.57; H, 5.13; N, 6.30. Found: C, 57.50; H, 5.49; N, 6.61.

EXAMPLE 67

Preparation of 2-Naphthoyl-Val-Ala-NHCH{COCH$_2$OCO [2,6-(CF$_3$)$_2$-C$_6$H$_3$]}CH$_2$CH$_2$COOBu$^t$ This compound was obtained in the same manner as in Example 65 using 2-Naphthoyl-Val-Ala-NHCH(COCH$_2$Br)CH$_2$CH$_2$-COOBu$^t$ (35 mg, 0.058 mmol), described in Reference Example 14), KF (10 mg, 0.0174 mmol) and 2,6-di(trifluoromethyl)benzoic acid (18 mg, 0.07 mmol). 40 mg (89%).

Elemental analysis

Calculated: C, 58.38; H, 5.29; N, 5.38. Found: C, 58.40; H, 5.29; N, 5.33.

EXAMPLE 68

Preparation of 2-Naphthoyl-Val-Ala-NHCH{COCH$_2$OCO [2,6-(CF$_3$)$_2$-C$_6$H$_3$]}CH$_2$CH$_2$COOH This compound was obtained in the same manner as in Example 64 using 2-Naphthoyl-Val-Ala-NHCH(COCH$_2$Br)CH$_2$CH$_2$-COOBu$^t$ (35 mg, 0.045 mmol, described in Example 65). 33 mg (100%).

Elemental analysis

Calculated: C, 56.28; H, 4.58; N, 5.79. Found: C, 55.98; H, 4.88; N, 6.02.

EXAMPLE 69

Preparation of 2-Naphthoyl-Val-Ala-NHCH[COCH$_2$OCO [2,6-Cl$_2$-C$_6$H$_3$]CH$_2$CH$_2$COOEt This compound was obtained in the same manner as in Example 65 using 2-Naphthoyl-Val-Ala-NHCH(COCH$_2$Br)CH$_2$CH$_2$-COOEt (1.15 g, 2 mmol, described in Reference Example 15), KF (350 mg) and 2,6-dichlorobenzoic acid (458 mg, 2.4 mmol). 1.27 g (92.5%).

Elemental analysis

Calculated: C, 59.48; H, 5.43; N, 6.12. Found: C, 59.83; H, 5.62; N, 6.25.

EXAMPLE 70

Preparation of 2-Naphthoyl-Val-Ala-NHCH(CH$_2$CH$_2$CO$_2$Bu$^t$)CHOHCH$_2$SO$_2$CH$_2$CH$_2$CH$_3$ Z—NHCH(CH2CH$_2$CO$_2$Bu$^t$)CHOHCH$_2$SO$_2$CH$_2$CH$_2$CH$_3$ (184 mg, 0.415 mmol) as obtained in Reference Example 19 was hydrogenated over Pd black in THF (2 ml) for 3 h, filtered and concentrated in vacuo. The residue (128 mg, 0.415 mmol), 2-Naphthoyl-Val-Ala-OH (129 mg, 0.376 mmol) and HONB (67.4 mg, 0.376 mmol) were dissolved in DMF (2 ml), and WSCD·HCl (72.1 mg, 0.376 mmol) was added to the solution at 0° C. The reaction mixture was stirred for 20 h at room temperature and concentrated in vacuo. The residue was dissolved in AcOEt and the solution was washed successively with 10% aqueous citric acid, aqueous NaHCO$_3$ and brine, dried over anhydrous Na$_2$SO$_4$, and concentrated in vacuo. The residue was crystallized from ether and hexane to give the title compound (218 mg, 91.7%).

Elemental analysis

Calculated for C$_{32}$H$_{47}$O$_8$N$_3$S: C, 60.64; H, 7.47; N, 6.63. Found: C, 60.85; H, 7.37; N, 6.68.

EXAMPLE 71

Preparation of 2-Naphthoyl-Val-Ala-NHCH(CH$_2$CH$_2$CO$_2$Bu$^t$)CH═CHSO$_2$CH$_2$CH$_2$CH$_3$ Methanesulfonyl chloride (27.5 μl, 0.355 mmol) and TEA (115 μl, 0.828 mmol) were added to a stirred solution of 2-Naphthoyl-Val-Ala-NHCH(CH$_2$CH$_2$CO$_2$Bu$^t$)CHOHCH$_2$SO$_2$CH$_2$CH$_2$CH$_3$ (150 mg, 0.237 mmol) as obtained in Example 70 in THF (2 ml) at 0° C. The reaction mixture was stirred for 1 h and AcOEt was added. The solution was washed with aqueous NaHCO$_3$ and brine, dried over anhydrous Na$_2$SO$_4$, and concentrated invacuo. The residue was crystallized from hexane to give the title compound (133 mg, 91.2%).

Elemental analysis

Calculated for C$_{32}$H$_{457}$N$_3$S·1.5H$_2$O: C, 59.79; H, 7.53; N, 6.54. Found: C, 59.54; H, 7.27; N, 6.56.

EXAMPLE 72

Preparation of 2-Naphthoyl-Val-Ala-NHCH(CH$_2$CH$_2$CO$_2$H)CH═CHSO$_2$CH$_2$CH$_2$CH$_3$ TFA (2 ml) was added to 2-Naphthoyl-Val-Ala-NHCH(CH$_2$CH$_2$CO$_2$Bu$^t$)CH═CHSO$_2$CH$_2$CH$_2$CH$_3$ (100 mg, 0.162 mmol) as obtained in Example 71 and the reaction mixture was stirred for 1 h at room temperature and concentrated in vacuo. The residue was crystallized from ether to give the title compound (76.8 mg, 84.5%). [α]$^{23}_D$+43.4° (c 0.96, DMF).

Elemental analysis

Calculated for C$_{28}$H$_{37}$O$_7$N$_3$S·0.2TFA·1.5H$_2$O: C, 55.97; H, 6.65; N, 6.89. Found: C, 55.79; H, 6.64; N, 6.79.

EXAMPLE 73

Preparation of 2-Fluorenecarbonyl-Val-Ala-NH—CH[CH(OCH$_3$)$_2$]CH$_2$CH$_2$CO$_2$Bu$^t$ WSCD·HCl (74.8 mg, 0.390 mmol) was added to a stirred solution of 2-fluorenecarboxylic acid (82.1 mg, 0.390 mmol), H-Val-Ala-NH—CH[CH(OCH$_3$)$_2$]CH$_2$CH$_2$CO$_2$Bu$^t$ (150 mg, 0.372 mmol) as obtained in Reference Example 16 and HOBt (52.7 mg, 0.390 mmol) in DMF (2 ml) at 0° C. The reaction mixture was stirred for 17 h at 28° C. and concentrated in vacuo. The residue was washed H$_2$O and dried. The crude product was crystallized from CH$_3$CN and ether to give the title compound (151 mg, 68.5%).

Elemental analysis

Calculated for C$_{33}$H$_{45}$O$_7$N$_3$: C, 66.53; H, 7.61; N, 7.05. Found: C, 66.11; H, 7.65; N, 7.18.

EXAMPLE 74
Preparation of 2-Fluorenecarbonyl-Val-Ala-NH—CH(CHO)CH$_2$CH$_2$CO$_2$H TFA (2.5 ml) and H$_2$O (250 μl) were added to 2-Fluorenecarbonyl-Val-Ala-NHCH[CH(OCH$_3$)$_2$]CH$_2$CH$_2$CO$_2$Bu$^t$ as obtained in Example 73 and the reaction mixture was stirred for 3 h and concentrated in vacuo. The residue was crystallized from ether to give the title compound (88.7 mg, 89.2%). [α]$^{23}_D$+50.8° (c 0.99, DMF)

Elemental analysis
Calculated for C$_{27}$H$_{31}$O$_6$N$_3$·1.2H$_2$O: C, 62.95; H, 6.53; N, 8.16. Found: C, 62.73; H, 6.47; N, 8.32.

EXAMPLE 75
Preparation of 9-Fluorenecarbonyl-Val-Ala-NH—CH[CH(OCH$_3$)$_2$]CH$_2$CH$_2$CO$_2$Bu$^t$ In the same manner as in Examaple 73, 42.3 mg of the title compound was obtained using 82.1 mg of 9-fluorenecarboxylic acid and 150 mg of H-Val-Ala-NH—CH[CH(OCH$_3$)$_2$]CH$_2$CH$_2$CO$_2$Bu$^t$ as obtained in Reference Example 16.

Elemental analysis
Calculated for C$_{33}$H$_{45}$O$_7$N$_3$: C, 66.53; H, 7.61; N, 7.05. Found: C, 66.16; H, 7.56; N, 7.20.

EXAMPLE 76
Preparation of 9-Fluorenecarbonyl-Val-Ala-NH—CH(CHO)CH$_2$CH$_2$CO$_2$H In ther same manner as in Example 74, 21.4 mg of the title compound was obtained using 0.6 ml of TFA and 30 mg of 9-Fluorenecarbonyl-Val-Ala-NH—CH[CH(OCH$_3$)$_2$]CH$_2$CH$_2$CO$_2$Bu$^t$ as obtained in Example 75. [α]$^{23}_D$-44.0° (c 0.40, DMF).

Elemental analysis
Calculated for C27H$_{31}$O$_6$N$_3$·0.2TFA·2H$_2$O: C, 59.58; H, 6.42; N, 7.61. Found: C, 59.45; A, 6.15; N, 7.73.

EXAMPLE 77
Preparation of 9-Fluorenone-2-carbonyl-Val-Ala-NH—CH[CH(OCH$_3$)$_2$]CH$_2$CH$_2$CO$_2$Bu$^t$ In the same manner as in Example 73, 273 mg of the title compound was obtained using 175 mg of 9-fluorenone-2-carboxylic acid and 300 mg of H-Vla-Ala-NH—CH[CH(OCH$_3$)$_2$]CH$_2$CH$_2$CO$_2$Bu$^t$ as obtained in Reference Example 16.

Elemental analysis
Calculated for C$_{33}$H$_{43}$O$_8$N$_3$·0.8H$_2$O: C, 63.51; H, 7.20; N, 6.73. Found: C, 63.57; H, 6.98; N, 6.85.

EXAMPLE 78
Preparation of 9-Fluorenone-2-carbonyl-Val-Ala-NH—CH(CHO)CH$_2$CH$_2$CO$_2$H In the same manner as in example 74, 81.7 mg of the title compound was obtained using 2 ml of TFA and 100 mg of 9-Fluorenone-2-carbonyl-Val-Ala-NH—CH[CH(OCH$_3$)$_2$]CH$_2$CH$_2$CO$_2$Bu$^t$ as obtained in Example 77. [α]$^{23}_D$+46.1° (c 0.99, DMF).

Elemental analysis
Calculated for C$_{27}$H$_{29}$O$_7$N$_3$·2H$_2$O: C, 59.66; H, 6.12; N, 7.73. Found: C, 59.65; H, 5.95; N, 7.57.

EXAMPLE 79
Preparation of 9-(Hydroxy)-2-fluorenecarbonyl-Val-Ala-NH—CH[CH(OCH$_3$)$_2$]CH$_2$CH$_2$CO$_2$Bu$^t$ To a stirred solution of 9-Fluorenone-2-carbonyl-Val-Ala-NH—CH[CH(OCH$_3$)$_2$]CH$_2$CH$_2$CO$_2$Bu$^t$ (120 mg, 0.197 mmol) as obtained in Example 77 in DMF (1.2 ml) and H$_2$O (0.1 ml), NaBE$_4$ was added and the reaction mixture was stirred for 2.5 h at 0° C. H$_2$O was added to the solution and the precipitate was washed with H$_2$O and dried to give the title compound (102 mg, 85.3%).

Elemental analysis
Calculated for C$_{33}$H$_{45}$O$_8$N$_3$·H$_2$O: C, 62.94; H, 7.52; N, 6.67. Found: C, 62.89; H, 7.32; N, 6.72.

EXAMPLE 80
Preparation of 9-(Hydroxy)-2-fluorenecarbonyl-Val-Ala-NH—CH(CHO)CH$_2$CH$_2$CO$_2$H In the same manner as in Example 74, 45.7 mg of the title compound was obtained using 1 ml of TFA and 70 mg of 9-Fluorenone-2-carbonyl-Val-Ala-NH—CH[CH(OCH$_3$)$_2$]CH$_2$CH$_2$CO$_2$Bu$^t$ as obtained in Example 79. [α]$^{23}_D$+23.6° (c 1.00, DMF).

Elemental analysis
Calculated for C$_{27}$H$_{31}$O$_7$N$_3$·TFA: C, 55.68; H, 5.48; N, 6.72. Found: C, 55.92; H, 5.70; N, 7.04.

EXAMPLE 81
Preparation of 2-Phenylbenzoyl-Val-Ala-NH—CH[CH(OCH$_3$)$_2$]CH$_2$CH$_2$CO$_2$Bu$^t$ In the same manner as in Example 73, 70.4 mg of the title compound was obtained using 99.2 mg of 2-phenylbenzoic acid and 188 mg of H-Val-Ala-NH—CH[CH(OCH$_3$)$_2$]CH$_2$CH$_2$CO$_2$Bu$^t$ as obtained in Reference Example 16.

Elemental analysis
Calculated for C$_{32}$H$_{45}$O$_7$N$_3$: C, 65.84; H, 7.77; N, 7.20. Found: C, 65.43; H, 7.68; N, 7.39.

EXAMPLE 82
Preparation of 2-Phenylbenzoyl-Val-Ala-NH—CH(CHO)CH$_2$CH$_2$CO$_2$H In the same manner as in Example 74, 35.6 mg of the title compound was obtained using 1 ml of TFA and 50 mg of 2-Phenylbenzoyl-Val-Ala-NH—CH[CH(OCH$_3$)$_2$]CH$_2$CH$_2$CO$_2$Bu$^t$ as obtained in Example 81. [α]$^{23}_D$-24.1° (C 0.80, DMF).

Elemental analysis
Calculated for C$_{26}$H$_{31}$O$_6$N$_3$·H$_2$O: C, 62.51; H, 6.66; N, 8.41.
Found: C, 62.56; H, 6.78; N, 8.57.

EXAMPLE 83
Preparation of 1-Fluorenecarbonyl-Val-Ala-NH—CH[CH(OCH$_3$)$_2$]CH$_2$CH$_2$CO$_2$Bu$^t$ In the same manner as in Example 73, 1.40 g of the title compound was obtained using 900 mg of 1-Fluorenecarbonyl-Val-Ala-OE and 662 mg of H$_2$N-CH[CH(OCH$_3$)$_2$]CH$_2$CH$_2$CO$_2$Bu$^t$ as obtained in Reference Example 9.

Elemental analysis
Calculated for C33H$_{45}$O$_7$N$_3$·0.1H$_2$O: C, 66.33; H, 7.62; N, 7.03. Found: C, 66.10; H, 7.65; N, 6.95.

EXAMPLE 84
Preparation of 1-Fluorenecarbonyl-Val-Ala-NH—CH(CHO)CH$_2$CH$_2$CO$_2$H In the same manner as in Example 74, 158 mg of the title compound was obtained using 4 ml of TFA and 200 mg of 1-Fluorenecarbonyl-Val-Ala-NH—CH[CH(OCH$_3$)$_2$]CH$_2$CH$_2$CO$_2$Bu$^t$ as obtained in Example 83. [α]$^{23}_D$-15.7° (c 1.01, DMF).

Elemental analysis
Calculated for C$_{27}$H$_{31}$O$_6$N$_3$·1.5H$_2$O: C, 62.30; H, 6.58; N, 8.07. Found: C, 62.25; H, 6.38; N, 8.08.

EXAMPLE 85
Preparation of Iminodibenzyl-5-carbonyl-Val-Ala-NH—CH[CH(OCH$_3$)$_2$]CH$_2$CH$_2$CO$_2$Bu$^t$ In the same manner as in Example 73, 1.40 g of the title compound was obtained using 230 mg of Iminodibenzyl-5-carbonyl-Val-Ala-OH and 157 mg of H$_2$N-CH[CH(OCH$_3$)$_2$]CH$_2$CH$_2$CO$_2$Bu$^t$ as obtained in Reference Example 9.

Elemental analysis
Calculated for C$_{34}$H$_{48}$O$_7$N$_4$·0.5H$_2$O: C, 64.43; H, 7.79; N, 8.84. Found: C, 64.42; H, 7.75; N, 8.86.

EXAMPLE 86
Preparation of Iminodibenzyl-5-carbonyl-Val-Ala-NH—CH(CHO)CH$_2$CH$_2$CO$_2$H In the same manner as in Example 74, 91 mg of the title compound was obtained using 2.5 ml of TFA and 130 mg of Iminodibenzyl-5-carbonyl-Val-Ala-NH—CH[CH(OCH$_3$)$_2$]CH$_2$CH$_2$CO$_2$Bu$^t$ as obtained in Example 85. [α]$^{21}_D$ −8.0° (c 0.99, DMF).

Elemental analysis
Calculated for C$_{28}$H$_{34}$O$_6$N$_4$·0.5TFA·0.3H$_2$O: C, 59.54; H, 6.05; N, 9.58. Found: C, 59.58; H, 6.09; N, 9.80.

EXAMPLE 87
Preparation of 6-(Benzyloxycarbonyl)-2-naphthoyl-Val-Ala-NH—CH[CH(OCH$_3$)$_2$]CH$_2$CH$_2$CO$_2$Bu$^t$ In the same manner as in Example 73, 339 mg of the title compound was obtained using 300 mg of 6-(Benzyloxycarbonyl)-2-naphthoyl-Val-Ala-OH and 176 mg of H$_2$N-NH—CH[CH(OCH$_3$)$_2$]CH$_2$CH$_2$CO$_2$Bu$^t$ as obtained in Reference Example 9.

Elemental analysis
Calculated for C$_{38}$H$_{49}$O$_9$N$_3$·0.2H$_2$O: C, 65.63; H, 7.16; N, 6.04. Found: C, 65.49; H, 6.92; N, 6.14.

EXAMPLE 88
Preparation of 6-(Benzyloxycarbonyl)-2-naphthoyl-Val-Ala-NH—CH(CHO)CH$_2$CH$_2$CO$_2$H In the same manner as in Example 74, 79.2 mg of the title compound was obtained using 2 ml of TFA and 100 mg of 6-(Benzyloxycarbonyl)-2-naphthoyl-Val-Ala-NH—CH[CH(OCH$_3$)$_2$]CH$_2$CH$_2$CO$_2$Bu$^t$ as obtained in Example 87. [α]$^{21}_D$ +40.3° (c 0.99, DMF).

Elemental analysis
Calculated for C$_{32}$H$_{35}$O$_8$N$_3$·0.8H$_2$O: C, 63.63; H, 6.11; N, 6.96. Found: C, 63.60; H, 6.15; N, 7.20.

EXAMPLE 89
Preparation of 6-(Carboxy)-2-naphthoyl-Val-Ala-NH—CH[CH(OCH$_3$)$_2$]CH$_2$CH$_2$CO$_2$Bu$^t$ 6-(Benzyloxycarbonyl)-2-naphthoyl-Val-Ala-NH—CH[CH(OCH$_3$)$_2$]CH$_2$CH$_2$CO$_2$Bu$^t$ (220 mg, 0.318 mmol) as obtained in Example 87 was hydrogenated over Pd black for 25 h in THF (3 ml), filtered and concentrated in vacuo. The residue was crystallized from ether oto give the title compound (149 mg, 78.0%).

Elemental analysis
Calculated for C$_{31}$H$_{43}$O$_9$N$_3$·0.4H$_2$O: C, 61.25; H, 7.25; N, 6.90. Found: C, 61.22; H, 7.10; N, 7.01.

EXAMPLE 90
Preparation of 6-(Carboxy)-2-naphthoyl-Val-Ala-NH—CH(CHO)CH$_2$CH$_2$CO$_2$H In the same manner as in Example 74, 86.1 mg of the title compound was obtained using 2 ml of TFA and 100 mg of 6-carboxy-2-naphthoyl-Val-Ala-NH-CR[CH(OCH$_3$)$_2$]CH$_2$CH$_2$CO$_2$Bu$^t$ as obtained in Example 89. [α]$^{21}_D$ +28.0° (c 0.95, DMF).

Elemental analysis
Calculated for C$_{25}$H$_{29}$O$_8$N$_3$·H$_2$O; C, 58.02; H, 6.04; N, 8.12. Found: C, 58.24; H, 6.45; N, 8.11.

EXAMPLE 91
Preparation of 2-Naphthoyl-Val-Ala-NH—CH[CH(OCH$_3$)$_2$]CH$_2$CH$_2$CO$_2$Et In the same manner as in Example 73, 1.67 g of the title compound was obtained using 1.50 g of 2-Naphthoyl-Val-Ala-OH and 989 mg of H$_2$N-CH[CH(OCH$_3$)$_2$]CH$_2$CH$_2$CO$_2$Et obtained in the same manner as in Reference Example 9.

Elemental analysis
Calculated: C, 63.50; H, 7.40; N, 7.93. Found: C, 63.24; H, 7.32; N, 8.00.

EXAMPLE 92
Preparation of 2-Naphthoyl-Val-Ala-NH—CH(CHO)CH$_2$CH$_2$CO$_2$Et In the same manner as in Example 74, 864 mg of the title compound was obtained using 36 ml of TFA and 1.6 g of 2-Naphthoyl-Val-Ala-NH—CH[CH(OCH$_3$)$_2$]CH$_2$CH$_2$CO$_2$Et as obtained in Exampale 91. [α]$^{21}_D$ +34.3° (c 1.03, DMF).

Elemental analysis
Calculated for C$_{26}$H$_{33}$O$_6$N$_3$·0.5H$_2$O: C, 63.40; H, 6.96; N, 8.53. Found: C, 63.65; H, 7.01; N, 8.60.

EXAMPLE 93
Preparation of 2-Naphthoyl-Abu-Ala-NH—CH[CH(OCH$_3$)$_2$] CH$_2$CH$_2$CO$_2$Bu$^t$ WSCD·HCl (101 mg, 0.529 mmol) was added to a stirred solution of 2-Naphthoyl-Abu-Ala-OH (183 mg, 0.529 mmol), H$_2$N-CH[CH(OCH$_3$)$_2$]CH$_2$CH$_2$CO$_2$Bu$^t$ (148 mg, 0.634 mmol) as obtained in Reference Example 9 and HOBt (71.4 mg, 0.529 mmol) in DMF (3 ml) at 0° C. The reaction mixture was stirred for 16 h at room temperature and concentrated in vacuo. The residue was successively washed with aqueous NaHCO$_3$ and H$_2$O and dried. The crude product was recrystallized from CH$_3$CN to give the title compound (183 mg, 67.7%) as a crystals.

Elemental analysis
Calculated for C$_{29}$H$_{41}$O$_7$N$_3$: C, 64.07; H, 7.60; N, 7.73. Found: C, 64.00; H, 7.46; N, 7.64.

EXAMPLE 94
Preparation of 2-Naphthoyl-Abu-Ala-NH—CH(CHO)CH$_2$CH$_2$CO$_2$H

TFA (2.5 ml) and H$_2$O (250 μl) was added to 2-Naphthoyl-Abu-Ala-NH—CH[CH(OCH$_3$)$_2$]CH$_2$CH$_2$CO$_2$Bu$^t$ (120 mg, 0.203 mmol) as obtained in Example 93 and the reaction mixture was stirred for 4 h at room temperature and concentrated in vacuo. The residue was crystallized from ether to give 2-Naphthoyl-Abu-Ala-NH—CH(CHO)CH$_2$CH$_2$CO$_2$H (89.3 mg, 90.9%) [α]$^{23}_D$ + 36.3° (c 0.98, DMF).

Elemental analysis
Calculated for C$_{23}$H$_{27}$O$_6$N$_3$·0.2TFA·H$_2$O: C, 58.28; H, 6.10; N, 8.71. Found: C, 58.31; H, 6.07; N, 8.91.

EXAMPLE 95
Preparation of 2-Naphthoyl-Gln-Ala-NH—CH[CH(OCH$_3$)$_2$] CH$_2$CH$_2$CO$_2$Bu$^t$ In the same manner as in Example 93, 84.5 mg of the title compound was obtained using 70 mg of 2-Naphthoyl-Gln-Ala-OH and 150 mg of H$_2$N-CH[CH(OCH$_3$)$_2$] CH$_2$CH$_2$CO$_2$Bu$^t$ as obtained in Reference Example 9.

Elemental analysis
Calculated for $C_{30}H_{42}O_8N_4 \cdot 0.5H_2O$: C, 60.50; H, 7.28; N, 9.41. Found: C, 60.54; H, 7.14; N, 9.42.

EXAMPLE 96

Preparation of 2-Naphthoyl-Gln-Ala-NH—CH(CHO)$CH_2CH_2CO_2H$

In the same manner as in Example 94, 41.1 mg of the title compound was obtained using 1 ml of TFA and 50 mg of 2-Naphthoyl-Gln-Ala-NH—CH[CH(OCH$_3$)$_2$]CH$_2$CH$_2$CO$_2$Bu$^t$ as obtained in Example 95. $[\alpha]^{23}_D$ −44.0° (c 0.40, DMF).

Elemental analysis
Calculated for $C_{24}H_{28}O_7N_4 \cdot 0.3TFA \cdot 0.8ether \cdot H_2O$: C, 56.02; H, 6.48; N, 9.40. Found: C, 55.91; H, 6.66; N, 9.34.

EXAMPLE 97

Preparation of 2-Naphthoyl-Glu(OBu$^t$)-Ala-NH—CH[CH(OCH$_3$)$_2$]CH$_2$CH$_2$CO$_2$Bu$^t$ 2-Naphthoyl chloride (257 mg, 1.35 mmol) and TEA (187 μl, 1.35 mmol) were added at 0° C. to a stirred DMF solution (6 ml) containing H-Glu(OBu$^t$)-Ala-NH—CH[CH(OCH$_3$)$_2$]CH$_2$CH$_2$CO$_2$Bu$^t$ (549 mg, 1.12 mmol) obtained in the same manner as that described in Reference Example 16. The reaction mixture was stirred for 1.5 h at room temperature and AcOEt was added. The solution was washed successively with aqueous NaHCO$_3$ and brine, dried over anhydrous Na$_2$SO$_4$, and concentrated in vacuo. The residue was crystallized from ether and hexane to give the title compound (487 mg, 67.5%).

Elemental analysis
Calculated for $C_{34}H_{49}O_9N_3 \cdot 0.5H_2O$: C, 62.56; H, 7.72; N, 6.64. Found: C, 62.68; H., 7.78; N, 7.30.

EXAMPLE 98

Preparation 2-Naphthoyl-Glu-Ala-NH—CH(CHO)$CH_2CH_2CO_2H$

In the same manner as in Example 94, 202 mg of the title compound was obtained using 5 ml of TFA and 250 mg of 2-Naphthoyl-Glu(OBu$^t$)-Ala-NH—CH[CH(OCH$_3$)$_2$]CH$_2$CH$_2$CO$_2$Bu$^t$ as obtained in Example 97. $[\alpha]^{23}_D$ +13.5° (c 1.01, DMF).

Elemental analysis
Calculated for $C_{24}H_{27}O_8N_3 \cdot 0.2TFA \cdot 1.5H_2O$: C, 54.75; H, 5.69; N, 7.85. Found: C, 54.67; H, 5.92; N, 7.55.

EXAMPLE 99

Preparation of 2-Naphthoyl-Ile-Ala-NH—CH[CH(OCH$_3$)$_2$]CH$_2$CH$_2$CO$_2$Bu$^t$ In the same manner as in Example 93, 211 mg of the title compound was obtained using 198 mg of 2-Naphthoyl-Ile-Ala-OH and 148 mg of H$_2$N-CH[CH(OCH$_3$)$_2$]CH$_2$CH$_2$CO$_2$Bu$^t$ as obtained in Reference Example 9.

Elemental analysis
Calculated for $C_{31}H_{45}O_7N_3 \cdot 0.2H_2O$: C, 64.72; H, 7.95; N, 7.30. Found; C, 64.62; H, 7.72; N, 7.23.

EXAMPLE 100

Preparation of 2-Naphthoyl-Ile-Ala-NH—CH(CHO)$CH_2CH_2CO_2H$

In the same manner as in Example 94, 89.0 mg of the title compound was obtained using 2.5 ml of TFA and 120 mg of 2-Naphthoyl-Ile-Ala-NH—CH[CH(OCH$_3$)$_2$]CH$_2$CH$_2$CO$_2$Bu$^t$ as obtained in Example 99. $[\alpha]^{23}_D$ +36.5° (c 0.98, DMF).

Elemental analysis
Calculated for $C_{25}H_{31}O_6N_3 \cdot 0.2TFA \cdot 0.5H_2O$: C, 60.85; H, 6.47; N, 8.38. Found: C, 60.76; H, 6.55; N, 8.57.

EXAMPLE 101

Preparation of 2-Naphthoyl-Leu-Ala-NH—CH[CH(OCH$_3$)$_2$]CH$_2$CH$_2$CO$_2$Bu$^t$ In the same manner as in Example 93, 234 mg of the title compound was obtained using 198 mg of 2-Naphthoyl-Leu-Ala-OH and 148 mg of R$_2$N-CH[CH(OCH$_3$)$_2$]CH$_2$CH$_2$CO$_2$Bu$^t$ as obtained in Reference Example 9.

Elemental analysis
Calculated for $C_{31}H_{45}O_7N_3$: C, 65.13; H, 7.93; N, 7.35. Found: C, 65.02; H, 7.86; N, 7.24.

EXAMPLE 102

Preparation of 2-Naphthoyl-Leu-Ala-NH—CH(CHO)$CH_2CH_2CO_2H$

In the same manner as in Example 94, 90.4 mg of the title compound was obtained using 2.5 ml of TFA and 120 mg of Naphthoyl-Leu-Ala-NH—CH[CH(OCH$_3$)$_2$]CH$_2$CH$_2$CO$_2$Bu$^t$ as obtained in Example 101. $[\alpha]^{23}_D$ +33.0° (c 1.00, DMF).

Elemental analysis
Calculated for $C_{25}H_{31}O_6N_3 \cdot 0.2TFA \cdot 0.7H_2O$: C, 60.42; H, 6.51; N, 8.32. Found: C, 60.29; H, 6.55; N, 8.49.

EXAMPLE 103

Preparation of 2-Naphthoyl-Lys(Boc)-Ala-NH—CH[CH(OCH$_3$)$_2$]CH$_2$CH$_2$CO$_2$Bu$^t$ In the same manner as in Example 97, 379 mg of the title compound was obtained using 172 mg of 2-Naphthoyl chloride and 399 mg of H-Lys(Boc)-Ala-NH—CH[CH(OCH$_3$)$_2$]CH$_2$CH$_2$CO$_2$Bu$^t$ obtained in the same manner as that described in Reference Example 16.

Elemental analysis
Calculated for $C_{36}H_{54}O_9N_4 \cdot 0.2H_2O$: C, 62.63; H, 7.94; N, 8.11. Found: C, 62.49; H, 7.87; N, 8.03.

EXAMPLE 104

Preparation of 2-Naphthoyl-Lys-Ala-NH—CH(CHO)$CH_2CH_2CO_2H$

In the same manner as in Example 94, 192 mg of the title compound was obtained using 4 ml of TFA and 200 mg of 2-Naphthoyl-Lys(Boc)-Ala-NH—CH[CH(OCH$_3$)$_2$]CH$_2$CH$_2$CO$_2$Bu$^t$ as obtained in Example 103. $[\alpha]^{23}_D$ +17.8° (c 0.98, DMF).

Elemental analysis
Calculated for $C_{27}H_{33}O_8N_4 \cdot 0.2TFA \cdot 2H_2O$: C, 50.56; H, 5.70; N, 8.52. Found: C, 50.28; H, 5.87; N, 8.17.

EXAMPLE 105

Preparation of 2-Naphthoyl-Nle-Ala-NH—CH[CH(OCH$_3$)$_2$]CH$_2$CH$_2$CO$_2$Bu$^t$ In the same manner as in Example 93, 235 mg of the title compound was obtained using 198 mg of 2-Naphthoyl-Nle-Ala-OH and 148 mg of H$_2$N-CH[CH(OCH$_3$)$_2$]CH$_2$CH$_2$CO$_2$Bu$^t$ as obtained in Reference Example 9.

Elemental analysis
Calculated for $C_{31}H_{45}O_7N_3$: C, 65.13; a, 7.93; N, 7.35. Found: C, 64.90; H, 7.85; N, 7.20.

EXAMPLE 106

Preparation of 2-Naphthoyl-Nle-Ala-NH—CH(CHO)$CH_2CH_2CO_2H$

In the same manner as in Example 94, 86.5 mg of the title compound was obtained using 2.5 ml of TFA and 120 mg of 2-Naphthoyl-Nle-Ala-NH—CH[CH(OCH$_3$)$_2$]CH$_2$CH$_2$CO$_2$Bu$^t$ as obtained in Example 105. $[\alpha]^{23}_D$ +31.1° (c 0.98, DMF).

Elemental analysis
Calculated for $C_{25}H_{31}O_6N_3 \cdot 0.2TFA \cdot 1.2H_2O$: C, 58.89; H, 6.59; N, 8.18. Found: C, 58.63; H, 6.30; N, 8.41.

EXAMPLE 107
Preparation of 2-Naphthoyl-Nva-Ala-NH—CH[CH(OCH$_3$)$_2$]CH$_2$CH$_2$CO$_2$Bu$^t$ In the same manner as in Example 93, 207 mg of the title compound was obtained using 191 mg of 2-Naphthoyl-Nva-Ala-OH and 148 mg of H$_2$N-CH[CH(OCH$_3$)$_2$]CH$_2$CH$_2$CO$_2$Bu$^t$ as obtained in Reference Example 9.

Elemental analysis

Calculated for C$_{30}$H$_{43}$O$_7$N$_3$: C, 64.61; H, 7.77; N, 7.53. Found: C, 64.38; H, 7.65; N, 7.45.

EXAMPLE 108
Preparation of 2-Naphthoyl-Nva-Ala-NH—CH(CHO)CH$_2$CH$_2$CO$_2$H In the same manner as in Example 94, 90.0 mg of the title compound was obtained using 2.5 ml of TFA and 120 mg of 2-Naphthoyl-Nva-Ala-NH—CH[CH(OCH$_3$)$_2$]CH$_2$CH$_2$CO$_2$Bu$^t$ as obtained in Example 107. $[\alpha]^{23}_D$+33.8° (c 0.97, DMF).

Elemental analysis

Calculated for C$_{24}$H$_{29}$O$_6$N$_3$·0.2TFA·H$_2$O: C, 59.05; H, 6.34; N, 8.47. Found: C, 59.00; H, 6.29; N, 8.73.

EXAMPLE 109
Preparation of 2-Naphthoyl-Ser-Ala-NH—CH[CH(OCH$_3$)$_2$]CH$_2$CH$_2$CO$_2$Bu$^t$ In the same manner as in Example 93, 217 mg of the title compound was obtained using 150 mg of 2-Naphthoyl-Ser-Ala-OH and 127 mg of H$_2$N-CH[CH(OCH$_3$)$_2$]CH$_2$CH$_2$CO$_2$Bu$^t$ as obtained in Reference Example 9.

Elemental analysis

Calculated for C$_{28}$H$_{39}$O$_8$N$_3$·0.8H$_2$O: C, 60.65; H, 7.31; N, 7.50. Found: C, 60.06; H, 7.22; N, 7.35.

EXAMPLE 110
Preparation of 2-Naphthoyl-Ser-Ala-NH—CH(CHO)CH$_2$CH$_2$CO$_2$H In the same manner as in Example 94, 117 mg of the title compound was obtained using 3.5 ml of TFA and 150 mg of 2-Naphthoyl-Ser-Ala-NH—CH[CH(OCH$_3$)$_2$]CH$_2$CH$_2$CO$_2$Bu$^t$ as obtained in Example 109. $[\alpha]^{23}_D$−50.3° (c 1.01, DMF).

Elemental analysis

Calculated for C$_{22}$H$_{25}$O$_7$N$_3$·0.2TFA·1.5H$_2$O: C, 54.54; H, 5.76; N, 8.52. Found: C, 54.48; H, 5.82; N, 8.22.

EXAMPLE 111
Preparation of 2-Naphthoyl-Ser(Bzl)-Ala-NH—CH[CH(OCH$_3$)$_2$]CH$_2$CH$_2$CO$_2$Bu$^t$ In the same manner as in Example 93, 456 mg of the title compound was obtained using 371 mg of 2-Naphthoyl-Ser(Bzl)-Ala-OH and 226 mg of H$_2$N-CH[CH(OCH$_3$)$_2$]CH$_2$CH$_2$CO$_2$Bu$^t$ as obtained in Reference Example 9.

Elemental analysis

Calculated for C$_{35}$H$_{45}$O$_8$N$_3$: C, 66.12; H, 7.13; N, 6.61. Found: C, 65.96; H, 6.78; N, 6.49.

EXAMPLE 112
Preparation of 2-Naphthoyl-Ser(Bzl)-Ala-NH—CH(CHO)CH$_2$CH$_2$CO$_2$H In the same manner as in Example 94, 160 mg of the title compound was obtained using 4 ml of TFA and 200 mg of 2-Naphthoyl-Ser(Bzl)-Ala-NH—CH[CH(OCH$_3$)$_2$]CH$_2$CH$_2$CO$_2$Bu$^t$ as obtained in Example 111. $[\alpha]^{23}_D$+17.4° (c 1.04, DMF).

Elemental analysis

Calculated for C$_{29}$H$_{31}$O$_7$N$_3$·0.2TFA·H$_2$O: C, 61.48; H, 5.83; N, 7.32. Found: C, 61.42; H, 5.70; N, 7.31.

EXAMPLE 113
Preparation of 2-Naphthoyl-Thr-Ala-NH—CH[CH(OCH$_3$)$_2$]CH$_2$CH$_2$CO$_2$Bu$^t$ In the same manner as in Example 93, 226 mg of the title compound was obtained using 150 mg of 2-Naphthoyl-Thr-Ala-OH and 122 mg of H$_2$N-CH[CH(OCH$_3$)$_2$]CH$_2$CH$_2$CO$_2$Bu$^t$ as obtained in Reference Example 9.

Elemental analysis

Calculated for C$_{29}$H$_{41}$O$_8$N$_3$·0.2H$_2$O: C, 61.84; H, 7.41; N, 7.46. Found: C, 61.59; H, 7.15; N, 7.35.

EXAMPLE 114
Preparation of 2-Naphthoyl-Thr-Ala-NH—CH(CHO)CH$_2$CH$_2$CO$_2$H In the same manner as in Example 94, 135 mg of the title compound was obtained using 3.5 ml of TFA and 150 mg of 2-Naphthoyl-Thr-Ala-NH—CH[CH(OCH$_3$)$_2$]CH$_2$CH$_2$CO$_2$Bu$^t$ as obtained in Example 113. $[\alpha]^{23}_D$+24.6° (c 0.97, DMF).

Elemental analysis

Calculated for C$_{23}$H$_{27}$O$_7$N$_3$·0.2TFA·1.5H$_2$O: C, 54.65; H, 5.89; N, 8.10. Found: C, 54.77; H, 5.88; N, 7.75.

EXAMPLE 115
Preparation of 2-Naphthoyl-Thr(Bzl)-Ala-NH—CH[CH(OCH$_3$)$_2$]CH$_2$CH$_2$CO$_2$Bu$^t$ In the same manner as in Example 93, 505 mg of the title compound was obtained using 373 mg of 2-Naphthoyl-Thr(Bzl)-Ala-OH and 220 mg of H$_2$N-CH[CH(OCH$_3$)$_2$]CH$_2$CH$_2$CO$_2$Bu$^t$ as obtained in Reference Example 9.

Elemental analysis

Calculated for C$_{36}$H$_{47}$O$_8$N$_3$: C, 66.54; H, 7.29; N, 6.47. Found: C, 66.31; H, 7.14; N, 6.35.

EXAMPLE 116
Preparation of 2-Naphthoyl-Thr(Bzl)-Ala-NH—CH(CHO)CH$_2$CH$_2$CO$_2$H In the same manner as in Example 94, 158 mg of the title compound was obtained using 4 ml of TFA and 200 mg of 2-Naphthoyl-Thr(Bzl)-Ala-NH—CH[CH(OCH$_3$)$_2$]CH$_2$CH$_2$CO$_2$Bu$^t$ as obtained in Example 115. $[\alpha]^{23}_D$+46.3° (c 0.97, DMF).

Elemental analysis

Calculated for C$_{30}$H$_{33}$O$_7$N$_3$·0.2TFA·0.7H$_2$O: C, 62.63; H, 5.98; N, 7.21. Found: C, 62.53; H, 5.93; N, 7.13.

EXAMPLE 117
Preparation of 2-Naphthoyl-Pro-Ala-NH—CH(CHO)CH$_2$CH$_2$CO$_2$H 2-Naphthoyl-Pro-Ala-NH—CH[CH(OCH$_3$)$_2$]CH$_2$CH$_2$CO$_2$Bu$^t$ was obtained as an oil in the same manner as in Example 93 using 425 mg of 2-Naphthoyl-Pro-Ala-OH and 303 mg of H$_2$N-CH[CH(OCH$_3$)$_2$]CH$_2$CH$_2$CO$_2$Bu$^t$ (described in Reference Example 9). The protected peptide was dissolved in 12 ml of TFA in the same manner as in Example 94 to give 420 mg of the title compound. $[\alpha]^{21}_D$−15.3° (c 1.00, DMF).

Elemental analysis

Calculated for C$_{26}$H$_{31}$O$_6$N$_3$·0.2TFA·0.8H$_2$O: C, 61.83; H, 6.37; N, 8.10. Found: C, 60.91; H, 6.29; N, 8.42.

EXAMPLE 118
Preparation of 2-Naphthoyl-Val-Ala-NHCH(CH$_2$CH$_2$CO$_2$H)CH=CHSO$_2$Ph a) Preparation of 2-Naphthoyl-Val-Ala-NHCH(CH$_2$CH$_2$CO$_2$Bu$^t$)CHOHCH$_2$SO$_2$Ph Z—NHCH(CH$_2$CH$_2$CO$_2$Bu$^t$)CHOHCH$_2$SO$_2$Ph (1.20 g, 2.51 mmol) as obtained in Reference Examaple 17-b) was hydrogenated over Pd black in THF (12 ml) for 6 h, filtered and concentrated in vacuo. 2-Naphthoyl-Val-Ala-OH (782 mg, 2.28 mmol), HONB (409 mg, 228 mmol) and the mixture were diluted with DMF (10 ml), WSCD·HCl (438 mg, 2.28 mmol) was added to the solution at 0° C. The reaction residue was dissolved in AcOEt and the solution was washed successively with 10% aqueous citric acid, aqueous NaHCO$_3$ and brine, dried over anhydrous Na$_2$SO$_4$ and concentrated in vacuo. The residue was crystallized from hexane to give the title compound (1.32, 86.4%).

Elemental analysis

Calculated for $C_{35}H_{45}O_8N_3$: C, 62.95; H, 6.79; N, .6.29 Found: C, 63.21; H, 6.77; N, 6.41.

b) Preparation of 2-Naphthoyl-Val-Ala-NHCH(CH$_2$CH$_2$CO$_2$Bu$^t$) CH=CHSO$_2$Ph Methanesulfonyl chloride (52.2 μl, 0.674 mmol) and TEA (219 μl, 1.57 mmol) were added to a stirred solution of 2-Naphthoyl-Val-Ala-NHCH(CH$_2$CH$_2$CO$_2$Bu$^t$) CHOHCH$_2$SO$_2$Ph (300 mg, 0.449 mmol) as obtained in Example 118-a) in THF (4 ml) at 0° C. The reaction mixture was stirred for 1 h and AcOEt was added. The solution was washed with brine, dried over anhydrous Na$_2$SO$_4$ and concentrated in vacuo. The residue was crystallized from hexane to give the title compound (424 mg, 86.3%).

Elemental analysis

Calculated for $C_{35}H_{43}O_7N_3S·0.5H_2O$: C, 63.81; H, 6.73; N, 6.38. Found: C, 63.86; H, 6.50; N, 6.33.

c) Preparation of 2-Naphthoyl-Val-Ala-NHCH(CH$_2$CH$_2$CO$_2$H)CH=CHSO$_2$Ph

TFA (3 ml) was added to 2-Naphthoyl-Val-Ala-NHCH(CH$_2$CH$_2$CO$_2$Bu$^t$)CH=CHSO$_2$Ph (150 mg, 0.231 mmol) as obtained in Example 118-b) and the reaction mixture was stirred for 1.5 h at room temperature and concentrated in vacuo. The residue was crystallized from ether to give the title compound (131 mg, 95.4%). $[\alpha]^{23}_D$+42.8° (c 0.94, DMF).

Elemental analysis

Calculated for $C_{31}H_{35}O_7N_3S·H_2O$: C, 60.87; H, 6.10; N, 6.87. Found: C, 61.06; H, 6.23; N, 6.68.

EXAMPLE 119

Preparation of 2-Naphthoyl-Val-Ala-Glu-CH$_2$SO$_2$Ph a) 2-Naphthoyl-Val-Ala-Glu(OBu$^t$)-CH$_2$SO$_2$Ph 2-Naphthoyl-Val-Ala-NHCH(CH$_2$CH$_2$CO$_2$Bu$^t$) CHOHCH$_2$SO$_2$Ph (300 mg, 0.449 mmol) as obtained in Example 117-a) in CH$_2$Cl$_2$ (1.5 ml) was added to a stirred solution of pyridinium dichromate (1.72 mg, 4.49 mmol) in CH$_2$Cl$_2$ (1.5 ml) at room temperature. The reaction mixture was stirred for 5 days and concentrated in vacuo. The solution was washed with brine, dried over anhydrous Na$_2$SO$_4$, and concentrated in vacuo. The residue was chromatographed on silica gel using hexane-AcOEt, (1:2) as a solvent and the eluate was concentrated in vacuo. The residue was crystallized from ether and hexane to give the title compound (104 mg, 34.9%).

Elemental analysis

Calculated for $C_{35}H_{43}O_8N_3S$: C, 63.14; H, 6.51; N, 6.31. Found: C, 63.2; H, 6.49; N, 6.29.

b) Preparation of 2-Naphthoyl-Val-Ala-Glu-CH$_2$SO$_2$Ph

TFA (2 ml) was added to 2-Naphthoyl-Val-Ala-Glu (OBu$^t$)-CH$_2$SO$_2$Ph (80 mg, 0.120 mmol) as obtained in Example 119-a) and the reaction mixture was stirred for 2 h at room temperature and concentrated in vacuo. The residue was crystallized from ether to give the title compound (70.9 mg, 96.7%).

Elemental analysis

Calculated for $C_{31}H_{35}O_8N_3S·0.1TFA$: C, 60.34; H, 5.70; N, 6.77. Found: C, 60.64; H, 5.7; N, 6.88.

EXAMPLE 120

Preparation of 2-Naphthoyl-Val-Ala-NHCH(CH$_2$CO$_2$H) CH=CHCOCH$_3$

A solution of 2-Naphthoyl-Val-Ala-Glu(OBu$^t$)-H (25.0 mg, 48.9 μmol) and CH$_3$COCH=PPh$_3$ (18.7 mg, 58.6 μmol) in THF (1 ml) was stirred for 1.5 h at 50° C. and concentrated in vacuo. The residue was chromatographed on silica gel using CHCl$_3$-methanol, (30:1) as a solvent and the eluate was concentrated in vacuo. To the residue, TFA (1 ml) was added and the reaction mixture was stirred for 1 h at room temperature and concentrated in vacuo. The residue was crystallized from ether and hexane to give the title compound (12.7 mg, 52.3%). FAB MS (Pos) m/z 496 [M+H]+

EXAMPLE 121

Preparation of 2-Naphthoyl-Val-Ala-NHCH(CH$_2$CH$_2$CO$_2$H)CH=CHCOPh

In the same manner as in Example 120, 19.7 mg of the title compound was obtained namely using 32.2 mg of 2-Naphthoyl-Val-Ala-Glu(OBu$^t$)-H and 28.7 mg of PhCOCH=PPh$_3$ the protected compound was obtained, which was trented with 1 ml of TFA. FAB MS (Pos) m/z 558 [M+H]+.

EXAMPLE 122

Preparation of Fmoc-Val-Ach-NH—CH[CH(OCH$_3$)$_2$] CH$_2$CO$_2$Bu$^t$

In the same manner as in Example 51, 540 mg of the title compound was obtained using 320 mg of Fmoc-Val-Ach-OH and 330 mg of Z-HN—CH[CH(OCH$_3$)$_2$]CH$_2$CO$_2$Bu$^t$ as obtained in Reference Example 22.

Elemental analysis

Calculated: C, 66.75; E, 7.72; N, 6.31. Found: C, 66.53; H, 8.02; N, 6.01.

EXAMPLE 123

Preparation of Fmoc-Val-Ach-NH—CH(CHO) CH$_2$CH$_2$CO$_2$H

In the same manner as in Example 52, 239 mg of the title compound was obtained using 350 mg of Fmoc-Val-Ach-NH—CH[CH(OCH$_3$)$_2$]CH$_2$CO$_2$Bu$^t$ as obtained in Example 122.

Elemental analysis

Calculated (+0.5H$_2$O): C, 65.02; H, 6.69; N, 7.34. Found: C, 65.30; H, 6.77; N, 7.78.

EXAMPLE 124

Preparation of Fmoc-Val-Ach-NH—CH[CH(OCH$_3$)$_2$] CH$_2$CH$_2$CO$_2$Bu$^t$

In the same manner as in Example 51, 540 mg of the title compound was obtained using 343 mg of Fmoc-Val-Ach-OH and 330 mg of Z-HN—CH[CH(OCH$_3$)$_2$] CH$_2$CH$_2$CO$_2$Bu$^t$ as obtained in Reference Example 8.

Elemental analysis

Calculated (+0.25H$_2$O): C, 66.69; H, 7.88; N, 6.14. Found: C, 66.64; H, 8.09; N, 6.08.

EXAMPLE 125

Preparation of Fmoc-Val-Ach-NH—CH(CHO) CH$_2$CH$_2$CO$_2$H

In the same manner as in Example 52, 90 mg of the title compound was obtained using 100 mg of Fmoc-Val-Ach-NH—CH[CH(OCH$_3$)$_2$]CH$_2$CH$_2$CO$_2$Bu$^t$ as obtained in Exampale 124.

Elemental analysis

Calculated (+1.0H$_2$O): C, 64.52; H, 6.94; N, 7.05. Found: C, 64.71; H, 6.84; N, 6.64.

EXAMPLE 126
Preparation of Fmoc-Val-Acp-NH—CH[CH(OCH$_3$)$_2$]CH$_2$CO$_2$Bu$^t$ In the same manner as in Example 51, 305 mg of the title compound was obtained using 300 mg of Fmoc-Val-Acp-OH and 300 mg of Z-HN—CH[CH(OCH$_3$)$_2$]CH$_2$CO$_2$Bu$^t$ as obtained in Reference Example 22.

Elemental analysis

Calculated: C, 66.34; H, 7.58; N, 6.45. Found: C, 66.04; H, 7.67; N, 6.37.

EXAMPLE 127
Preparation of Fmoc-Val-Acp-NH—CH(CHO)CH$_2$CH$_2$CO$_2$H

In the same manner as in Example 52, 196 mg of the title compound was obtained using 240 mg of Fmoc-Val-Ach-NH—CH(CH(OCH$_3$)$_2$]CH$_2$CO$_2$Bu$^t$ as obtained in Example 126.

Elemental analysis

Calculated: C, 65.56; H, 6.42; N, 7.65. Found: C, 65.40; H, 6.53; N, 7.21.

EXAMPLE 128
Preparation of Fmoc-Val-Ach-NH—CH[CH(OCH$_3$)$_2$]CH$_2$CH$_2$CO$_2$Bu$^t$ In the same manner as in Example 51, 410 mg of the title compound was obtained using 300 mg of Fmoc-Val-Acp-OH and 300 mg of Z-HN—CH[CH(OCH$_3$)$_2$]CH$_2$CH$_2$CO$_2$Bu$^t$ as obtained in Reference Example 8.

Elemental analysis

Calculated: C, 66.30; H, 7.74; N, 6.21. Found: C, 66.09; H, 7.71; N, 6.10.

EXAMPLE 129
Preparation of Fmoc-Val-Acp-NH—CH(CHO)CH$_2$CH$_2$CO$_2$H

In the same manner as in Example 52, 240 mg of the title compound was obtained using 340 mg of Fmoc-Val-Acp-NH—CH[CH(OCH$_3$)$_2$]CH$_2$CH$_2$CO$_2$Bu$^t$ as obtained in Example 128.

Elemental analysis

Calculated: C, 65.02; H, 6.69; N, 7.34. Found: C, 65.01; H, 6.71; N, 6.64.

TEST EXAMPLE 1
Determination of ICE-inhibiting activity

To 40 µl of a recombinant ICH enzyme solution as purified in Reference Example 6, 10 µl of an enzyme reaction solution (200 mM HEPES, pH 7.5, 50 mM EDTA) was added. To this mixture, a 5 µl sample, previously diluted to $2\times10^{-3}$ M with dimethyl sulfoxide (DMSO), and distilled water were added to 72 µl; 28 µl of 50 µM Ac-Y-V-A-D-MCA (enzyme substrate solution) was added, followed by incubation at 37° C. for 20 minutes. This reaction was carried out on a 96-well fluoroplate (produced by Labo Systems).

After completion of the reaction, the fluorescence intensity of free aminomethylcoumarin was determined at a wavelength of 450 nm via excitation at a wavelength of 365 nm, using a fluorometer FCA (produced by Baxter). For control, 5 µl of sample-free 20% DMSO was added instead; the fluorometric value obtained from this control reaction was taken as 100% activity. When the residual activity was not higher than 10%, the sample solution was further diluted and then assayed for residual activity, in the same procedure as above, to obtain the IC$_{50}$ value.

The ICE-inhibiting activity of Fmoc-Val-Aib-NH—CH(CHO)CH$_2$COOH as prepared in Example 12 was determined to be $1.9\times10^{-8}$ in terms of IC$_{50}$ value.

| Sequence table | |
|---|---|
| Sequence ID Number: | 1 |
| Sequence length: | 20 |
| Sequence type: | Nucleic acid |
| Strandedness: | Single |
| Topology: | Linear |
| Sequence class: | Other nucleic acid (chemically synthesized DNA) |
| Antisense: | No |
| Sequence: | 5'-AAAAGGAGAGAAAAGCCATG-3' |
| | |
| Sequence ID Number: | 2 |
| Sequence length: | 28 |
| Sequence type: | Nucleic acid |
| Strandedness: | Single |
| Topology: | Linear |
| Sequence class: | Other nucleic acid (chemically synthesized DNA) |
| Antisense: | No |
| Sequence: | 5'-pGGAATTCCAAAGCCATGGCCGACAAGGT-3' |
| | |
| Sequence ID Number: | 3 |
| Sequence length: | 28 |
| Sequence type: | Nucleic acid |
| Strandedness: | Single |
| Topology: | Linear |
| Molecule class: | Other nucleic acid (chemically synthesized DNA) |
| Antisense: | Yes |
| Sequence: | 5'-pGGAATTCCTTCCTGCCCGCAGACATTCA-3' |
| | |
| Sequence ID Number: | 4 |

-continued

| Sequence table | |
|---|---|
| Sequence length: | 20 |
| Sequence type: | Nucleic acid |
| Strandedness: | Single |
| Topology: | Linear |
| Sequence class: | Other nucleic acid (chemically synthesized DNA) |
| Antisense: | Yes |
| Sequence: | 5'-TTTACAGAACGATCTCTTCA-3' |

What is claimed is:

1. A pharmaceutical composition for inhibiting cysteine protease comprising a compound of the formula:

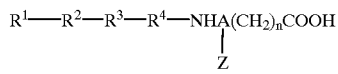

wherein
$R^1$ is a hydrogen atom or an acyl group;
$R^2$, $R^3$ and $R^4$, are the same or are different and are a bond, an amino acid residue or a group of the formula:

$$—Y—R^5—$$

in which $R^5$ is a group resulting from removing the imino group from an amino acid residue; and Y is —O—, —S— or —$NR^6$— in which $R^6$ is a hydrogen atom or a lower alkyl group;

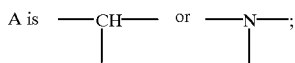

Z is a hydrogen atom, an acyl group or an optionally substituted hydrocarbon group; and
n is 1 or 2;
with the following provisos:
1) when n is 1, then A is

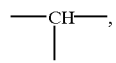

Y is —S— or —$NR^6$—, and at least one of $R^2$, $R^3$ and $R^4$ is the formula —Y—$R^5$—, with the further proviso that when all Y's are —$NR^6$—, then at least one of the amino acid residues is not bound to a hydrogen atom at the α-carbon thereof but is substituted via a carbon atom;
2) when n is 2 and Z is an aldehyde group, then $R^1$ is an acyl group having 6 or more carbon atoms; or
3) when n is 2 and A is

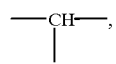

then at least one of $R^2$, $R^3$ and $R^4$ is the formula —Y—$R^5$—;
or an ester or salt thereof, and
a pharmaceutically acceptable carrier.

2. A method for inhibiting interleukin-1β converting enzyme in a mammal, comprising administering an effective amount of the pharmaceutical composition of claim 1 to said mammal.

3. A method for treating or preventing rheumatic arthritis or septic shock in a mammal, comprising administering an effective amount of the pharmaceutical composition of claim 1 to said mammal.

4. A pharmaceutical composition according to claim 1, wherein $R^1$ is an aralkyloxycarbonyl group or an arylcarbonyl group.

5. A pharmaceutical composition according to claim 1, wherein one of $R^2$, $R^3$ and $R^4$ is a bond, and the others are, the same or different, amino acid residues.

6. A pharmaceutical composition according to claim 1, wherein Z is an acyl group derived from a carboxylic acid.

7. A pharmaceutical composition according to claim 1, wherein n is 1.

8. A pharmaceutical composition according to claim 1, wherein n is 2.

9. A pharmaceutical composition according to claim 1, wherein Y is —S— or —$NR^6$— in which $R^6$ is a hydrogen atom or a lower alkyl group, and Z is an aldehyde group or a derivative group thereof.

10. A pharmaceutical composition according to claim 1, wherein Y is —O— or —$NR^6$— in which $R^6$ is a hydrogen atom or a lower alkyl group, and Z is an aldehyde group or a derivative group thereof.

11. A pharmaceutical composition according to claim 9 or 10, wherein Z is a group of the formula:

$$—COW \text{ or } —C(OR^c)_2W$$

in which W is a hydrogen atom, an azido, a $C_{1-6}$ alkyl group or a mono-, di- or tri-halogeno $C_{1-6}$ alkyl group, and $R^c$ is a $C_{1-6}$ alkyl group, a $C_{7-20}$ aralkyl group or a $C_{2-7}$ alkylene group resulting from binding two $R^c$ groups.

12. A pharmaceutical composition for inhibiting interleukin-1β converting enzyme comprising a compound of the formula:

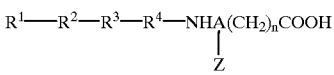

wherein
$R^1$ is a hydrogen atom or an acyl group;
$R^2$, $R^3$ and $R^4$, are the same or are different, and are a bond, an amino acid residue or a group of the formula:

$$—Y—R^5—$$

in which $R^5$ is a group resulting from removing the imino group from an amino acid residue; and Y is —O—, —S— or —$NR^6$— in which $R^6$ is a hydrogen atom or a lower alkyl group;

A is 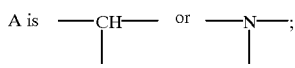

Z is a hydrogen atom, an acyl group or an optionally substituted hydrocarbon group; and n is 1 or 2;

with the following provisos:
1) when n is 1, then A is

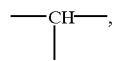

Y is —S— or —NR$^6$—, and at least one of R$^2$, R$^3$ and R$^4$ is the formula —Y—R$^5$—, with the further proviso that when all Y's are —NR$^6$—, then at least one of the amino acid residues is not bound to a hydrogen atom at the α-carbon thereof but is substituted via a carbon atom; or 2) when n is 2 and A is

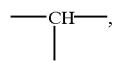

then at least one of R$^2$, R$^3$ and R$^4$ is the formula —Y—R$^5$—;

or an ester or salt thereof, and a pharmaceutically acceptable carrier.

13. A pharmaceutical composition according to claim 12, wherein n is 2.

14. A pharmaceutical composition according to claim 12, wherein Y is —S— or —NR$^6$— in which R$^6$ is a hydrogen atom or a lower alkyl group, and Z is an aldehyde group or a derivative group thereof.

15. A pharmaceutical composition according to claim 12, wherein Y is —O— or —NR$^6$— in which R$^6$ is a hydrogen atom or a lower alkyl group, Z is an aldehyde group or a derivative group thereof and A is

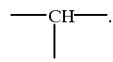

16. A pharmaceutical composition according to claim 12, wherein n is 2 and Z is an aldehyde group, and R$^1$ is an acyl group having 6 or more carbon atoms.

17. A pharmaceutical composition according to claim 14 or 15, wherein Z is a group of the formula:

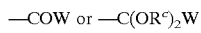

in which W is a hydrogen atom, an azido, a C$_{1-6}$ alkyl group or a mono-, di- or tri-halogeno C$_{1-6}$ alkyl group, and R$^c$ is a C$_{1-6}$ alkyl group, a C$_{7-20}$ aralkyl group or a C$_{2-7}$ alkylene group resulting from binding two R$^c$ groups.

18. A compound of the formula:

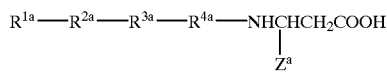

wherein
R$^{1a}$ is an aralkyloxycarbonyl group;
R$^{2a}$, R$^{3a}$ and R$^{4a}$, are the same or are different, and are a bond, an amino acid residue or a group of the formula:

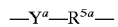

in which R$^{5a}$ is a group resulting from removing the imino group from an amino acid residue; and Y$^a$ is —S— or —NR$^{6a}$— in which R$^{6a}$ is a hydrogen atom or a lower alkyl group;

Z$^a$ is an aldehyde or an acetal group; and with the proviso that at least one of R$^{2a}$, R$^{3a}$ and R$^{4a}$ is the formula —Y$^a$—R$^{5a}$—, with the further proviso that when all Y$^a$'s are —NR$^{6a}$—, then at least one of the amino acid residues is not bound to a hydrogen atom at the α-carbon thereof but is substituted via a carbon atom;

or an ester or salt thereof.

19. A compound according to claim 18, wherein Z$^a$ is an aldehyde group.

20. A compound according to claim 18, wherein the amino acid residue is a residue of amino acid selected from valine and amino-iso-butyric acid.

21. A compound of the formula:

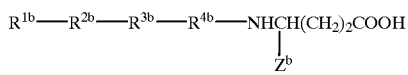

wherein
R$^{1b}$ is an aralkyloxycarbonyl group, a cycloalkylcarbonyl group, a heterocycliccarbonyl group, an arylcarbonyl group which may be substituted with hydroxyl, carboxyl or benzyloxycarbonyl, or an arylsulfonyl group which may be substituted with hydroxyl;

R$^{2b}$, R$^{3b}$ and R$^{4b}$, are the same or are different, and are a bond, an amino acid residue or a group of the formula:

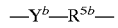

in which R$^{5b}$ is a group resulting from removing the imino group from an amino acid residue; and Y$^b$ is —O—, —S— or —NR$^{6b}$— in which R$^{6b}$ is a hydrogen atom or a lower alkyl group; and Z$^b$ is an aldehyde, an acetal group, an acylalkylcarbonyl group or a substituted alkenyl group;

with the proviso that at least one of R$^{2b}$, R$^{3b}$ and R$^{4b}$ is the formula —Y$^b$—R$^{5b}$—;

or an ester or salt thereof.

22. A compound according to claim 21, wherein R$^{1b}$ is an aralkyloxycarbonyl group or an arylcarbonyl group.

23. A compound according to claim 21, wherein Z$^b$ is an aldehyde group or an acylalkylcarbonyl group.

24. A compound according to claim 21, wherein the acylalkylcarbonyl group is an arylcarbonyloxyalkylcarbonyl group which may be substituted with a halogen atom.

25. A compound according to claim 21, wherein the amino acid residue is a residue of amino acid selected from valine, proline, alanine and glutamine acid.

26. A compound according to claim 21, wherein Y$^b$ is —S— or —NR$^{6b}$— in which R$^{6b}$ is a hydrogen atom or a lower alkyl group, and Z$^b$ is an aldehyde group or an acetal group.

27. A compound according to claim 21, wherein Y$^b$ is —O— or —NR$^{6b}$— in which R$^{6b}$ is a hydrogen atom or a lower alkyl group, and Z$^b$ is an aldehyde group or an acetal group.

28. A compound of the formula:

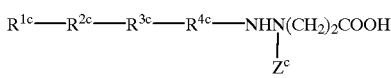

wherein $R^{1c}$ is an aralkyloxycarbonyl group or an arylcarbonyl group;

$R^{2c}$, $R^{3c}$ and $R^{4c}$, are the same or are different, and are a bond, an amino acid residue or a group of the formula:

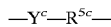

in which $R^{5c}$ is a group resulting from removing the imino group from an amino acid residue; and $Y^c$ is —O—, —S— or —NR$^{6c}$— in which $R^{6c}$ is a hydrogen atom or a lower alkyl group; and $Z^c$ is an aldehyde, an acetal group, a substituted carbonyl group or a substituted alkenyl group;

or an ester or salt thereof.

29. A compound according to claim 28, wherein $R^{1c}$ is an arylcarbonyl group.

30. A compound according to claim 28, wherein $Z^c$ is an acylalkylcarbonyl group or an alkylcarbonyl group which may be substituted with a halogen atom.

31. A compound according to claim 28, wherein the amino acid residue is a residue of amino acid selected from valine, alanine and amino-iso-butyric acid.

32. A compound selected from, which is

N-[N-(9-fluorenylmethyloxycarbonyl)-valyl-aminoisobutyryl]-3-amino-4-oxobutanoic acid, N-{S-[N-(9-fluorenylmethyloxycarbonyl)-valyl]-2-mercaptopropionyl}-3-amino-4-oxobutanoic acid, N-{N-[N-(9-fluorenylmethyloxycarbonyl)-valyl]-1-amino-cyclohexanecarbonyl}-3-amino-4-oxobutanoic acid, N-[N-(2-naphthoyl)-valyl-alanyl]-4-amino-5-oxopentanoic acid, N-[N-(9-fluorenylmethyloxycarbonyl)-valyl-alanyl]-4-amino-5-oxopentanoic acid, N-[N-(2-naphthoyl)-valyl-alanyl]-4-amino-5-oxo-6-(2,6-dichlorobenzoyloxy)hexanoic acid, N-[N-(2-naphthoyl)-glutamyl-alanyl]-4-amino-5-oxopentanoic acid, N-[N-(2-naphtoyl)-valyl-prolyl]-4-amino-5-oxopentanoic acid, N-{N-[N-(9-fluorenylmethyloxycarbonyl)-valyl]-1-amino-cyclohexanecarbonyl}-4-amino-5-oxopentanoic acid, N'-[N-(2-naphthoyl)-valyl-alanyl]-N-(2-carboxyethyl)-chloroacetohydrazide, or N'-[N-(2-naphthoyl)-valyl-alanyl]-N-(2-carboxyethyl)-diphenylphosphinyloxyacetohydrazide, or a salt thereof.

33. A pharmaceutical composition for inhibiting interleukin-1β conventing enzyme which comprises a compound according to claim 18, 21 or 28, and a pharmaceutically acceptable carrier.

34. A method for inhibiting cysteine protease in a mammal comprising administering an effective amount of a compound of the formula:

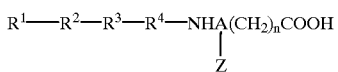

wherein $R^1$ is a hydrogen atom or an acyl group;

$R^2$, $R^3$ and $R^4$, are the same or are different, and are a bond, an amino acid residue or a group of the formula:

in which $R^5$ is a group resulting from removing the imino group from an amino acid residue; and Y is —O—, —S— or —NR$^6$— in which $R^6$ is a hydrogen atom or a lower alkyl group;

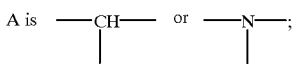

Z is a hydrogen atom, an acyl group or an optionally substituted hydrocarbon group; and n is 1 or 2;

with the following provisos:

1) when n is 1, then A is

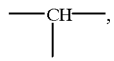

Y is —S— or —NR$^6$—, and at least one of $R^2$, $R^3$ and $R^4$ is the formula —Y—R$^5$—, with the further proviso that when all Y's are —NR$^6$—, then at least one of the amino acid residues is not bound to a hydrogen atom at the α-carbon thereof but is substituted via a carbon atom;

2) when n is 2 and Z is an aldehyde group, then $R^1$ is an acyl group having 6 or more carbon atoms; or 3) when n is 2 and A is

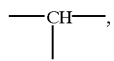

then at least one of $R^2$, $R^3$ and $R^4$ is the formula —Y—R$^5$—;

or an ester or salt thereof, to said mammal.

35. A method for inhibiting interleukin-1β converting enzyme in a mammal comprising administering an effective amount of a compound of the formula:

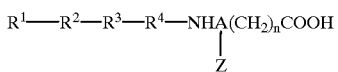

wherein $R^1$ is a hydrogen atom or an acyl group;

$R^2$, $R^3$ and $R^4$, are the same or are different, and are a bond, an amino acid residue or a group of the formula:

in which $R^5$ is a group resulting from removing the imino group from an amino acid residue; and Y is —O—, —S— or —NR$^6$— in which $R^6$ is a hydrogen atom or a lower alkyl group;

A is 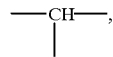

Z is a hydrogen atom, an acyl group or an optionally substituted hydrocarbon group; and n is 1 or 2;

with the following provisos:
1) when n is 1, then A is

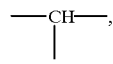

Y is —S— or —NR$^6$—, and at least one of $R^2$, $R^3$ and $R^4$ is the formula —Y—R$^5$—, with the further proviso that when all Y's are —NR$^6$—, then at least one of the amino acid residues is not bound to a hydrogen atom at the α-carbon thereof but is substituted via a carbon atom; or
2) when n is 2 and A is

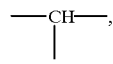

then at least one of $R^2$, $R^3$ and $R^4$ is the formula —Y—R$^5$—;

or an ester or salt thereof, to said mammal.

36. A method for inhibiting interleukin-1β converting enzyme in a mammal comprising administering an effective amount of a compound of the formula:

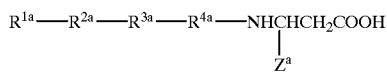

wherein $R^{1a}$ is an aralkyloxycarbonyl group;

$R^{2a}$, $R^{3a}$ and $R^{4a}$, are the same or are different, and are a bond, an amino acid residue or a group of the formula:

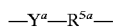

in which $R^{5a}$ is a group resulting from removing the imino group from an amino acid residue; and $Y^a$ is —S— or —NR$^{6a}$— in which $R^{6a}$ is a hydrogen atom or a lower alkyl group; and $Z^a$ is an aldehyde or an acetal group;

with the proviso that at least one of $R^{2a}$, $R^{3a}$ and $R^{4a}$ is the formula —Y$^a$—R$^{5a}$—, with the further Proviso that when all $Y^a$'s are —NR$^{6a}$—, then at least one of the amino acid residues is not bound to a hydrogen atom at the α-carbon thereof but is substituted via a carbon atom;

or an ester or salt thereof, to said mammal.

37. A method for inhibiting interleukin-1β converting enzyme in a mammal comprising administering an effective amount of compound of the formula:

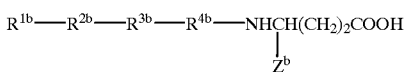

wherein $R^{1b}$ is an aralkyloxycarbonyl group, a cycloalkylcarbonyl group, a heterocycliccarbonyl group, an arylcarbonyl group which may be substituted with hydroxyl, carboxyl or benzyloxycarbonyl, an arylsulfonyl group which may be substituted with hydroxyl or phenyl;

$R^{2b}$, $R^{3b}$ and $R^{4b}$, are the same or are different, and are a bond, an amino acid residue or a group of the formula:

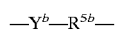

in which $R^{5b}$ is a group resulting from removing the imino group from an amino acid residue; and $Y^b$ is —O—, —S— or —NR$^{6b}$— in which $R^{6b}$ is a hydrogen atom or a lower alkyl group; and $Z^b$ is an aldehyde group, an acetal group, an acylalkylcarbonyl group or a substituted alkenyl group;

with the proviso that at least one of $R^{2b}$, $R^{3b}$ and $R^{4b}$ is the formula —Y$^b$—R$^{5b}$—;

or an ester or salt thereof, to said mammal.

38. A method for inhibiting interleukin-1β converting enzyme in a mammal comprising administering an effective amount of a compound of the formula:

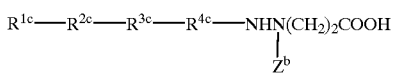

wherein $R^{1c}$ is an aralkyloxycarbonyl group, or an arylcarbonyl group;

$R^{2c}$, $R^{3c}$ and $R^{4c}$, are the same or are different, and are a bond, an amino acid residue or a group of the formula:

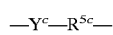

in which $R^{5c}$ is a group resulting from removing the imino group from an amino acid residue; and $Y^c$ is —O—, —S— or —NR$^{6c}$— in which $R^{6c}$ is a hydrogen atom or a lower alkyl group; and $Z^c$ is an aldehyde, an acetal group, a substituted carbonyl group or a substituted alkenyl group;

or an ester or salt thereof, to said mammal.

39. A process for producing a compound of claim 18, which comprises reacting a compound of the formula:

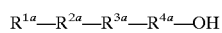

wherein the symbols are as defined in claim 18, or a salt thereof, or an activated derivative thereof, with a compound of the formula:

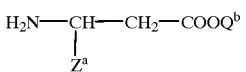

wherein $Q^b$ is a hydrogen atom or a carboxyl-protecting group, the other symbol is as defined in claim 18, or an ester or a salt thereof, and, if necessary, removing the carboxyl-protecting group represented by $Q^b$.

40. A process for producing a compound of claim 21, which comprises reacting a compound of the formula:

wherein the symbols are as defined in claim 21, or a salt thereof, with a compound of the formula:

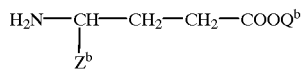

wherein $Q^b$ is a hydrogen atom or a carboxyl-protecting group, the other symbols is as defined in claim 21, or an ester or a salt thereof, and, if necessary, removing the carboxyl-protecting group represented by $Q^b$.

41. A process for producing a compound of claim 28, which comprises reacting a compound of the formula:

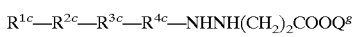

wherein $Q^g$ is a hydrogen atom or a carboxyl-protecting group, and the other symbols are defined in claim 28, or a salt thereof, with a compound of formula:

wherein $X^c$ is a hydroxyl group or a halogen atom, and the other symbol is defined in claim 28, or a salt thereof, and, if necessary, removing the carboxyl-protecting group represented by $Q^g$.

42. The composition of claim 1, wherein $R^5$ is a group of the formula:

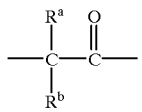

wherein $R^a$ and $R^b$, are the same or are different, and are a hydrogen atom or a $C_{1-8}$ alkyl group which may bind together to form a ring structure.

43. The composition of claim 12, wherein $R^5$ is a group of the formula:

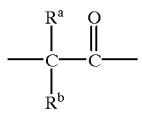

wherein $R^a$ and $R^b$, are the same or are different, and are a hydrogen atom or a $C_{1-8}$ alkyl group which may bind together to form a ring structure.

44. The compound of claim 18, wherein $R^{5a}$ is a group of the formula:

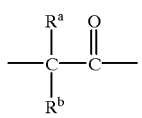

wherein $R^a$ and $R^b$, are the same or are different, and are a hydrogen atom or a $C_{1-8}$ alkyl group which may bind together to form a ring structure.

45. The compound of claim 21, wherein $R^{5b}$ is a group of the formula:

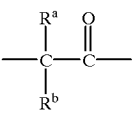

wherein $R^a$ and $R^b$, are the same or are different, and are a hydrogen atom or a $C_{1-8}$ alkyl group which may bind together to form a ring structure.

46. The compound of claim 28, wherein $R^{5c}$ is a group of the formula:

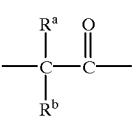

wherein $R^a$ and $R^b$, are the same or are different, and are a hydrogen atom or a $C_{1-8}$ alkyl group which may bind together to form a ring structure.

47. The method of claim 34, wherein $R^5$ is a group of the formula:

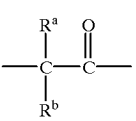

wherein $R^a$ and $R^b$, are the same or are different, and are a hydrogen atom or a $C_{1-8}$ alkyl group which may bind together to form a ring structure.

48. The method of claim 34, wherein $R^5$ is a group of the formula:

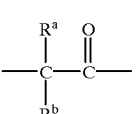

wherein $R^a$ and $R^b$, are the same or are different, and are a hydrogen atom or a $C_{1-8}$ alkyl group which may bind together to form a ring structure.

49. The method of claim 36, wherein $R^{5a}$ is a group of the formula:

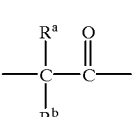

wherein $R^a$ and $R^b$, are the same or are different, and are a hydrogen atom or a $C_{1-8}$ alkyl group which may bind together to form a ring structure.

50. The method of claim 35, wherein $R^{5b}$ is a group of the formula:

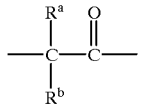

wherein $R^a$ and $R^b$, are the same or are different, and are a hydrogen atom or a $C_{1-8}$ alkyl group which may bind together to form a ring structure.

51. The method of claim 38, wherein $R^{5c}$ is a group of the formula:

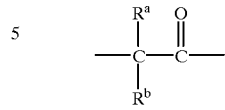

wherein $R^a$ and $R^b$, are the same or are different, and are a hydrogen atom or a $C_{1-8}$ alkyl group which may bind together to form a ring structure.

* * * * *